(12) United States Patent
Wendt et al.

(10) Patent No.: US 8,771,644 B2
(45) Date of Patent: Jul. 8, 2014

(54) IMAGING PROBES

(75) Inventors: Karl-Ulrich Wendt, Frankfurt am Main (DE); Maik Kindermann, Basel (CH); Anja Globisch, Monheim am Rhein (DE)

(73) Assignee: Sanofi, Paris (FR)

( * ) Notice: Subject to any disclaimer, the term of this patent is extended or adjusted under 35 U.S.C. 154(b) by 560 days.

(21) Appl. No.: 12/549,017

(22) Filed: Aug. 27, 2009

(65) Prior Publication Data
US 2010/0189658 A1 Jul. 29, 2010

Related U.S. Application Data

(63) Continuation of application No. PCT/EP2008/000963, filed on Feb. 8, 2008.

(30) Foreign Application Priority Data

Feb. 28, 2007 (EP) .................................... 07004121
Oct. 30, 2007 (EP) .................................... 07291315

(51) Int. Cl.
*A61B 5/00* (2006.01)
*A61B 8/00* (2006.01)
*A61B 10/00* (2006.01)
*A61B 6/00* (2006.01)

(52) U.S. Cl.
USPC .......................................... 424/9.6; 600/476

(58) Field of Classification Search
USPC .................... 424/9.6, 9.61; 600/476
See application file for complete search history.

(56) References Cited

U.S. PATENT DOCUMENTS

| 7,148,030 B2 | 12/2006 | O'Brien et al. |
| 2002/0150961 A1 | 10/2002 | Bogyo et al. |
| 2003/0059847 A1 | 3/2003 | Backes et al. |
| 2004/0002128 A1 | 1/2004 | Chang et al. |
| 2006/0073529 A1 | 4/2006 | Contag et al. |
| 2007/0036725 A1 | 2/2007 | Bogyo et al. |

FOREIGN PATENT DOCUMENTS

| EP | 0 955 309 A1 | 11/1999 | |
| WO | WO88/05434 A1 | 7/1988 | |
| WO | WO97/27220 A2 | 7/1997 | |
| WO | WO 00/73437 | 12/2000 | |
| WO | WO02/056670 A2 | 7/2002 | |
| WO | WO 03/066611 | 8/2003 | |
| WO | WO2004/028449 A2 | 4/2004 | |
| WO | WO2004/080483 A1 | 9/2004 | |
| WO | WO2005/058372 A1 | 6/2005 | |
| WO | WO 2005/082876 | * 9/2005 | ........... C07D 307/32 |
| WO | WO 2007/027653 | 3/2007 | |

OTHER PUBLICATIONS

Lecaille et al., Biochem.J., 2003, 375, p. 307-312.*
Tully, David C. et al., "Synthesis and SAR of arylaminoethyl amides as noncovalent inhibitors of cathepsin S: P3 cyclic ethers," Bioorganic & Medicinal Chemistry Letters (2006), vol. 16, pp. 5112-5117.
Chatterjee, Arnab K. "Synthesis and SAR of succinamide peptidomimetic inhibitors of cahepsin S," Bioorganic & Medicinal Chemistry Letters (2007), vol. 17, pp. 2899-2903.
Tully, David C. et al., "Arylaminoethyl carbamates as a novel series of potent and selective cathepsin S inhibitors," Bioorganic & Medicinal Chemistry Letters (2006), vol. 16, pp. 5107-5111.
Merrifield, Bruce, "[1] Concept and Early Development of Solid-Phase Peptide Synthesis," Methods in Enzymology (1997), vol. 289, pp. 3-13.
Baruch, Amos et al., "Enzyme activity—it's all about image," TRENDS in Cell Biology (2004), vol. 14, pp. 29-35.
Bremer, Christoph et al., "In vivo molecular target assessment of matrix metalloproteinase inhibition," Nature Medicine (2001), vol. 7, pp. 743-748.
Bremer, C., "Imaging of Proteases for Tumor Detection and Differentiation," Ernst Schering Research Foundation Workshop, Springer, DE, pp. 159-170, 2005.
Jeffrey, Douglas A. et al., "Chemical proteomics and its application to drug discovery," Current Opinion in Biotechnology (2003), vol. 14, pp. 87-95.
Fischer, Rainer et al., "A Targeted Protease Substrate for a Quantitative Determination of Protease Activities in the Endolysosomal Pathway," ChemBioChem (2006), vol. 7, pp. 1428-1434.
Blum, Galia et al., "Dynamic imaging of protease activity with fluorescently quenched activity-based probes," Nature Chemical Biology (2005), vol. 1, pp. 203-209.
Weissleder, Ralph et al., "In vivo imaging of tumors with protease-activated near-infrared fluorescent probes," Nature Biotechnology (1999), vol. 17, pp. 375-378.
Johansson, Mary Katherine et al., "Intramolecular Dimers: A New Design Strategy for Fluorescence—Quenched Probes," Chemistry—A European Journal (2003), vol. 9, pp. 3466-3471.
Sapsford, Kim E. et al., "Materials for Fluorescence Resonance Energy Transfer Analysis: Beyond Traditional Donor-Acceptor Combinations" Angewandte Chemie International Edition (2006), vol. 45, pp. 4562-4588.
Evans, Michael J. et al., "Mechanism-Based Profiling of Enzyme Families," Chemical Reviews (2006), vol. 106, pp. 3279-3301.
Monsees, Thomas et al., "Synthesis and Characterization of a Bioluminogenic Substrate for α-Chymotrypsin," Analytical Biochemistry (1994), vol. 221, pp. 329-334.
Niles, Andrew L. et al., "A homogeneous assay to measure live and dead cells in the same sample by detecting different protease markers," Analytical Biochemistry (2007), vol. 366, pp. 197-206.
Panchuk-Voloshina, Nataliya et al., "Alexa Dyes, a Series of New Fluorescent Dyes that Yield Exceptionally Bright, Photostable Conjugates," The Journal of Histochemistry & Cytochemistry (1999), vol. 47, pp. 1179-1188.

(Continued)

*Primary Examiner* — Michael G Hartley
*Assistant Examiner* — Leah Schlientz
(74) *Attorney, Agent, or Firm* — Ronald G. Ort

(57) ABSTRACT

The present invention relates to molecular probes of the formula (I)

{L1-R1-L}$_n$-A-CO—NH—R2-L2     (I)

as defined herein that allow for the observation of the catalytic activity of a selected cathepsin in in vitro assays, in cells or in multicellular organisms, a method for their preparation and the use thereof.

15 Claims, No Drawings

(56) References Cited

OTHER PUBLICATIONS

Verhelst, Steven H.L. et al., "Dissecting Protein Function Using Chemical Proteomic Methods," QSAR and Combinatorial Science (2005), vol. 24, pp. 261-269.

Turk, Vito et al., "Lysosomal cysteine proteases: facts and opportunities," The EMBO Journal (2001), vol. 20, pp. 4629-4633.

Grabowska, Urszula B. et al., "Recent developments in cathepsin K inhibitor design," Current Opinion in Drug Development and Discovery (2005), vol. 8, pp. 619-630.

Yasuda, Yoshiyuki et al., "The role of cathepsins in osteoporosis and arthritis: Rationale for the design of new therapeutics," Advanced Drug Delivery Reviews (2005), vol. 57, pp. 973-993.

International Search Report dated Aug. 26, 2008.

\* cited by examiner

IMAGING PROBES

The present invention relates to molecular probes (substrates) that allow for the observation of the catalytic activity of individual proteolytic enzymes or groups of proteolytic enzymes in in vitro assays, in cells or in multicellular organisms. The invention furthermore relates to methods for the synthesis and the design of such probes (substrates).

BACKGROUND OF THE INVENTION

Proteolytic enzymes (proteases) cleave or degrade other enzymes or peptides in- and outside of the living cell. Proteases are involved in a multitude of vital processes, many of which are critical in cellular signalling and tissue homeostasis. Aberrant or enhanced activity of proteases is associated with a variety of diseases including cancer, osteoarthritis, arteriosclerosis, inflammation and many others (M. J. Evans, B. F. Cravatt, Chem. Rev. 2006, 106, 3279-3301). Since proteolytic activity has to remain under stringent control in living systems many proteases are expressed as inactive precursor proteins (zymogens) which are activated by controlled proteolytic cleavage. Additional control of proteolytic activity results from endogenous inhibitors that bind to and thereby inactivate catalytically active form of the enzyme. In view of this stringent regulation the investigation of protease function in cellular or physiological events requires the monitoring of protease activity rather than the monitoring of protease expression alone. Consequently, a variety of activity based chemical probes have been proposed in the literature. Commonly applied protease probes generate a detectable signal either (i) through enzymatic cleavage of a peptide bond leading the spatial separation of a fluorophore from a fluorescence quencher or (ii) by covalent attachment of a mechanism based inhibitor to the protease of interest. The localization and quantitative investigation of the activity and inhibition of a specific protease or a group of proteases (e.g. in cell-based assays or whole-animal imaging experiments) requires the development of imaging probes that (i) reach the physiologically relevant locus of protease action (e.g. the cytosol of a cell or a specific organ in whole animal imaging) and (ii) are selective for the desired protease or a group of proteases. The generation of protease selective probes has imposed a considerable challenge for the field. The present invention relates (i) to novel highly selective probes for cysteine proteases preferably from the cathepsin subfamily, (ii) to the application of these probes in vitro assays, in cells or in multicellular organisms (e.g. by the means of molecular imaging) and (iii) to methods for the synthesis and the design such probes.

Within recent years several molecular imaging technologies (optical and non-optical) have become more and more important for the non-invasive visualisation of specific molecular targets and pathways in vivo. Since the information content of any image signal is primarily a function of internal contrast, the development of internally quenched imaging probes that are activatable upon enzymatic reaction (e.g. cleavage of a peptide bond) has been commonly applied to image and localize catalytically active proteases. The generation of probes that are selective for individual proteases and exhibit the ability to reach the locus of protease action in vivo has rarely been achieved with conventional approaches. Medicinal chemists in the pharmaceutical industry face related challenges in the development of drugs with appropriate pharmacokinetic properties and appropriate specificity for a given target. In our invention we have devised a new route towards selective activity based probes for cysteine proteases and have applied this approach to proteases from the cysteine cathepsin subfamily.

Cysteine proteases are characterized by a cysteine residue in the active site which serves as a nucleophile during catalysis. The catalytic cysteine is commonly hydrogen bonded with appropriate neighboring residues, so that a thiolate ion can be formed. When a substrate is recognized by the protease, the scissile peptide bond is placed in proximity to the catalytic cysteine, which attacks the carbonyl carbon forming an oxo-anion intermediate. The amide bond is then cleaved liberating the C-terminal peptide as an amine. The N-terminal portion of the scissile peptide remains in the covalent acyl-enzyme intermediate, which is subsequently cleaved by water, resulting in regeneration of the enzyme. The N-terminal cleavage product of the substrate is liberated as a carboxylic acid.

The human genome encodes 11 papaine-like cathepsins (human clan CA proteases or the cysteine cathepsins: B, C, F, H, K, L, O, S, V, W, X) which are implicated with various functions including general protein degradation in lysosomes (house keeping function), processing of antigens, processing of granular proteases, and matrix collagen degradations. Malfunction of cystein cathepsins have been associated with a number of pathological events such as osteoarthritis, cancer biology (angiogenesis and tumorigenesis), neurological disorders (e.g. pain) and osteoporosis (Y. Yasuda et al. Adv. Drug Delivery Rev. 2005, 57, 973-993) and consequently some of the cystein cathepsins have been validated as relevant drug targets for therapies over recent years (Turk, V.; Turk, B.; Turk, D. Embo J, 2001, 20, 4629-4633).

For example, Cathepsin K and S are implicated in bone and cartilage degradation and are related to osteoporosis and arthritis.

Furthermore, Cathepsin K is predominantly found in osteoclasts and was shown to bee crucial for normal bone remodelling (bone resorption). A deficiency of Cathepsin K activity results in a bone sclerosis disorder (pycnodysosis), whereas over expression in cathepsin K accelerated the turnover of bone material as it is indicative for osteoporosis. Cathepsin K also shows potent collagenase activity, cleaving triple helical collagens in their helical domains. In Osteoarthritis the cartilage matrix is undergoing massive erosion including the degradation of type II collagen (Y. Yasuda et al. Adv. Drug Delivery Rev. 2005, 57, 973-993). Thus, inhibition of Cathepsin B and K, for example, is a useful method for the treatment of degenerative joint diseases such as, for example, osteoarthritis. Cathepsin K inhibition, for example, leads to inhibition of bone. Cathepsin S plays a major role to initiate a MHC class II related immune response towards an antigen. Being the main invariant cain-processing protease in dendritic cells, Cathepsin S appears as attractive drug target in immune related diseases. Furthermore Cathepsin S might be also important for extracellular matrix degradation and shows significant elastase and proteoglycan-degrading activity. Cathepsin S is therefore implicated in disorders involving excessive elastolysis, such as chronic obstructive pulmonary disease (e.g. emphysema), bronchiolitis, excessive airway elastolysis in asthma and bronchitis, pneumonities and cardiovascular disease such as plaque rupture and atheroma.

Cathepsin L appears to be involved in epidermal homeostasis, regulation of the hair cycle and also MHC class II-mediated antigen presentation.

Cathepsin B is associated with pathological trypsin activation in the early stage of pancreatitis and contributes to TNF-alpha induced hepatocyte apoptosis.

For proteolytic enzymes, it is their activity, rather than mere expression level, that dictates their functional role in cell physiology and pathology. Accordingly, molecules that inhibit the activity of cathepsin proteases are useful as therapeutic agents in the treatment of diseases and the development of specific imaging biomarkers that visualize the proteolytic activity as well as their inhibition through drug candidates may accelerate target validation, drug development and even clinical trials (H. Pien, A. J. Fischman, J. H. Thrall, A. G. Sorensen, Drug Discovery Today, 2005, 10, 259-266). Using activity based imaging reagents, a specific protein or protein family can be readily monitored in complex protein mixtures, intact cells, and even in vivo. Furthermore, enzyme class specific probes can be used to develop screens for small molecules inhibitors that can be used for functional studies (D. A. Jeffery, M. Bogyo Curr. Opp. Biotech. 2003, 14, 87-95).

So far, activity based imaging probes have been developed to monitor and label cathepsin B and L in cell based assays (G. Blum et al. Nat. Chem. Biol, 2005, 1, 203-209), several cathepsins (R. Weissleder et al. Nat. Biotech. 1999, 17, 375-378) and matrix metalloproteinases in tumour tissue (C. Bremer et al. Nat. Med. 2001, 7, 743-748).

Another tool to monitor protease activity consists in bioluminescent assay. This method makes use of derivatives of luciferin in enzyme activity assays or non-enzymatic biological assays where the luciferin derivative serves as a substrate for a desired enzyme and is a prosubstrate for luciferase. A first proteolytic cleavage releases luciferine which is subsequently converted by luciferase, detectable as a luminescent signal. This secondary assay has a similar application spectra than fluorescent probes and presents the additionally advantage of a high signal to noise ratio.

The enzymatic mechanism used by the cysteine cathepsins has been well studied and is highly conserved. From the investigation and screening data of cleavable peptides, electrophilic substrate analogs have been developed that only react in the context of this conserved active site. The electrophilic center in such probes is usually part of a so called "warhead", a molecular entity that is optimized in its electrophilic character and its geometric placement to fit perfectly into the active site of a cysteine cathepsin, where it reacts with the catalytic cysteine residue. A wide variety of such electrophilic substrates have been described as mechanism based cysteine protease inhibitors including for example but not exclusively: diazomethyl ketones, fluoromethyl ketones, acyloxymethyl ketones, O-acylhydroxylamines, vinyl sulfones and epoxysuccinic derivatives (S. Verhelst, M. Bogyo QSAR Comb. Sci. 2005, 24, 261-269).

To be effective as biological tools, protease inhibitors must be not only very potent but also highly selective in binding to a particular protease. The development of small molecule inhibitors for specific proteases has often started from peptide substrates. Although peptides display a diverse range of biological properties, their use as drugs can be compromised by their instability and their low oral bioavailability. To be effective drugs, protease inhibitors with reduced peptide-like character, high stability against non selective proteolytic degradation, high selectivity for a given protease, and good bioavailability to the locus of protease action are desirable. These requirements led to the development of cysteine-cathepsin inhibitors A-B with non-peptidic chemical scaffolds A, which are covalently linked with an electrophilic warheads B. When bound to the cysteine-cathepsin B reacts covalently with the catalytic cysteine (mechanism based inhibitor). In many cases the selectivity and pharmacokinetic properties of such inhibitors were successfully optimized in the context of biomedical research. To enable effective nucleophilic attack by the catalytic cysteine, the electrophilic center of such inhibitors must be oriented precisely within the active site of the enzyme. The special arrangement of catalytic cysteine to the electrophilic carbon atom of the warhead corresponds well to the spatial arrangement of the catalytic cysteine and the peptide carbonyl of a scissile peptide substrate. This comparison guided us to the idea that a "redesign" of optimized covalent inhibitors (with a chemical scaffold A and an electrophilic warhead B) into a cleavable substrate should be possible. Since the chemical scaffold A can be considered as the main determinant of inhibitor selectivity, our approach would allow for the transfer of the selectivity or parts of the selectivity of an optimized inhibitor into an activity based chemical probe. We refer to this process as "reversed design" of selective activity based probes from selective cysteine cathepsin inhibitors.

The invention relates to a molecular probe for cysteine proteases of the formula (I)

{L1-R1-L}$_n$-A-CO—NH—R2-L2    (I)

wherein
A is a group recognizable by a cathepsin;
R1 is a linker;
R2 is a bond or a linker;
L is a bond or a group allowing for a facile conjugation of the group L1;
L1 and L2 are, independent of each other, at least one label optionally bound to a solid support; and
n is 1;
or
R2 is a bond;
L2 is a substrate, suitable for a coupled bioluminescent assay; and
n is 0.

A further embodiment of the invention is a molecular probe for cysteine proteases of the formula (I) wherein
n is 1,
A is a group recognizable by a cysteine cathepsin;
R1 and R2 are, independently of each other, a linker;
L is a bond or a group allowing for a facile conjugation of the group L1; and
L1 and L2 are, independent of each other, at least one label optionally bound to a solid support.

The compounds of the formula (I) are activity based probes (substrates) for cysteine proteases, preferably from the cysteine cathepsin subfamily.

In their most basic form, the chemical probe consists of four functional elements, a) an amide group —CO—NH— as a reactive group, that can be cleaved by the action of a protease, b) a scaffold A which defines the selectivity for a given protease target, c) linker moieties R1 and R2 to connect subunits to each other and d) set of label L1 and L2 for detection.

Group A is preferably the main determinant for specificity towards a given cysteine cathepsin or a group of cysteine cathepsins, preferably for cathepsin K or S, e.g. as shown in compounds 2.-114. Imaging probes of the present invention show selectivity for a given cysteine cathepsin of the factor 1000 to 1, preferably a factor 100 to 1, wherein selectivity is defined by the relative turnover number (turnover number with enzyme 1 versus turnover number with enzyme 2) at a preferred substrate concentration. The relative turnover number is determined for each enzyme pair by dividing the turnover number of the enzyme of interest (enzyme 1) by the turnover number of another enzyme against which selectivity is desired (enzyme 2). For in vivo applications high selectivity is desired at low (e.g. micromolar or sub micromolar) substrate concentrations.

Scheme 1 shows the reaction of a protease P with a substrate wherein A represents the specificity determinant, and P represents the protease with its reactive cysteine comprising the thiol group S⁻:

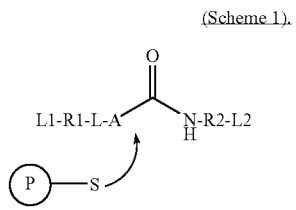

(Scheme 1).

The reaction rate is dependent on the structure of the substrate.

The linker group R1 or R2 is preferably a flexible linker connected to a label L1 or L2, respectively, or a plurality of same or different label L2 or L1. The linker group is chosen in the context of the envisioned application, i.e. in context of an activity based imaging probe for a specific protease. The linker may also increase the solubility of the substrate in the appropriate solvent. The linkers used are chemically stable under the conditions of the actual application. The linker does not interfere with the reaction of a selected protease target nor with the detection of the label L1 and/or L2, but may be constructed such as to be cleaved at some point in time. More specifically, the linker group R1 or R2 is a straight or branched chain alkylene group with 1 to 300 carbon atoms, wherein optionally
(a) one or more carbon atoms are replaced by oxygen, in particular wherein every third carbon atom is replaced by oxygen, e.g. a poylethyleneoxy group with 1 to 100 ethyleneoxy units; and/or
(b) one or more carbon atoms are replaced by nitrogen carrying a hydrogen atom, and the adjacent carbon atoms are substituted by oxo, representing an amide function —NH—CO—; and/or
(c) one or more carbon atoms are replaced by an ester function —O—CO—;
(d) the bond between two adjacent carbon atoms is a double or a triple bond; and/or
(e) two adjacent carbon atoms are replaced by a disulfide linkage.

The label L1 and L2 of the substrate can be chosen by those skilled in the art dependent on the application for which the probe is intended.

The label L1 and L2 is independently of each other a spectroscopic probe such as a fluorophore; a quencher or a chromophore; a magnetic probe; a contrast reagent; a molecule which is one part of a specific binding pair which is capable of specifically binding to a partner; a molecule covalently attached to a polymeric support, a dendrimer, a glass slide, a microtiter plate known to those proficient in the art; or a molecule possessing a combination of any of the properties listed above.

A preferred embodiment of the present invention is the use of a modified aminoluciferin or a carboxy-terminal protected derivative thereof as a reporter group, which upon cleavage from the central scaffold A can generate a luminescent signal through its conversion by a luciferase. Therefore, label L2 may alternatively be a substrate, suitable for a coupled bioluminescent assay, characterized in a modified aminoluciferin or a carboxy-terminal protected derivative thereof as a reporter group.

U.S. Pat. No. 7,148,030 discloses examples of bioluminescent protease assays comprising peptides as cathepsin substrates which are linked to modified aminoluciferines.

Preferred is a probe which consists of intramoleculary quenches fluorescent probes comprising a polymeric backbone and a plurality of fluorochromes covalently linked via scaffold A to the backbone at a density which leads to fluorescent quenching. Another preferred embodiment of the present invention is the use of a dendritic macromolecule onto which a two or more fluorophors are covalently linked via scaffold A at a density which leads to fluorescent quenching. The use of a polymeric probe has the advantage of localized probe delivery (targeting) and a prolonged circulation time in the blood stream of an animal or humans. Polymer conjugation alters the biodistribution of low-molecular-weight substances, enabling tumour-specific targeting (by the enhanced permeability and retention effect (EPR effect)) with reduced access to sites of toxicity and the combination of polymer conjugates with low-molecular-weight imaging probes is a most preferred embodiment of the present invention for imaging of multicellular organisms including mammals such as mice, rats etc. The polymeric backbone can consist of any biocompatible polymer and may comprise a polypeptide, a polysaccharide, a nucleic acid or a synthetic polymer. A comprehensive summary of polymers useful in the context of the present invention can be found in M. J. Vincent et al. Trends Biotech. 2006, 24, 39-47 and R. Duncan, Nature Reviews Cancer, 2006, 688-701. A further description of polymers useful in the context of the present invention is disclosed in WO99/58161. The polymeric or dendrimeric probe can comprise protective chains covalently linked to the backbone or the dendritic molecule. Protective chains include polyethylene glycol, methoxypolyethyleneglycole and further copolymers of ethyleneglycole.

The probe of the present invention can additionally comprise a targeting moiety such as an antibody, an antibody fragment, a receptor-binding ligand, a peptide fragment or a synthetic protein inhibitor.

Label L1 and L2 can further be positively charged linear or branched polymers. Said polymers are known to those skilled in the art to facilitate the transfer of attached molecules over the plasma membrane of living cells. This is especially preferred for substances which otherwise have a low cell membrane permeability or are in effect impermeable for the cell membrane of living cells. A non cell permeable chemical probe will become cell membrane permeable upon conjugation to such a group L1 or L2. Such cell membrane transport enhancer groups L1 and L2 comprise, for example, a linear poly(arginine) of D- and/or L-arginine with 6-15 arginine residues, linear polymers of 6-15 subunits each of which carry a guanidinium group, an oligomer or a short-length polymer of from 6 to up to 50 subunits, a portion of which have attached guanidinium groups, and/or parts of the sequence of the HIV-tat protein, for example the subunit Tat49-Tat57 (RKKRRQRRR in the one letter amino acid code). A linear poly(arginine) of D- and/or L-arginine with 6-15 arginine residues is preferably utilized as polymeric label in case L1 is one member and L2 is the other member of two interacting spectroscopic probes L1/L2, such as in a FRET pair.

Most preferred as label L1 and/or L2 are spectroscopic probes. Most preferred as label L2 are molecules representing one part of a spectroscopic interaction pair with L1, furthermore a label which is capable of specifically binding to a partner and molecules covalently attached to a solid support.

Particularly preferred are label such that L1 is one member and L2 is the other member of two interacting spectroscopic probes L1/L2, wherein energy can be transferred non-radioactively between the donor and acceptor (quencher) through either dynamic or static quenching. Such said pair of label L1/L2 changes its spectroscopic properties upon reaction/cleavage from the corresponding cysteine cathepsin protease. An example of such a pair of label L1/L2 is a FRET (Förster resonance energy transfer) pair, e.g. a pro-fluorescent probe covalently labelled at one end (e.g. L1) with a donor (reporter), and the another position (L2) with an acceptor (quencher), or vice versa.

In particular, L1 is a donor (reporter) and L2 is an acceptor (quencher), or L1 is a quencher and L2 is a reporter. In using this probe, the reaction of the cysteine protease with the probe will lead to a change in fluorescence. The reporter-quencher distance within the double labelled substrate is changed upon reaction with the protease leading to a spatial separation of reporter and quencher witch causes the appearance of fluorescence or change of the emission wavelength. A broad selection of reporter groups may be used as label L1 or L2, respectively, including e.g. near infra-red emitting fluorophores. The substrate containing reporter and quencher remains dark until it reacts with the protease, whereupon the reaction mixture is "lit up" switching on the fluorophore emission, since the reporter label and the quencher label are now spatially separated. Fluorescence quenching and energy transfer can be measured by the emission of only one of the two labels, the quenched or energy donor label. When energy transfer occurs and the energy accepting label is also fluorescent, the acceptor label fluorescence can also be measured. A donor label of these two interacting label can be chosen from chemoluminescent donor probes which eliminates the need of an excitation lamp and reduces acceptor background fluorescence. The mentioned particular method using such double-labelled substrates is useful to determine reaction kinetics based on fluorescence time measurements, and may be applied in vivo as well as in vitro.

Alternatively, the label L2 of the substrate may be a solid support or be additionally attached to solid support or attached or attachable to a polymer/solid support. Linear poly (arginine) of D- and/or L-arginine with 6-15 arginine residues is preferably utilized as polymeric label for a L1/L2 FRET pair.

Particular preferred combinations are two different affinity label, especially a pair of spectroscopic interacting label L1/L2, e.g. a FRET pair. An affinity label is defined as a molecule which is one part of a specific binding pair which is capable of specifically binding to a partner. A specific binding pair considered is e.g. biotin and avidin or streptavidin furthermore methotrexate, which is a tight-binding inhibitor of the enzyme dihydrofolate reductase (DHFR).

Appropriate pairs of reporters and quenchers can bee chosen by those skilled in the art. Typically reporter and quencher are fluorescent dyes with large spectral overlap as, for example, fluorescein as a reporter and rhodamine as a quencher. Other quenchers are gold clusters, and metal cryptates.

A second class of quenchers used in this invention are "dark quenchers" (Johansson, M. K. et al., Chem. Eur. J. 9:3466-3471, 2003), i.e. dyes without native fluorescence having absorption spectra that overlap with the emission spectra of common reporter dyes leading to maximal FRET quenching. Furthermore pairs of dyes can be chosen such that their absorption bands overlap in order to promote a resonance dipole-dipole interaction mechanism within a ground state complex (static quenching).

Particular fluorophores and quenchers considered are: Alexa dyes, including Alexa 350, Alexa 488, Alexa 532, Alexa 546, Alexa 555, Alexa 635 and Alexa 647 (Panchuk-Voloshina, N. et al., J. Histochem. & Cytochem. 47:1179-1188, 1999); dimethylaminocoumarin (7-dimethylaminocoumarin-4-acetic acid succinimidyl ester supplied as product D374 by Molecular Probes); quenchers QSY 35, QSY 9 and QSY 21 (Molecular Probes, Inc., Eugene, Oreg. 97402, USA); Cyanine-3 (Cy 3), Cyanine 5 (Cy 5) and Cyanine 5.5 (Cy 5.5) (Amersham—GE Healthcare, Solingen, Germany); BHQ-1, BHQ-2 and BHQ-3 (Black Hole Quencher™ of Biosearch Technologies, Inc., Novato, Calif. 94949, USA); fluorophores ATTO 488, ATTO 532, ATTO 600 and ATTO 655 and quenchers ATTO 540Q and ATTO 612Q (Atto-Tec, D57076 Siegen, Germany); fluorophores DY-505, DY-547, DY-632 and DY-647 (Dyomics, Jena, Germany); 5/6-carboxyfluorescein, tetramethylrhodamine, 4-dimethylaminoazobenzene-4'-sulfonyl derivatives (Dabsyl) and 4-dimethylaminoazobenzene-4'-carbonyl derivatives (Dabcyl). These can be advantageously combined in the following combinations:

| Fluorophore | Quencher |
|---|---|
| Alexa 350, dimethylaminocoumarin, 5/6-carboxyfluorescein, Alexa 488, ATTO 488, DY-505 | Dabsyl, Dabcyl, BHQ 1, QSY 35 |
| 5/6-carboxyfluorescein, Alexa 488, Alexa 532, Alexa 546, Alexa 555, ATTO 488, ATTO 532, tetramethylrhodamine, Cy 3, DY-505, DY-547, | BHQ 2, QSY 9, ATTO 540Q |
| Alexa 635, Alexa 647, ATTO 600, ATTO 655, DY-632, Cy 5, DY-647 Cy 5.5 | BHQ 3, ATTO 612Q, QSY 21 |

Bioluminescent assays that are linked to an enzymatic event yield light coupled to the instantaneous rate of catalysis. The method comprises an amino-modified beetle amino-luciferin or a carboxy-terminal protected derivative thereof were the amino-group of aminoluciferin is linked via an amide bond to the central scaffold A, resulting in a substrate that is recognized and subsequently cleaved by a cathepsin. The enzymatic activity of a cathepsin leads to the cleavage of the peptide bond which links the aminoluciferin to the scaffold A liberating the aminoluciferin a substrate for a luciferase. The following reaction of the luciferase with its substrate yields a detectable signal (luminescence). The method thus relates cathepsin activity with a second enzymatic reaction, generating luminescence as a read-out signal. This type of assay requires the development of a "pro-luciferin" ("caged luciferin"), which is recognized by a luciferase as a substrate only when converted to luciferine by a precedent enzymatic event e.g. proteolytic cleavage. In this way, the luminescent signal is directly dependent on the previous enzymatic event. It is therefore a further embodiment of the present invention to provide a probe for detecting proteolytic activity of cathepsins by means of luminescence.

In a particular embodiment, the method involves a substrate wherein L2 is a solid support or attached to a solid support further carrying one member of the reporter/quencher pair, or wherein L2 is a combination of a solid support and one member of the reporter/quencher pair, and L1 is the other member of this pair. In this way, the dark solid support becomes fluorescent upon reaction with the appropriate protease.

A solid support, may be a glass slide, a microtiter plate or any polymer known to those proficient in the art, e.g. a functionalized polymers (preferably in the form of beads), chemically modified oxidic surfaces, e.g. silicon dioxide, tantalum pentoxide or titanium dioxide, or also chemically modified metal surfaces, e.g. noble metal surfaces such as gold or silver surfaces. A solid support may also be a suitable sensor element.

Preferably, the compound of the formula (I) comprises a group A being an inhibitor of cathepsin K. International patent application WO06076796, WO06076797, WO06063762 and WO05049028 disclose examples of selective cathepsin K inhibitors that may be used to be transformed into probes of the formula (I). More preferred, the compound of the formula (I) is a probe for cathepsin K characterized by a compound comprising the following preferred scaffolds A:

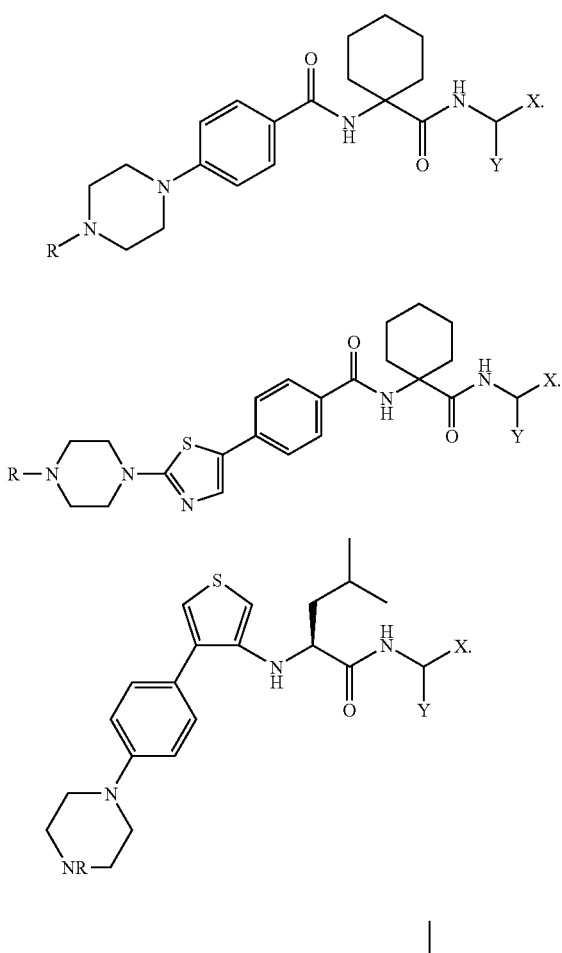

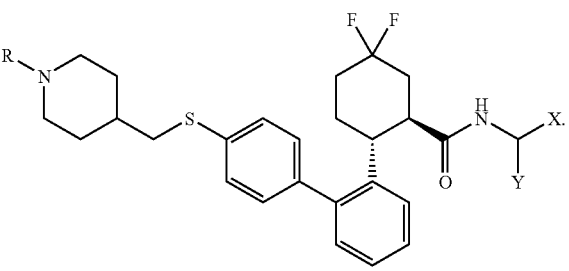

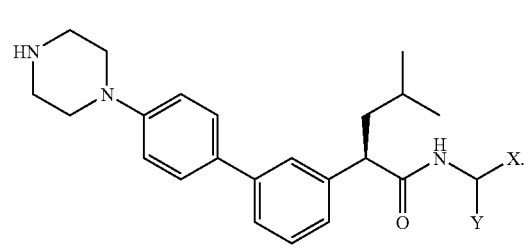

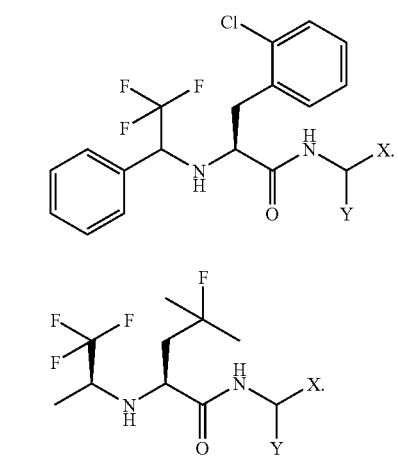
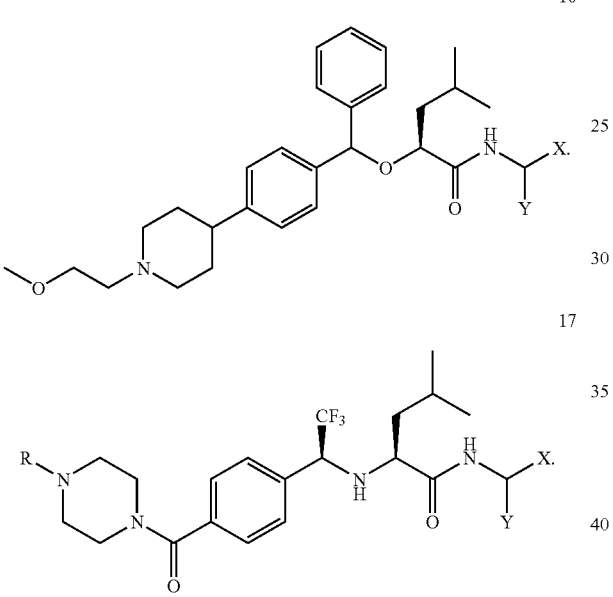
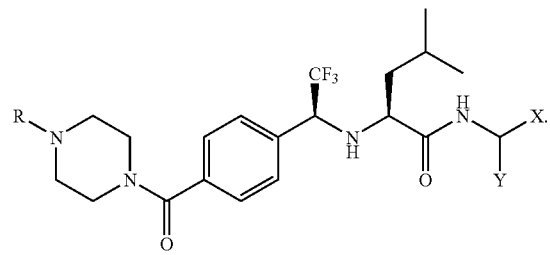
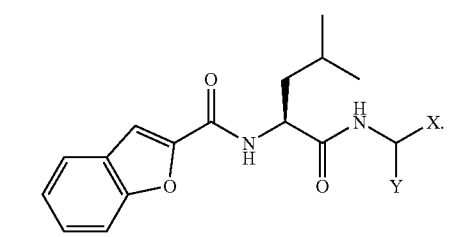
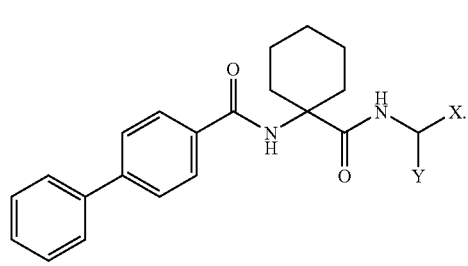

-continued
28
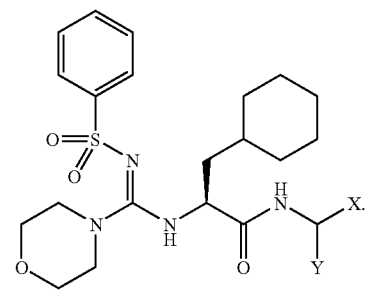
29
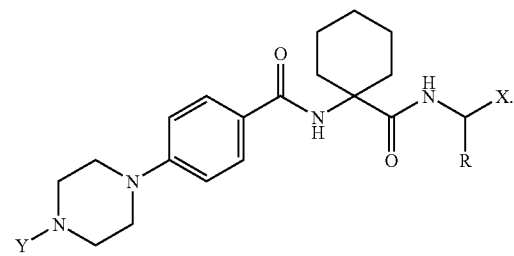
30
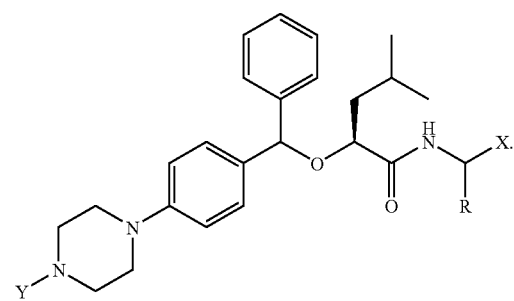
31
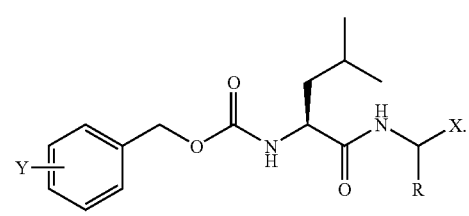
32
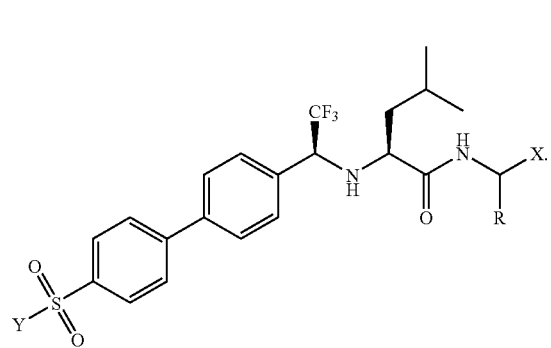
-continued
33
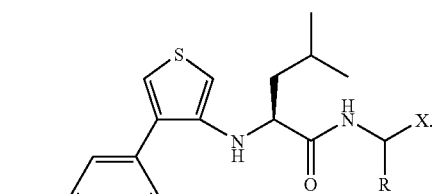
34
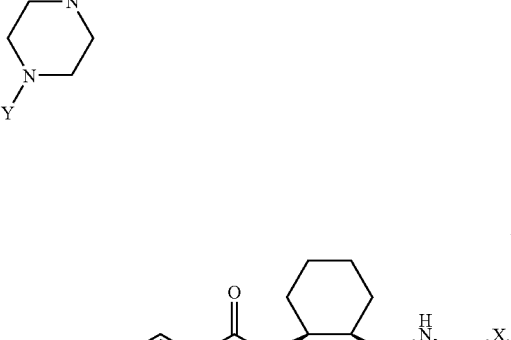
35
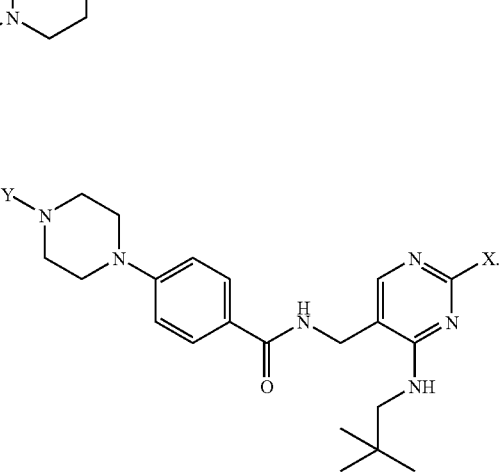
36
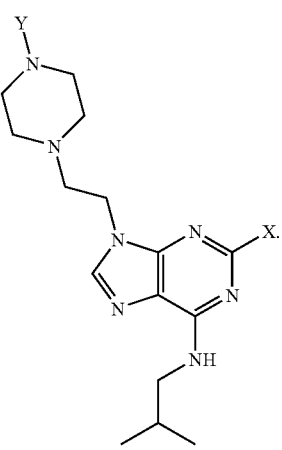

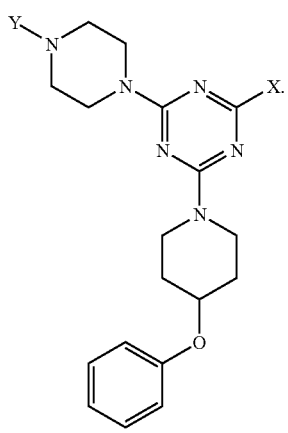
37
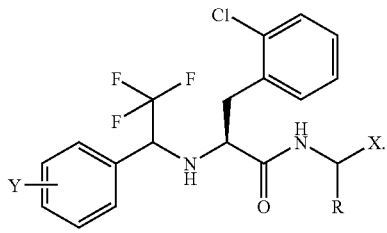
45
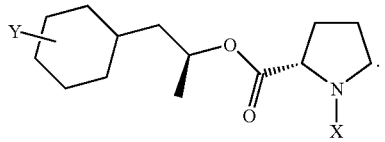
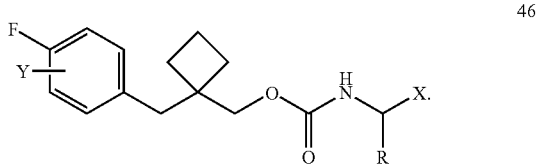
46
38
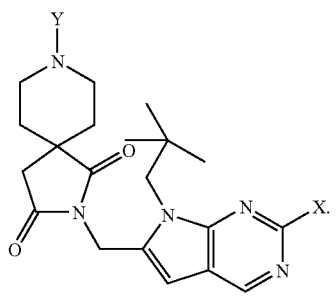
39
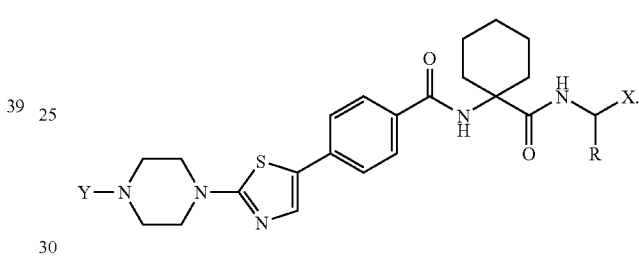
47
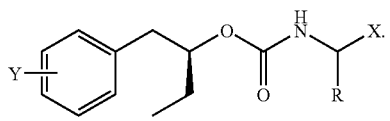
40
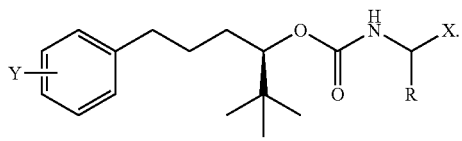
41
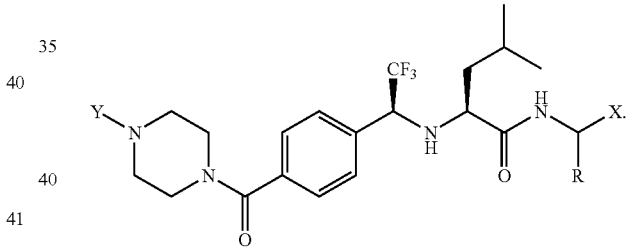
48
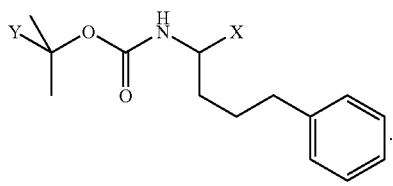
42
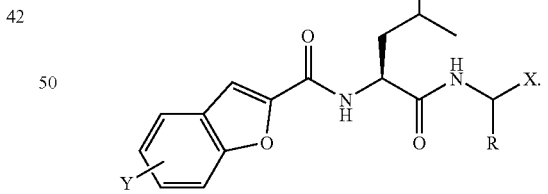
49
43
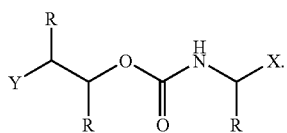
44
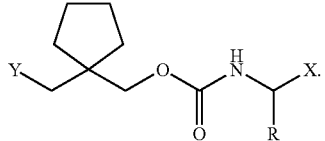
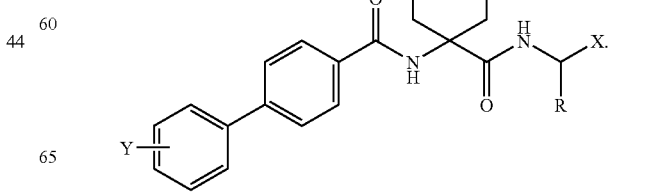
50

-continued

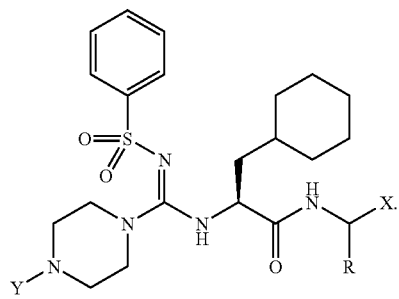

63 wherein

X is —CONH—R2-L2,

Y is {L-R1-L1}$_n$,

R1, R2, L, L1, L2 and n are as described above, and

R is H, $C_1$-$C_6$-Alkyl.

Compounds 1.-28. are substrates for cathepsin K with L1 in the S1 pocket, compounds 29.-63. for cathepsin K with L1 in the S3 pocket or beyond (outward).

Further preferably, the compound of the formula (I) comprises a group A being an inhibitor of cathepsin S. International patent applications WO04089395, WO05040142, WO0055144, WO05074904 and WO0069855 disclose examples of selective cathepsin S inhibitors that may be used to be transformed into probes of the formula (I). More preferred, the compound of the formula (I) is a probe for cathepsin S characterized by a compound comprising the following preferred scaffolds A:

64

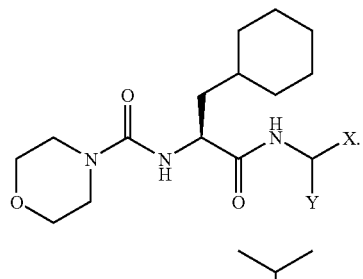

65

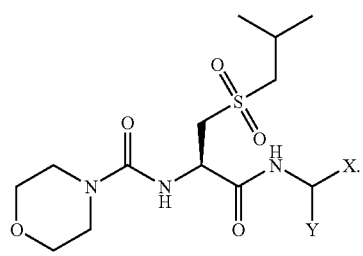

66

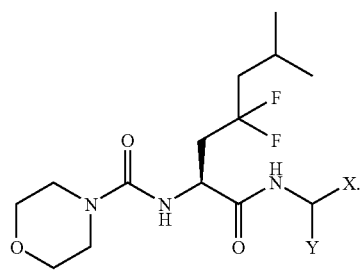

67

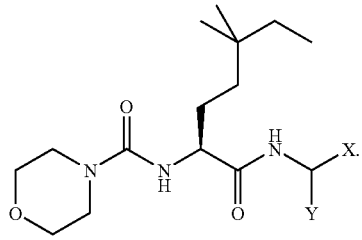

68

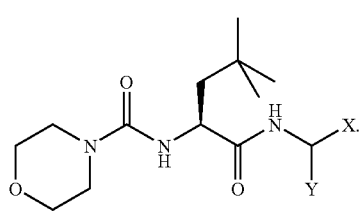

69

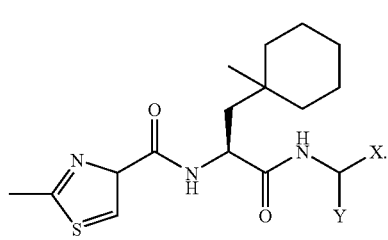

70

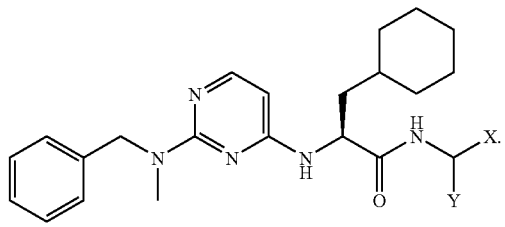

71

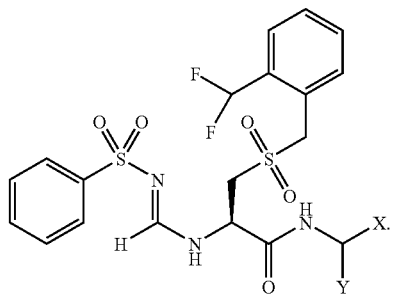

72

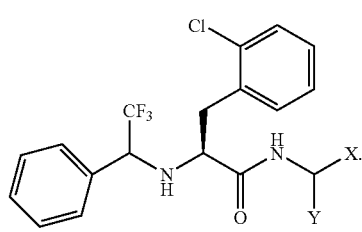

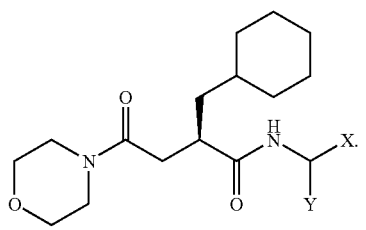
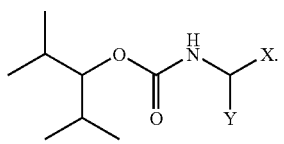
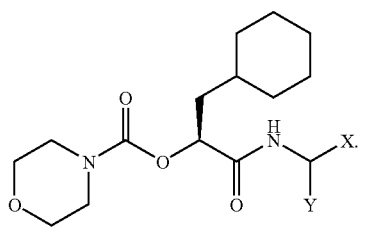
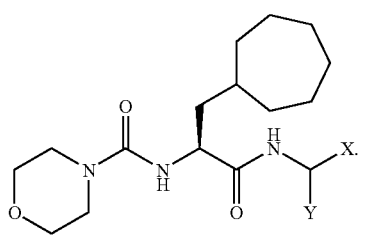
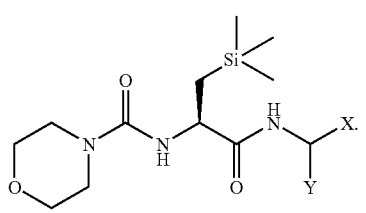
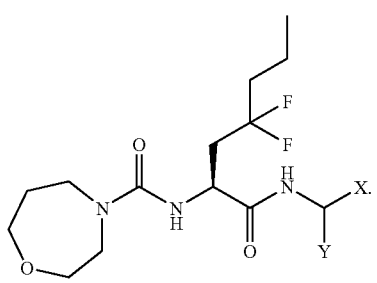
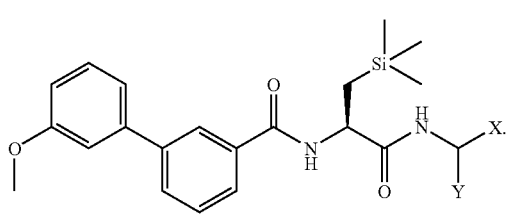
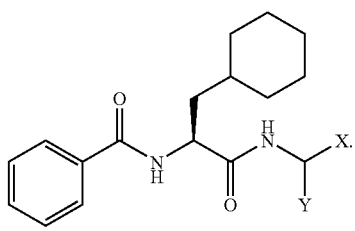
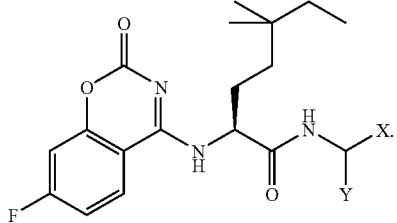
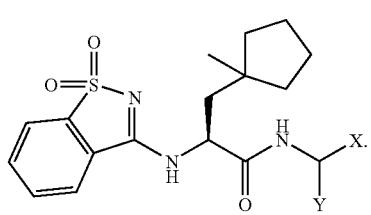
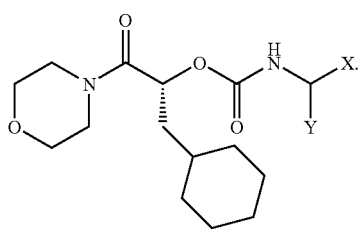
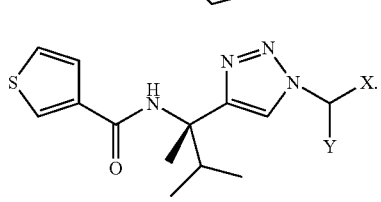
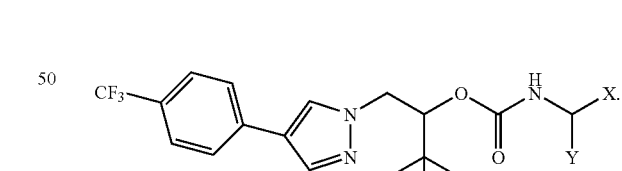
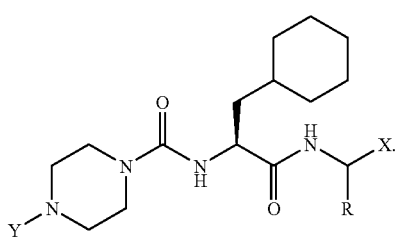

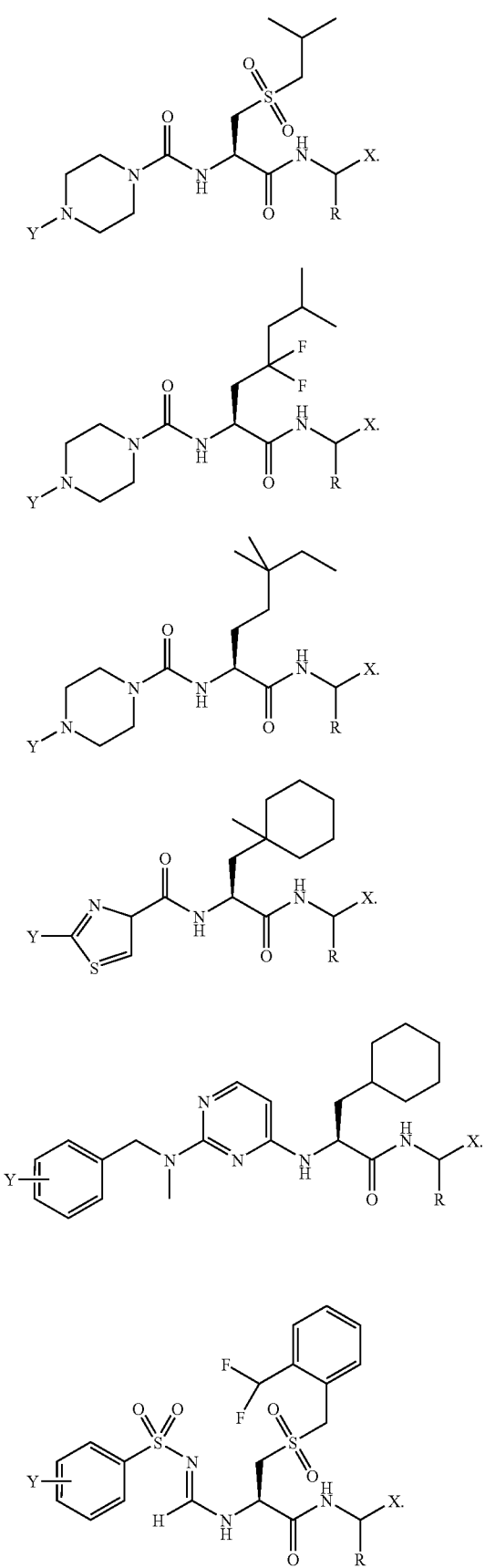
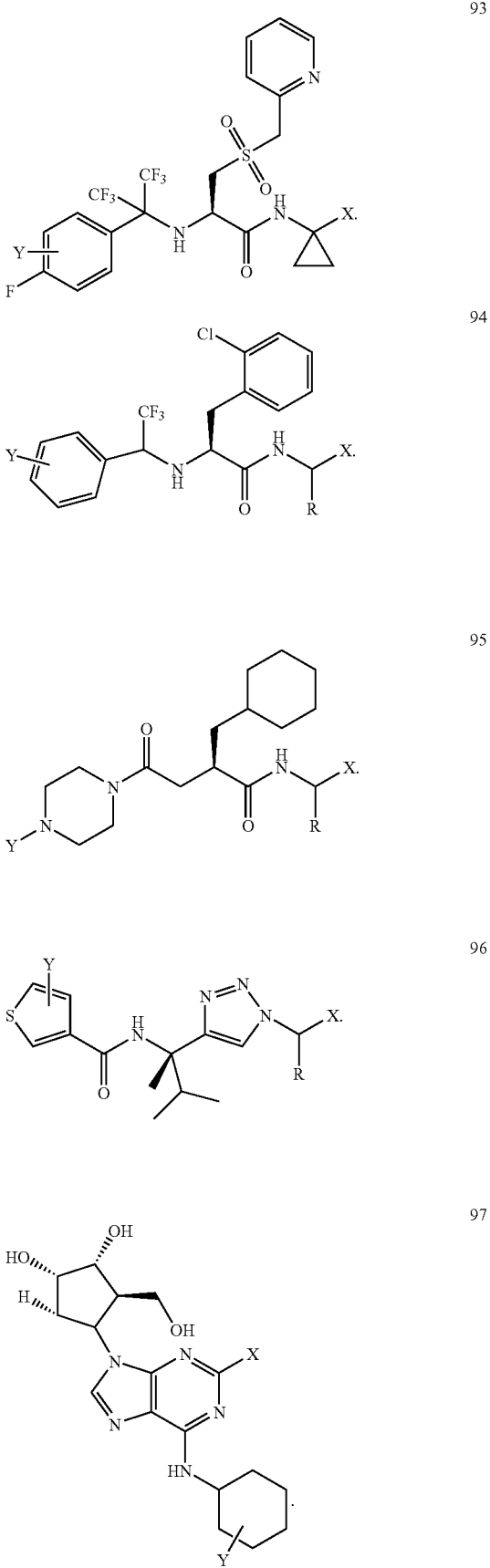

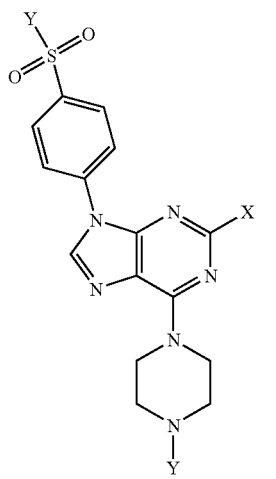
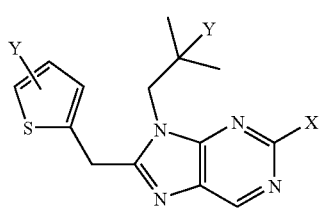
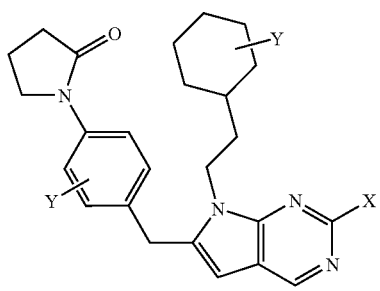
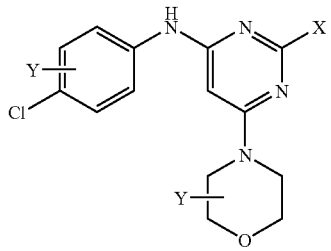
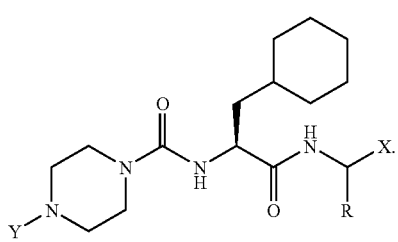
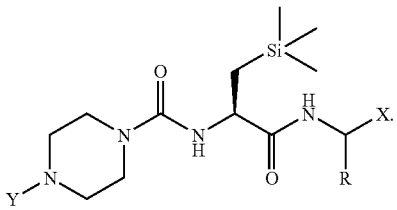
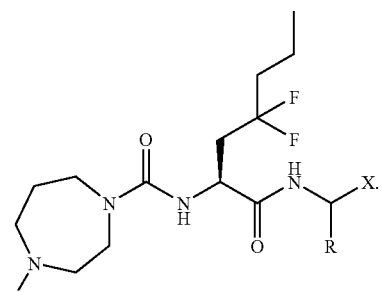
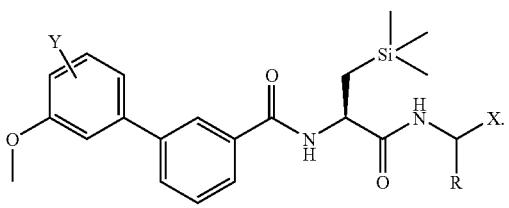
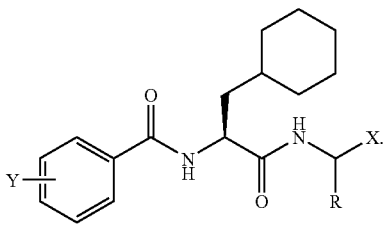
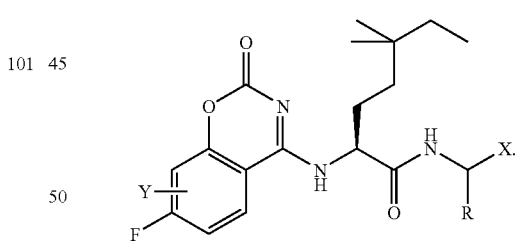
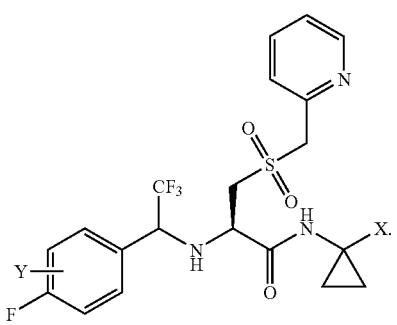

109 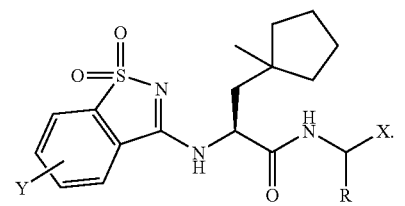

110 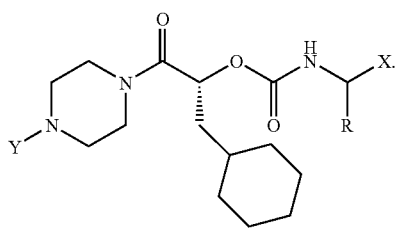

111 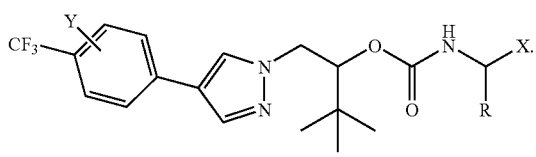

112 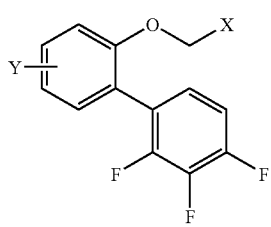

113 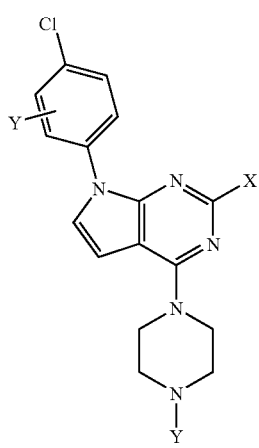

114 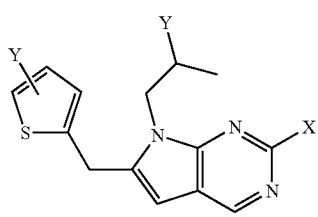

115 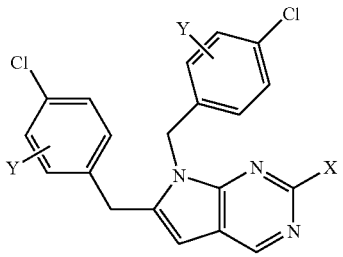

116 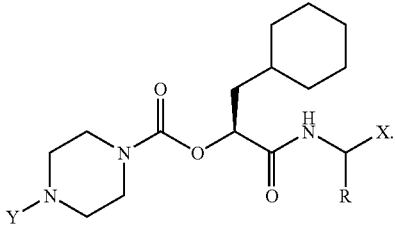

117 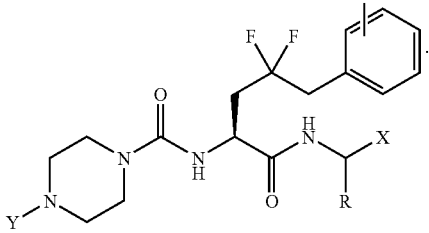

118 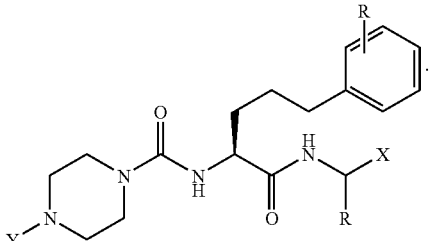

119 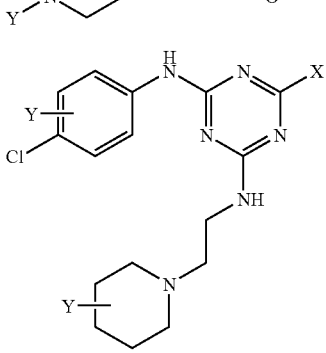

wherein
X is —CONH—R2-L2,
Y is {L-R1-L1}$_n$,
R1, R2, L, L1, L2 and n are as described above, and
R is H, $C_1$-$C_6$-Alkyl.

Compounds 64.-85. are substrates for cathepsin S with L1 in the S1 pocket, compounds 86.-119. for cathepsin S with L1 in the S3 pocket or beyond (outward).

The imaging probes of the present invention may be synthesized by using appropriate protecting group chemistry known in the art to build up the central scaffold A and to attach either linker and label 1 or 2 to this unit via a group L and a group —C(O)—NH—. Appropriate building blocks as well as FRET-pairs such as the cyanine-dyes (e.g. Cy3 B, Cy 5.5, Cy 7) are commercially available (e.g. Sigma-Aldrich, GE-Healthcare). For a subset of probe, descried in this invention, the solid-phase synthesis method is particularly useful (B. J. Merrifield, Methods in Enzymology 1997, 289, 3-13). Depending on the synthetic requirements, attachment linker, quencher or fluorophore may be done on the solid support or by solution phase chemistry.

In general, reactive side chain residues on the central scaffold A and optionally the group L will be protected and liberated sequentially for further modification with the subunits L1R1 and L2R2 respectively. Conjugation of these subunits can be accomplished by known methods of chemical synthesis. Particular useful is the reaction between a dye active ester and a primary amine group of the scaffold A to connect both units via an amide bond. Intermediates as well as final probe molecules may be purified by high performance liquid chromatography (HPLC) and characterized by mass spectrometry and analytical HPLC before they are used in labelling and imaging experiments.

The present invention is illustrated in the following paragraph by several but non-limiting examples:

In a preferred embodiment, the probe of the formula (I) comprises a scaffold A which is derived from a dipeptide cathepsin S inhibitor as shown as No. 64 above and as disclosed in WO2005/082876 bearing a chromophore in the P1 position and in the P1-primed position. Appropriate chromophores are chosen in a way that their spectral properties are suitable for fluorescence resonance energy transfer (FRET). Chromophores can be fluorescent or non fluorescent. In principle, a broad variety of chromophores may be used in the present invention, as long as the central requirement that is a spectral change after proteolytic cleavage of a peptide bond is met. The attachment of such interacting chromophores and the central scaffold is made optionally via linker units.

Preferably, the fluorophore are chosen from the group of xanthene- or cyanine dyes. More preferred are cyanine dyes from the group of carbacyanines, thiacyanines, oxacyanines and azacyanines. Cyanine dyes suitable to be used in the context of the present invention are disclosed in U.S. Pat. Nos. 5,268,468 and 5,627,027. They include the dyes with the trademark (Amersham, GE Healthcare) Cy 3, Cy 3B, Cy 3.5, Cy 5, Cy 5.5, Cy 7 and Cy 7.5.

Preferably, the quencher unit is a non-fluorescent chromophore which include 2,4-dinitrophenyl, 4-(4-dimethylaminophenyl)azobenzoic acid (DABCYL), 7-methoxy-coumarin-4-yl)acetyl and non fluorescent cyanine-dyes as described in WO 9964519.

In a preferred embodiment, the quencher does not show a significant emission and more preferably is a non-fluorescent chromophore. In this embodiment, the imaging reagent comprises a fluorophore and a non-fluorescent (dark) acceptor chromophore. More preferred is a probe, based on a cathepsin S specific scaffold bearing a BHQ3-Quencher in the P1 position and a CY 7 fluorophore in the P1-primed position (Abb.2).

More preferred is a probe of the formula (I) based on a morpholine dipeptide scaffold bearing a QSY 21-Quencher in the P1 position and a CY 5.5 fluorophore in the P1-primed position (Scheme 2):

(Scheme 2)

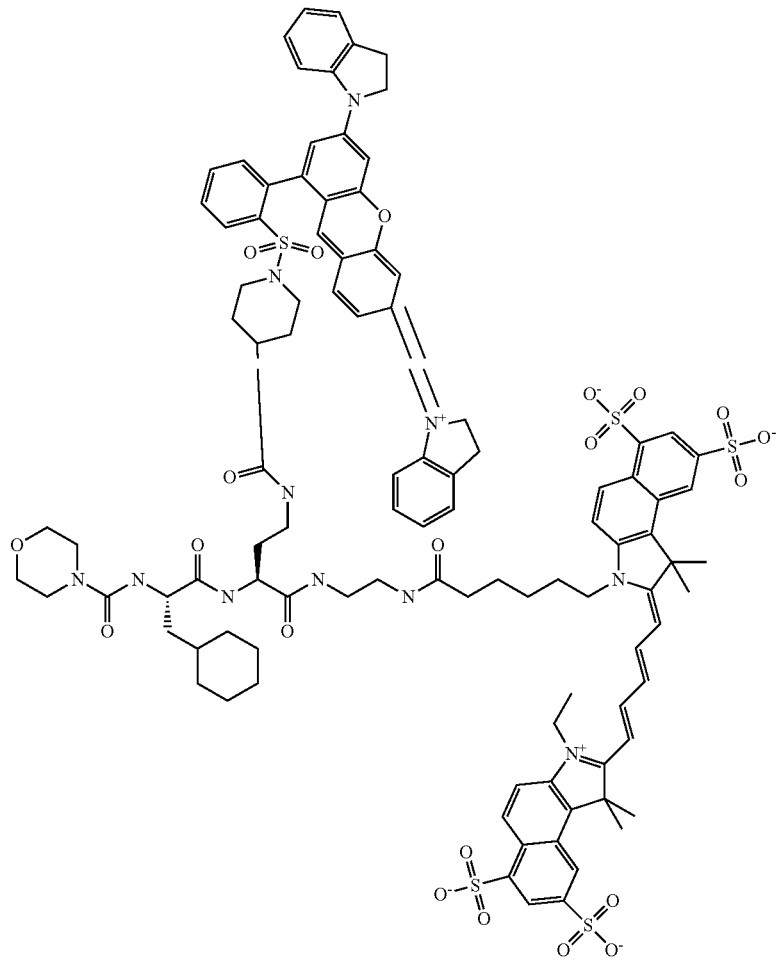

A further preferred embodiment includes the same scaffold bearing the dark quencher BHQ 3 in P1 and a Cy 7 fluorophore in the P1-primed position (Scheme 3).

(Scheme 3)

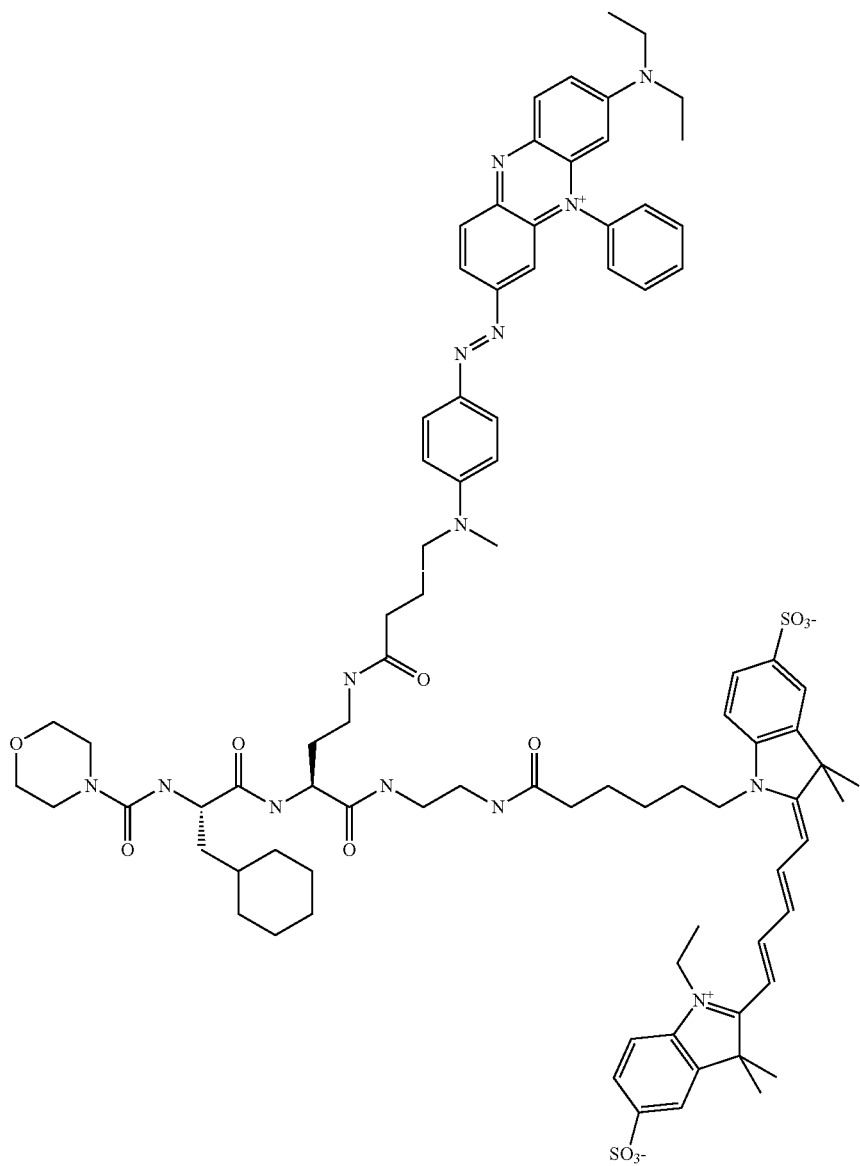

In a further preferred embodiment, a benzamide dipeptidic scaffold A for cathepsin S as disclosed in WO9924460 is converted into an imaging probe by placing the quencher molecule QSY 21 in P1 and the fluorophore CY 5.5 in the P1-primed position (Scheme 4):

(Scheme 4)
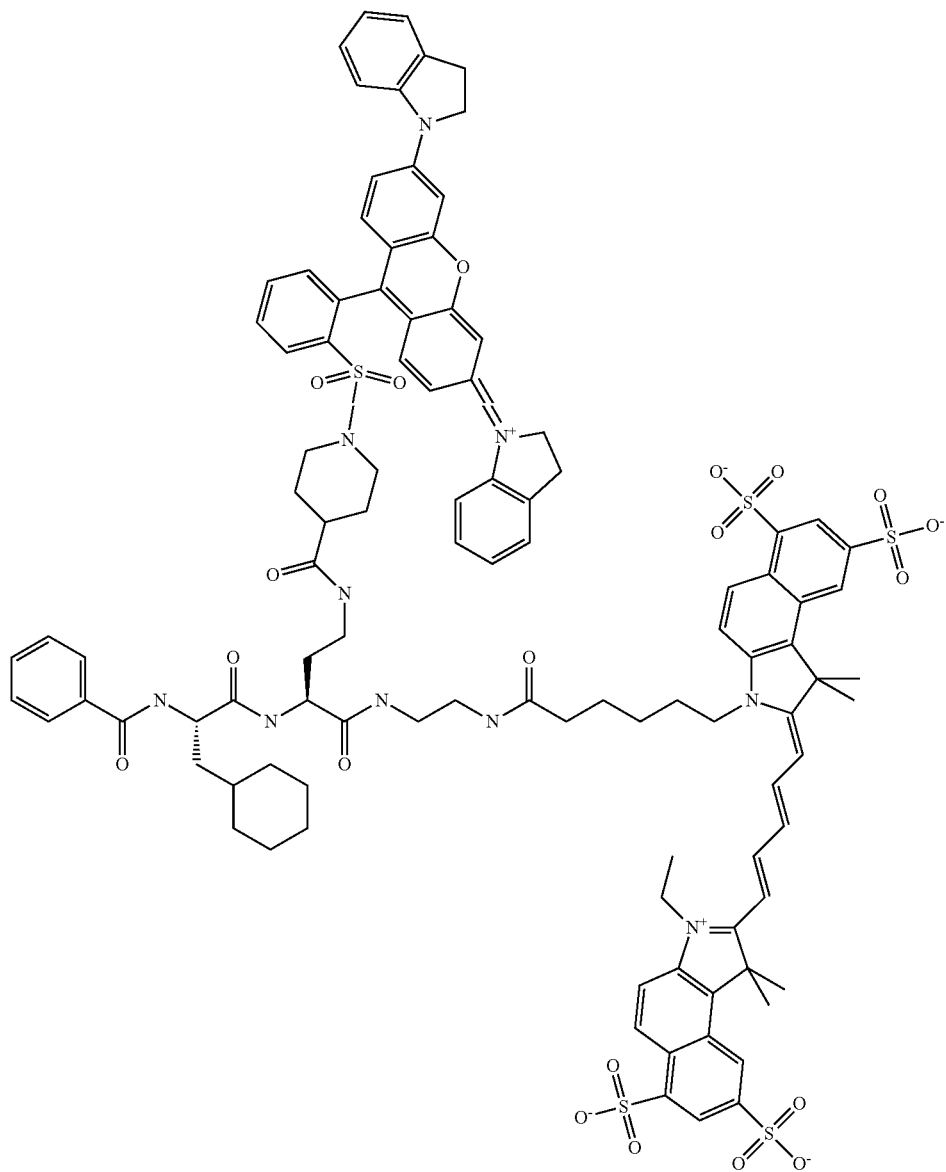
60
In a further preferred embodiment, the above-described benzamide dipeptide scaffold is modified and the quencher QSY 21 is placed in a position corresponding to P3 (Scheme 5).

(Scheme 5)
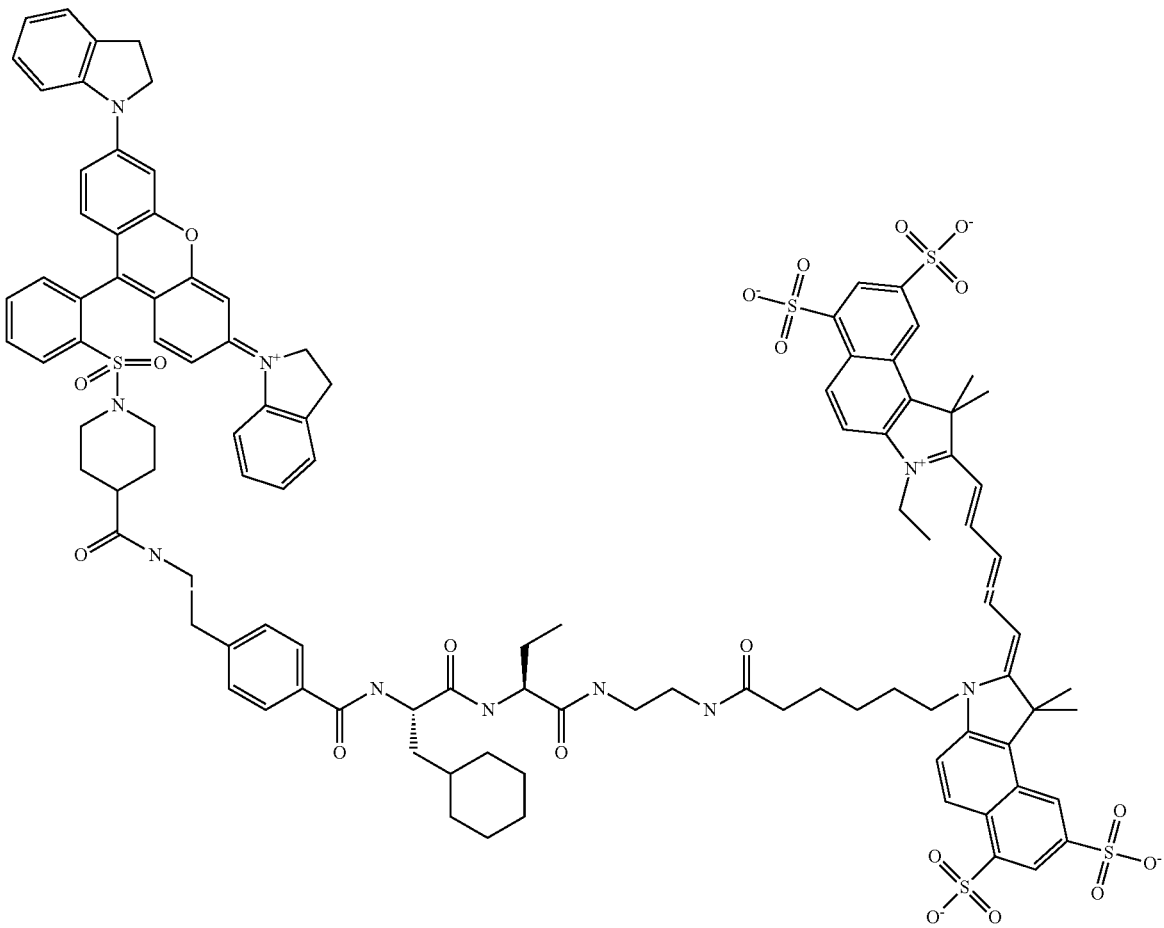
Further preferred is a probe, based on a cathepsin S specific benzamide scaffold bearing a non-fluorescent BHQ 3 quencher in the P1 position and a CY7 fluorophore in the P1" position (Scheme 6).
(Scheme 6)
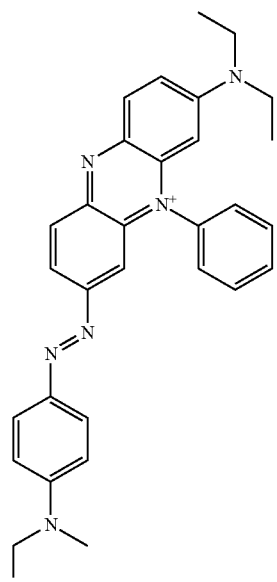

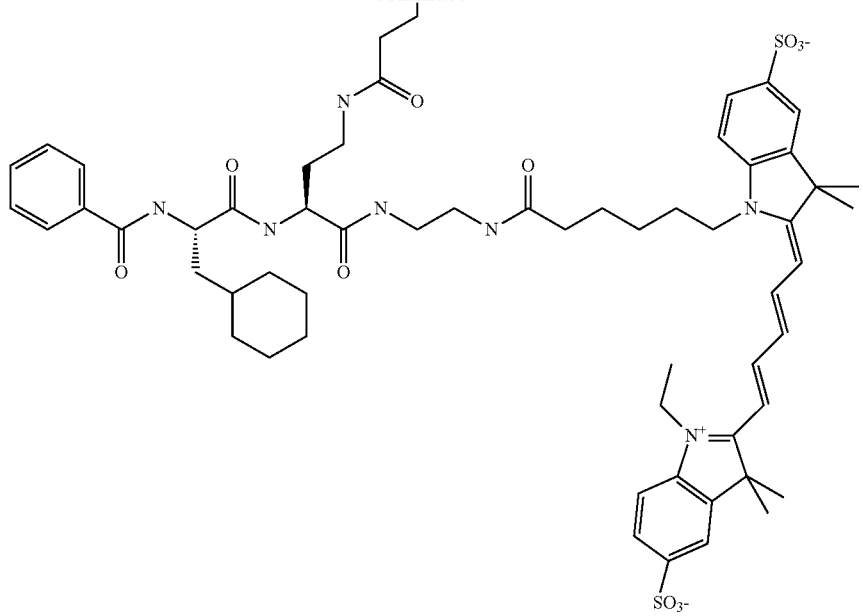
In a further preferred embodiment, the above-said benzamide scaffold is modified and the non-fluorescent BHQ 3 quencher is placed in a position corresponding to P3 (Scheme 7).
(Scheme 7)
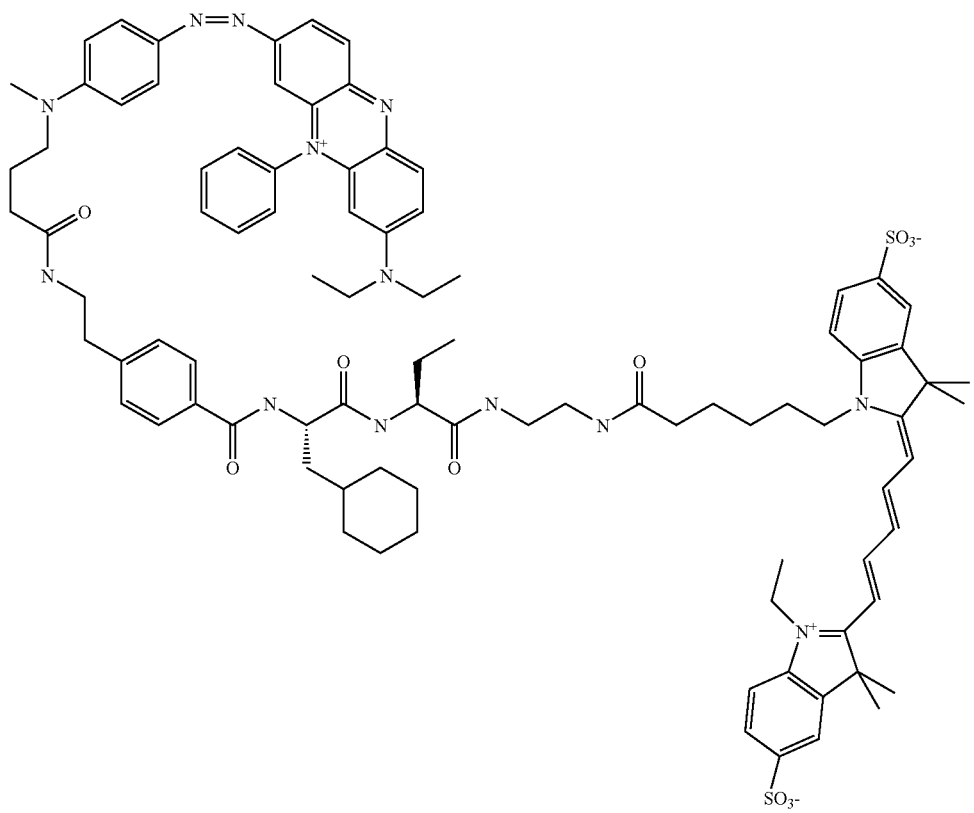

Specific imaging probes for cathepsin K are build up in a similar way than the cathepsin S probes described above.

In a further preferred embodiment, the probe of the formula (I) comprises as a group A piperazine based scaffold which is derived from a cathepsin K inhibitor as disclosed in WO2005049028 and as shown as No. 1 above, bearing a chromophore in the P1 position and in the P1-primed position.

In a preferred embodiment, fluorescein and tetrametrhylrhodamine are chosen as an interacting FRET pair and the tetramethylrhodamine is placed in the P1 position of the scaffold whereas the fluorescein is linked via the P1-prime site as shown in Scheme 8:

(Scheme 8)

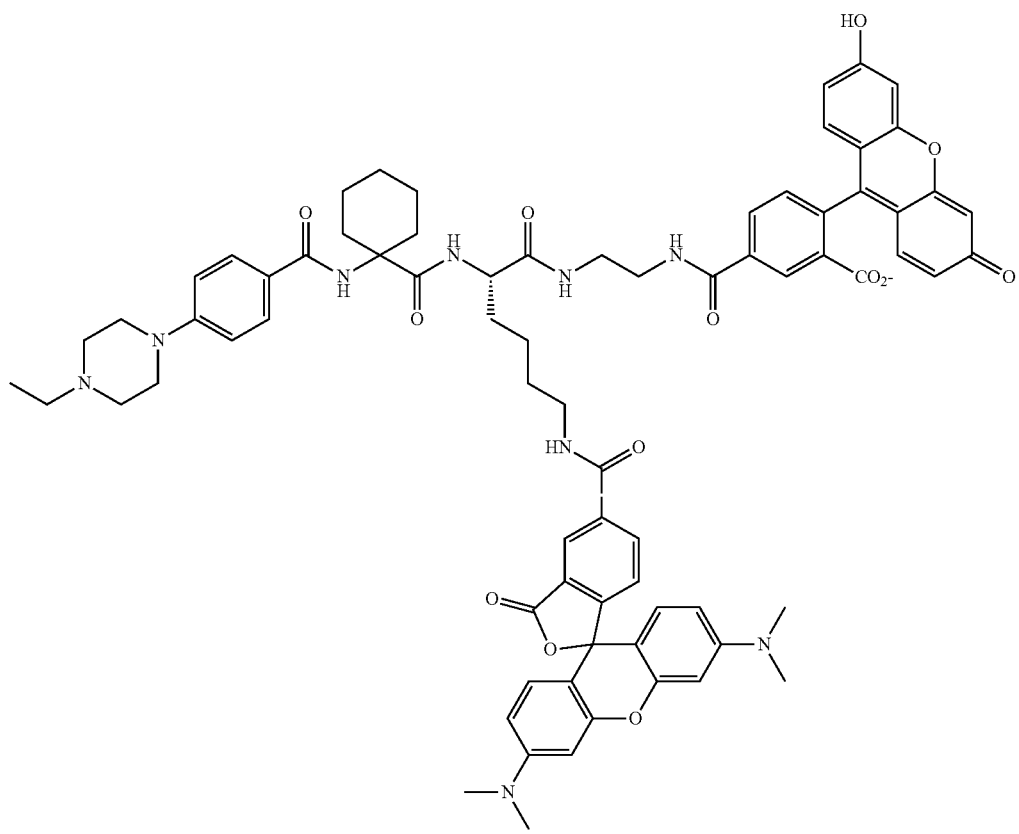

In a preferred embodiment, the quencher does not show a significant emission and more preferably is a non-fluorescent chromophore. In this embodiment, the imaging reagent comprises a fluorophore and a non-fluorescent (dark) acceptor chromophore. More preferred is a probe of the formula (I) based on a cathepsin K specific scaffold bearing a BHQ 3 quencher in the P1 position and a CY 7 fluorophore in the P1-prime position as outlined in Scheme 9:

(Scheme 9)
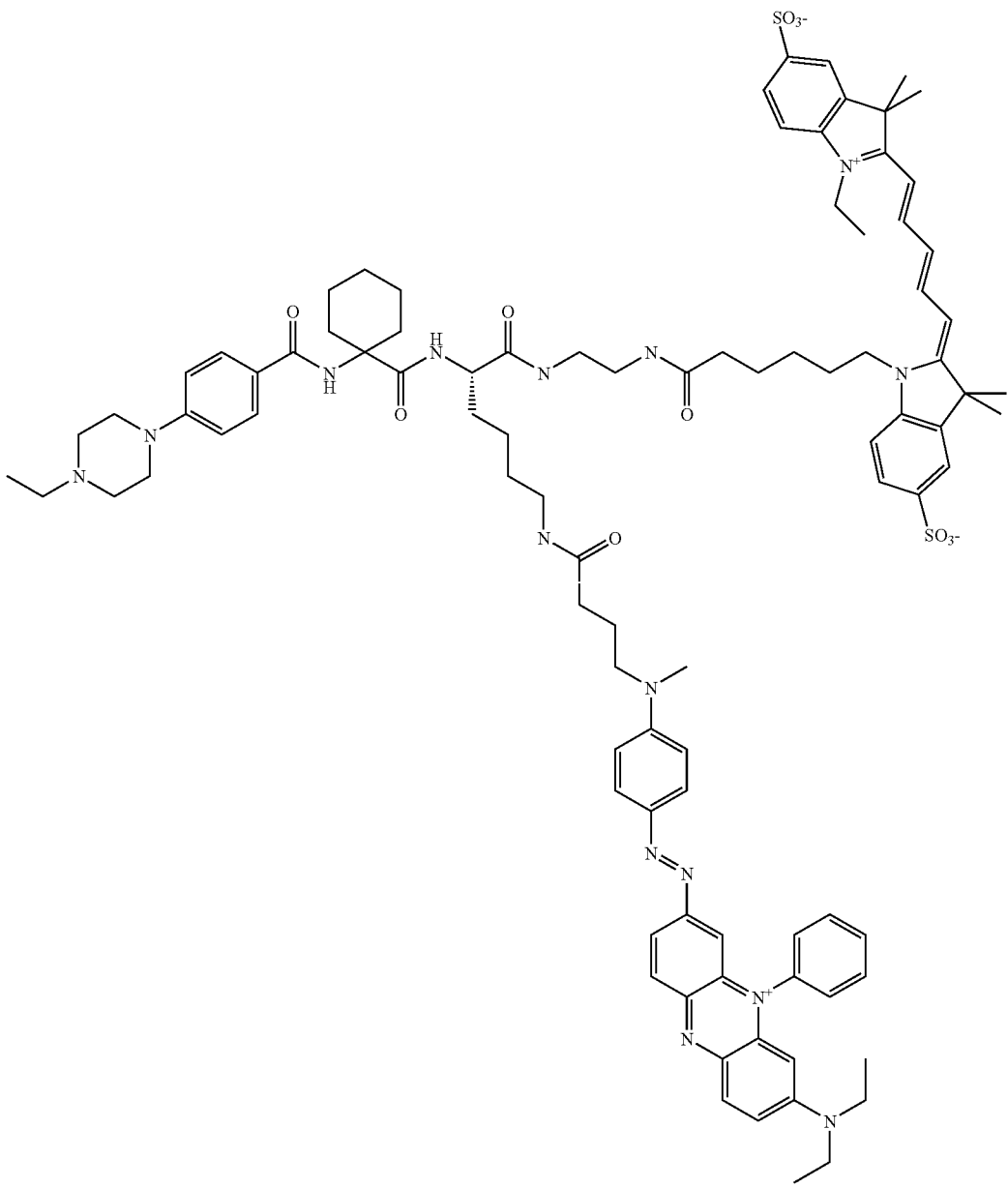
Based on the piperazine-scaffold, a further preferred embodiment comprises a cathepsin K probe of the formula (I) wherein the quencher molecule is placed at the P3 position of the scaffold whereas the corresponding fluorophore Cy 5.5 remains in P1-prime (Scheme 10):

(Scheme 10)
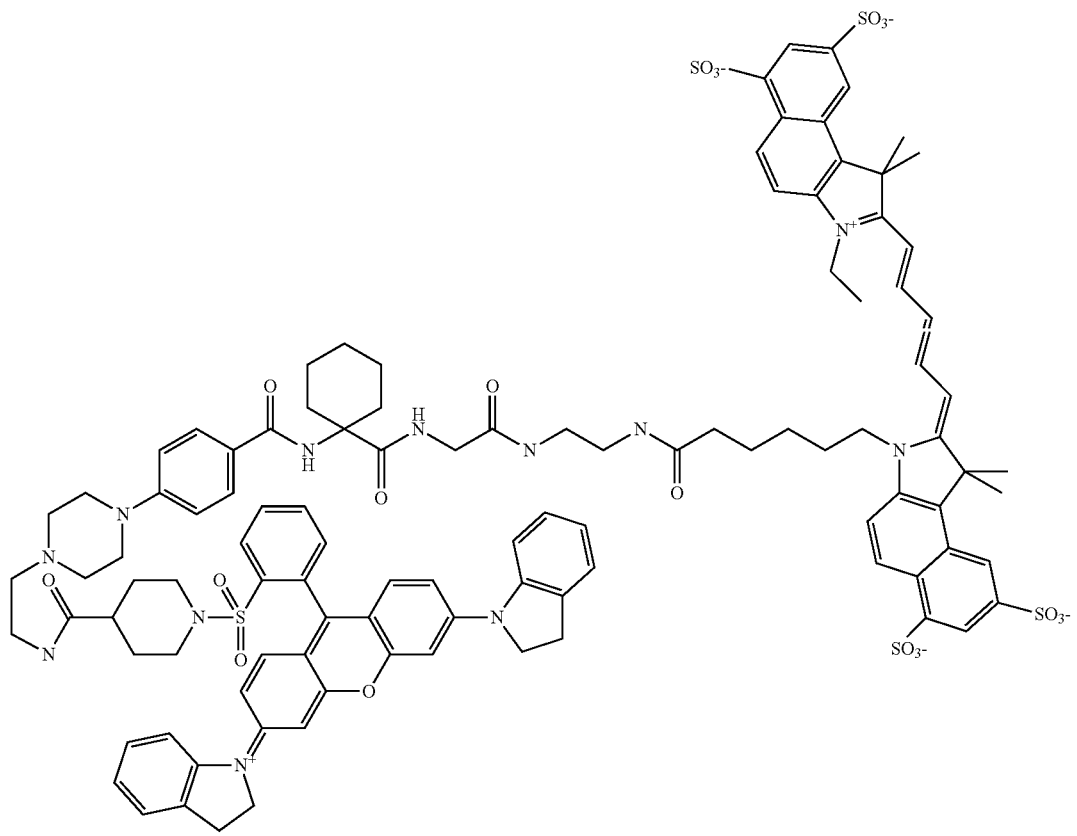
In a further preferred embodiment, the quencher unit of a cathepsin K probe comprise of the non-fluorescent BHQ 3 quencher in the P3 position and the corresponding fluorophore Cy 7 in P1-prime (Scheme 11):
(Scheme 11)
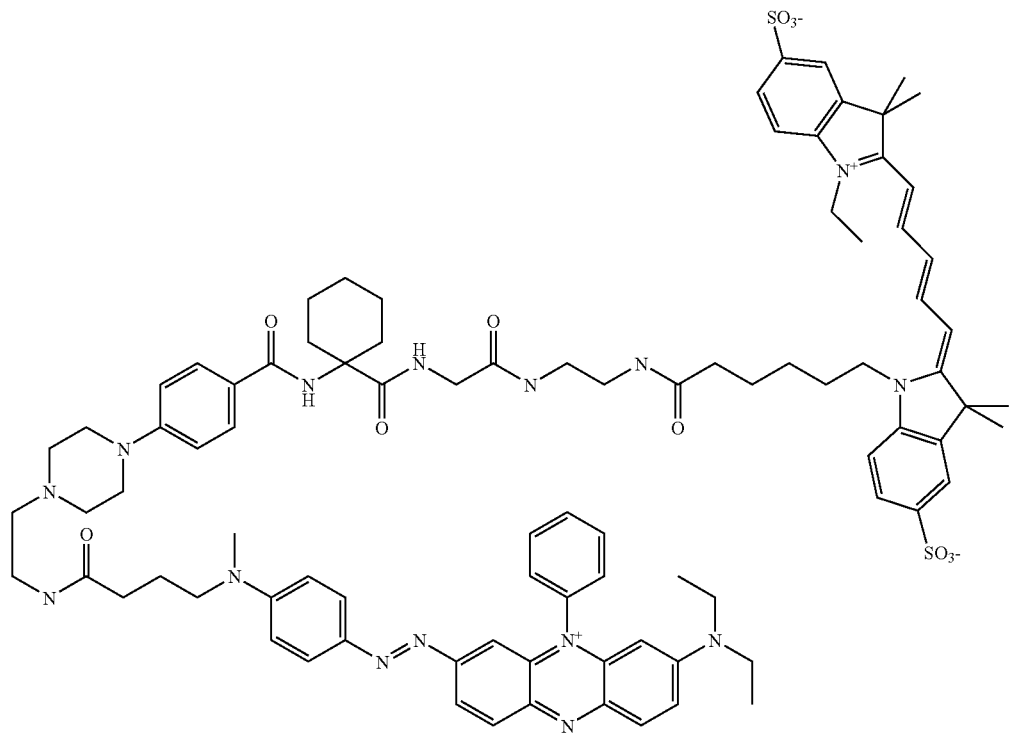

A further preferred embodiment is a probe for cathepsin K comprising a thiazole (disclosed in U. Grabowska et al., Curr. Opin. Drug Disc. 2005, 8, 619-630) as scaffold A. Thus, a further preferred compound of the formula (I) for imaging of cathepsin K activity comprises a quencher in the P1 position of the thiazole scaffold and the fluorophore Cy 5.5 in the P1-prime site (Scheme 12):

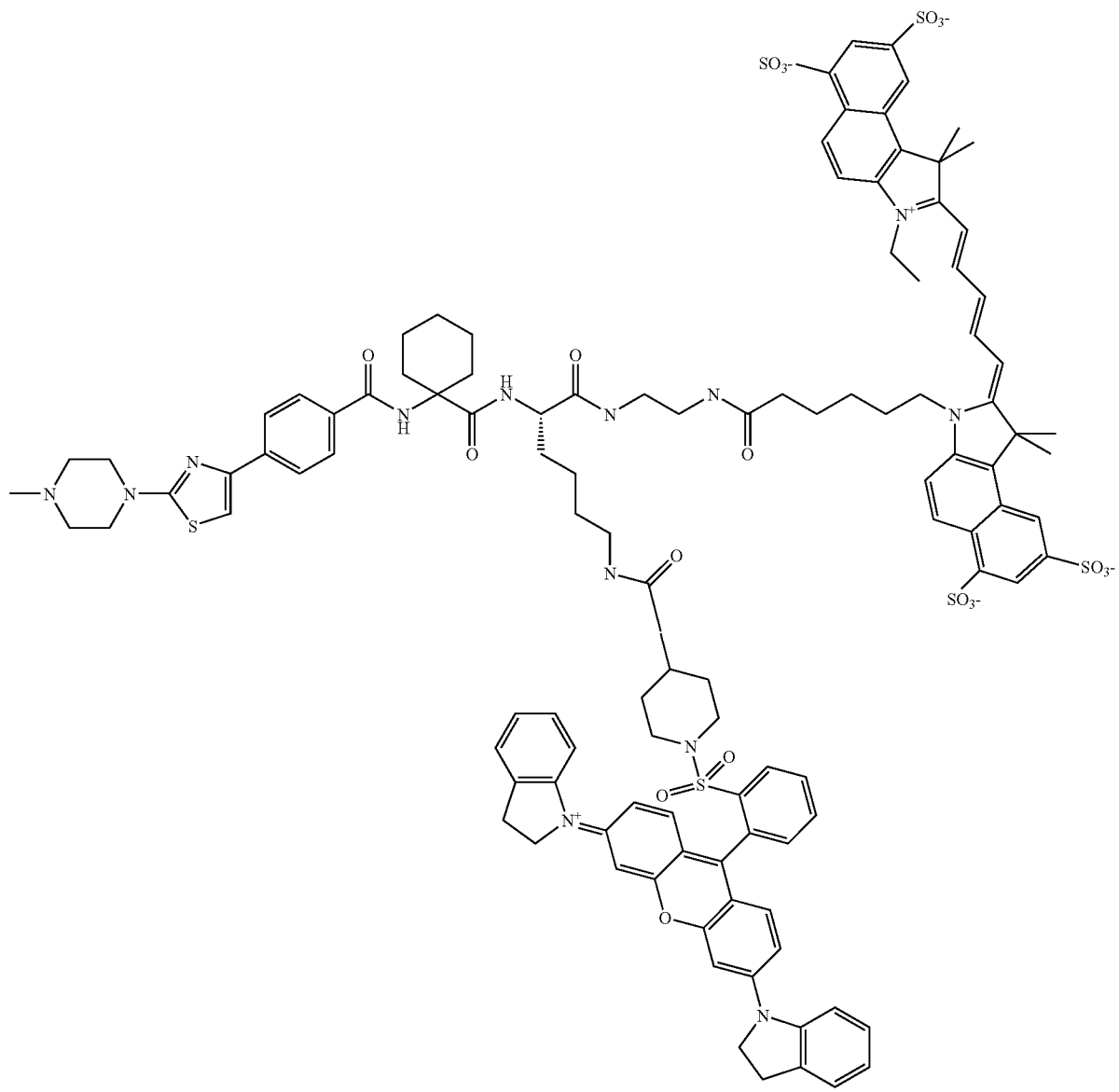

(Scheme 12)

The same design principle applies for the cathepsin K probe, where a non-fluorescent quencher molecule BHQ 3 is used in the P1 position and the fluorophore CY 7 is attached via the P1-prime position (Scheme 13):

(Scheme 13)

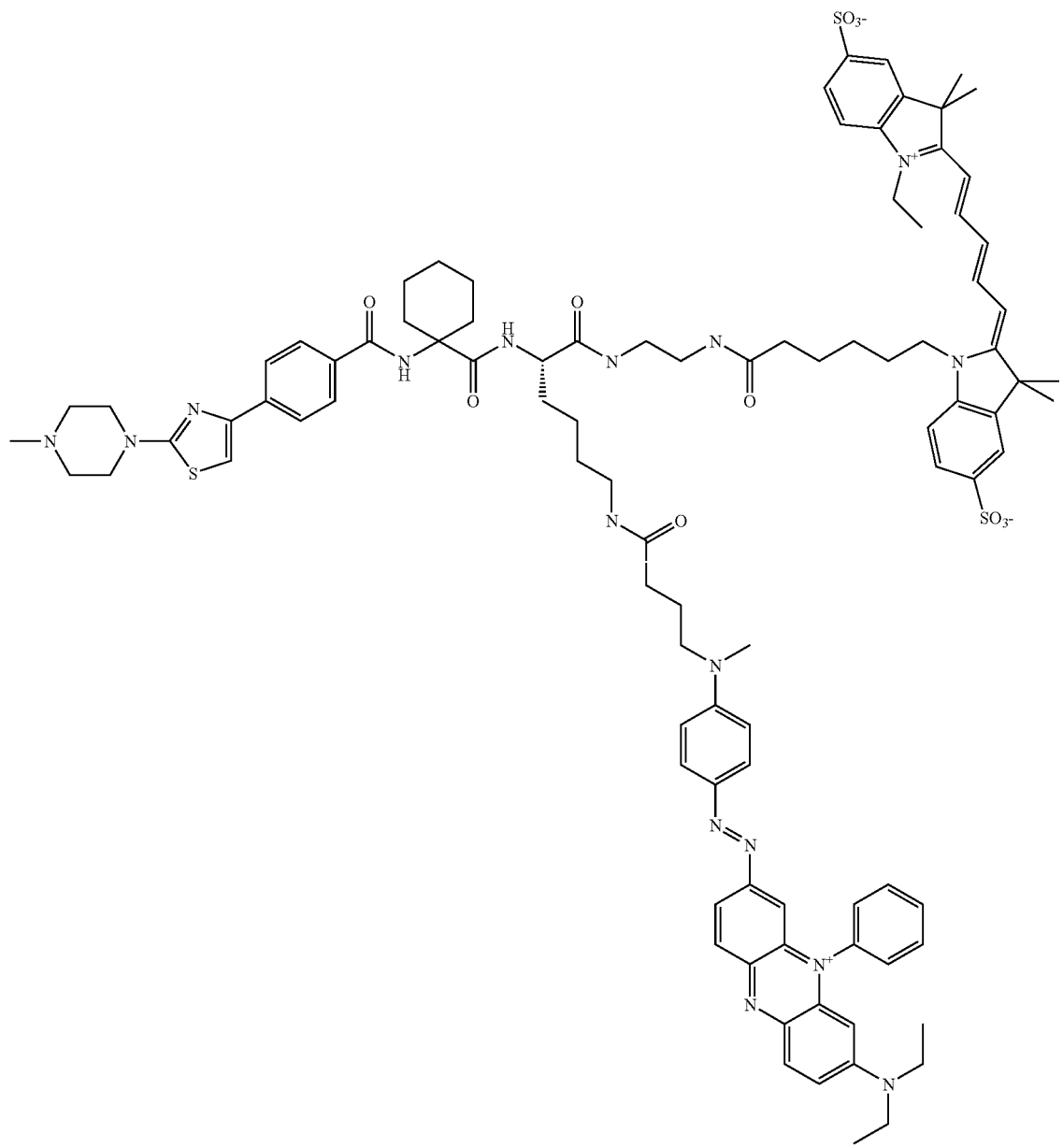

In a further preferred embodiment, one interaction partner of the FRET-pair comprises a nanoparticle. More preferred in the context of the present inventions are CdSe nanoparticles (e.g. Quantum-dots) and lanthanide-ion doped oxide nanoparticles (e.g. Y0.6Eu0.4VO4). If such nanoparticles are used as a donor in a FRET pair, they can be excited at wavelength much shorter than the acceptor absorption thus minimizing direct acceptor excitation. In addition, the narrow donor emission does not overlap with acceptor emission. Furthermore, such nanoparticles proved to be much more photostable than organic dyes which undergo fast photobleaching. Activated quantum dots are commercially available (Invitrogen, Molecular probes) and their emission wavelength can be chosen from a variety of products.

Schemes 14 and 15 show quantum dot based probes of the formula (I) that are specific for cysteine cathepsin S. Thus, in a further preferred probe of the formula (I) the quantum dot (QD605) might be positioned via an appropriate linker either in P1 of the cathepsin S probe (Scheme 14)

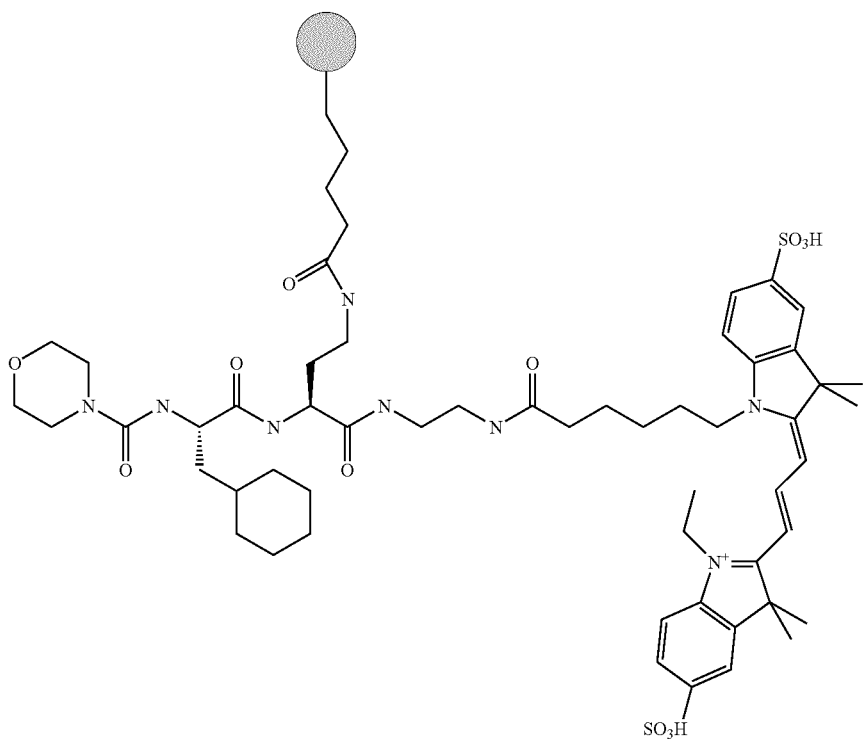
(Scheme 14),
or the P1-prime position (Scheme 15)
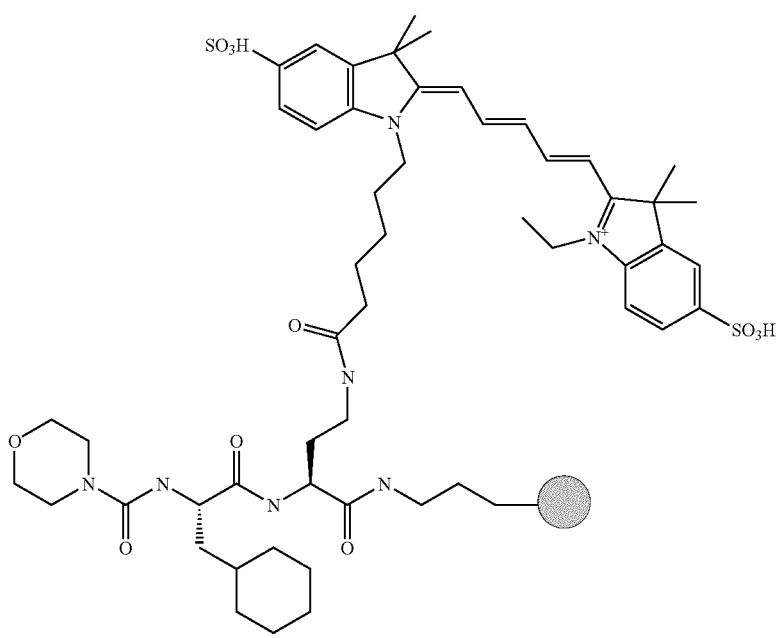
The quantum dot is represented as a grey circle and an appropriate acceptor molecule is represented by the cyanine dye CY 7.
In a further preferred embodiment, the quantum dots in the probe of the formula (I) are connected to gold-nanoparticles via a proteolytic cleavable subunit (Scheme 16):

(Scheme 16)

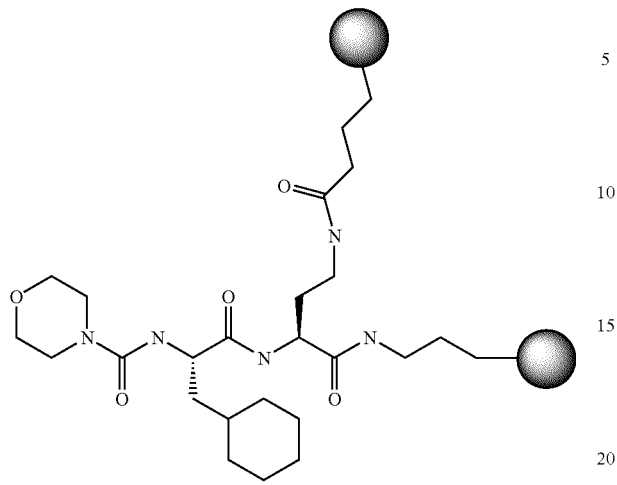

Gold nanoparticles (AuNPs) have been shown as effective quenchers for organic fluorescent dyes as well as for quantum dots. The application of quantum dots in combination with AuNPs is e.g. disclosed in WO2006126570.

In a further preferred embodiment, the probe of the formula (I) consists of a multi-FRET system wherein two specific protease probes are covalently linked together (Scheme 17):

(Scheme 17)

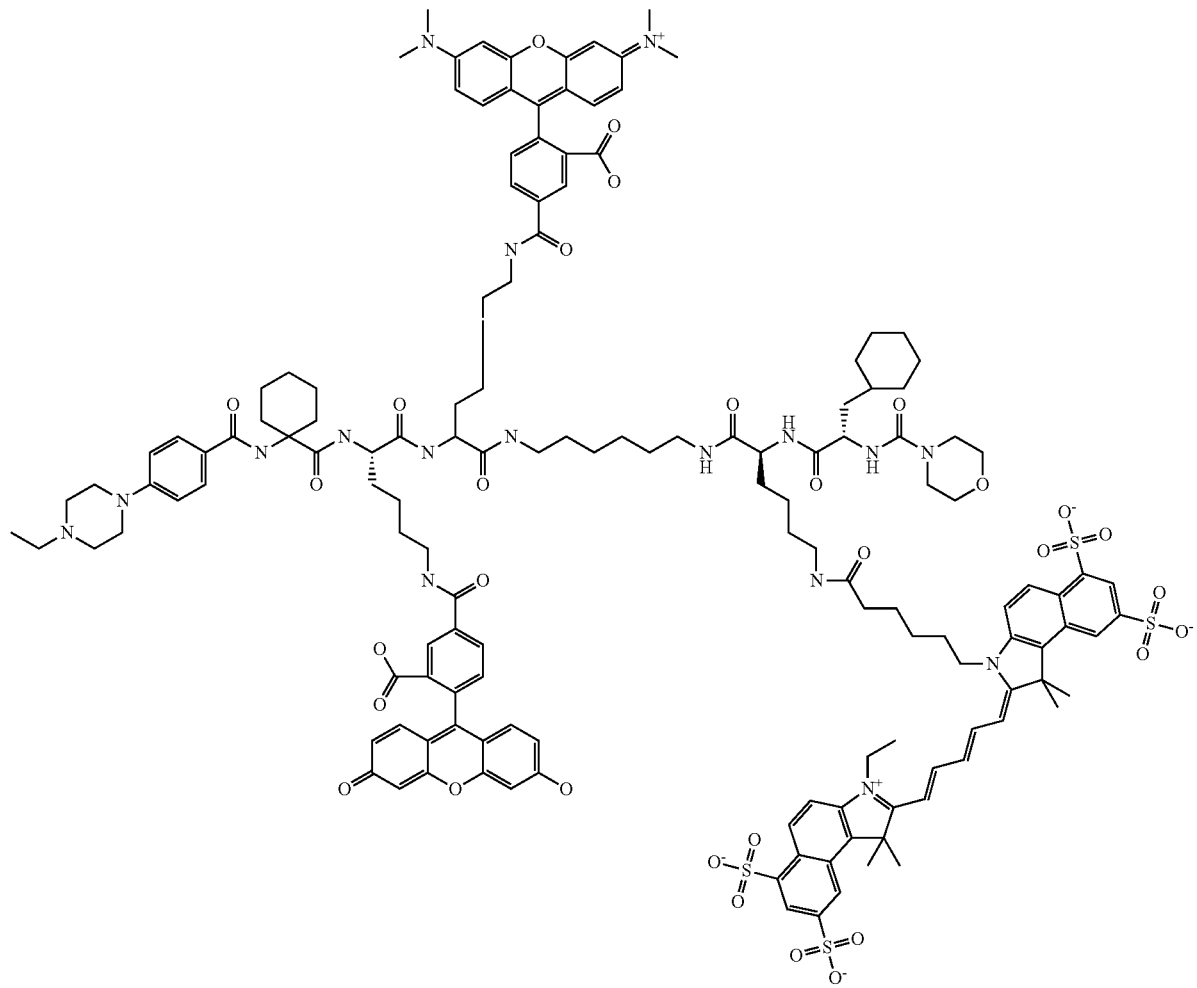

In this configuration it is possible to excite at a single wavelength and use the different emission ratios as unique FRET signatures. (see K. E Sapsford et al. Angew. Chem. Int. Ed. 2006, 45, 4562-4588). This probe combines two specificities in one molecule that is a scaffold for cathepsin K and a scaffold for cathepsin S.

The arrangement of a cathepsin K probe preferably used in the context of compounds of formula (I) wherein two subgroups A (specific for cathepsin K) are derivatized with a dark quencher BHQ-3 and covalently connected to the same fluorescent dye (e.g. Cy 7) is shown in Scheme 18:

high tumoral accumulation and contain quenched fluorescent markers which become fluorescent in the near-infrared spectrum after enzyme activation. These probes are based on synthetic graft copolymer [partially methoxy poly(ethylene glycol) modified poly-D or L-lysine] onto which multiple NIR fluorochromes were attached to free poly-lysine residues. The fluorescence of these macromolecules are highly reduced, due to internal quenching by the high density and close proximity of the NIR-chromophores.

As an example, Scheme 19 shows a polymer-based cathepsin K probe where the connection of A to the poly-lysine

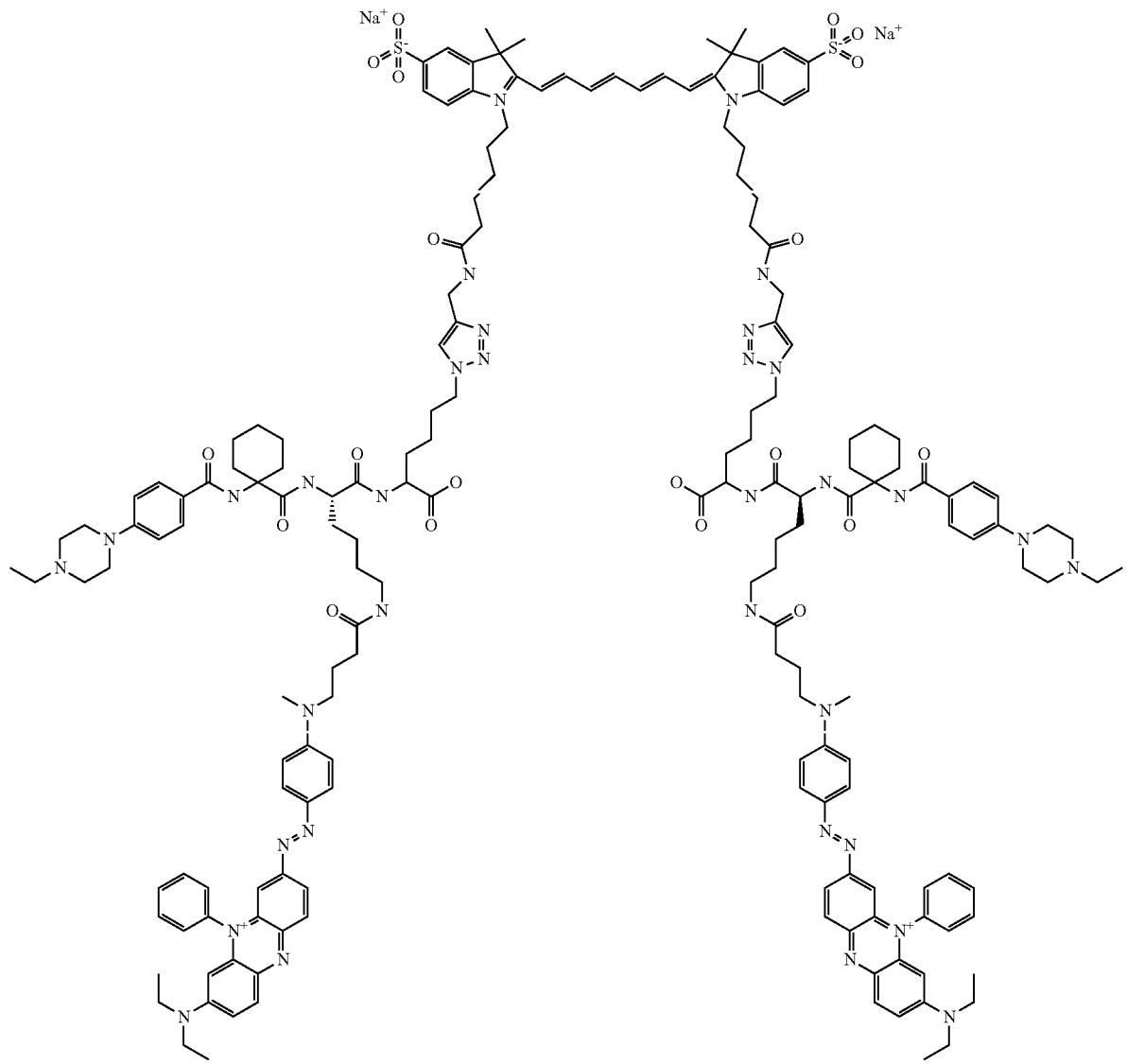

(Scheme 18).

In a further preferred embodiment, the probes of the formula (I) are designed to have a long circulation time, have backbone is achieved via a linker in P1 position whereas the NIR-chromophore Cy 5.5 is attached at the P1-prime site:

(Scheme 19)

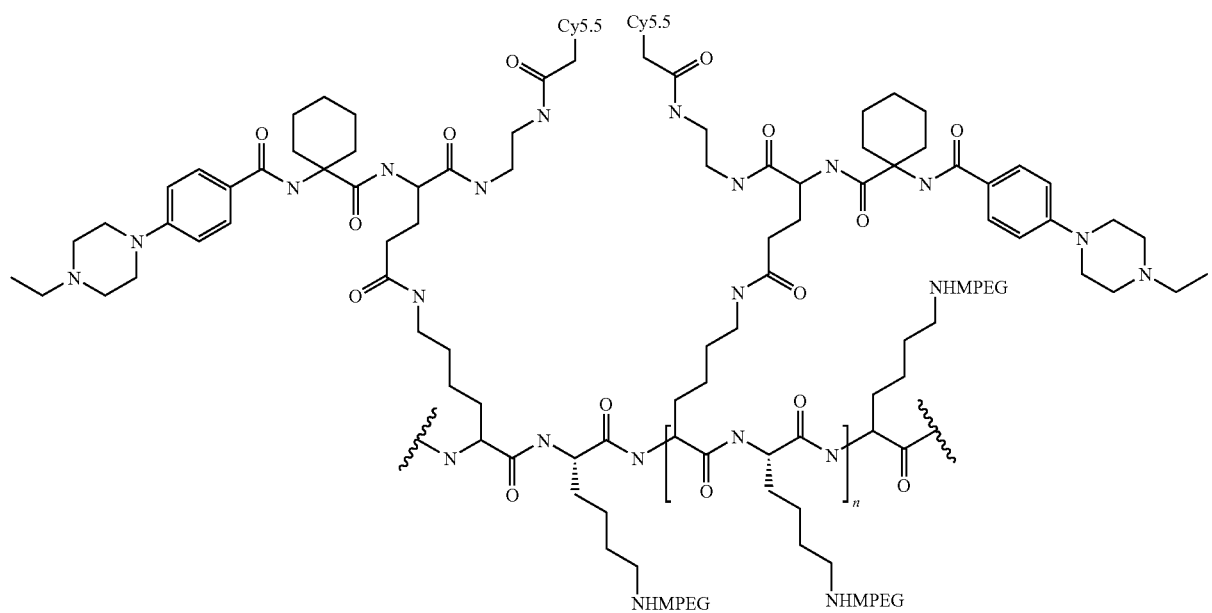

The inverse situation is shown in Scheme 20, where the NIR-chromophore Cy 5.5 is attached at the P1 site whereas the poly-lysine backbone is connected via a linker in P1-prime position:

In a further preferred embodiment, the probes of the formula (I) are designed to be used in an homogeneous enzyme linked luminescence assay. The following scheme shows the above-mentioned mechanism of action generically. The Scheme 20

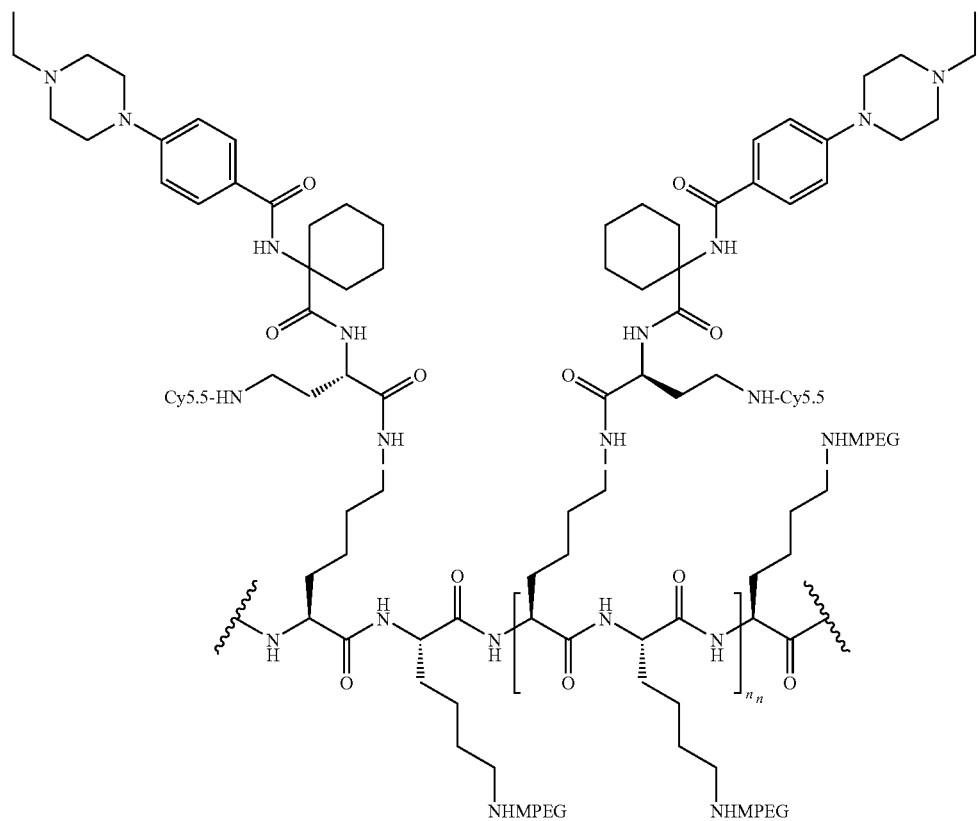

luciferine is a substrate for luciferase and a luminescent signal will be generated by a second enzymatic reaction:

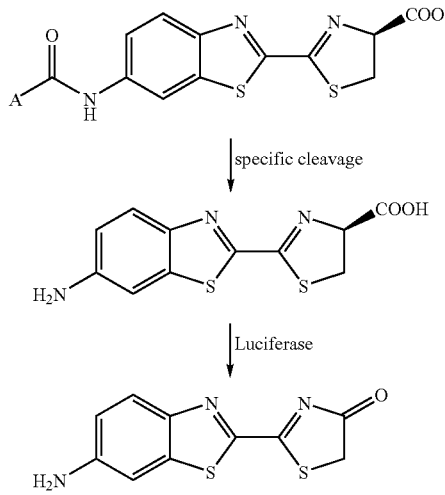

The following scheme shows the above-mentioned mechanism of action, were luciferine is masked with a pyridazino-diazepine-derivative and liberated through the proteolytic activity of said cathepsin K:

thesized in a way that a detectable signal is generated by the enzymatic (e.g. proteolytic) activity of a specific target. Particularly, preferred probes comprise internally quenched fluorophores (e.g. appropriate FRET-pairs) linked to (i) the specificity determinant A at the N-terminal portion of the scissile bond and (ii) at the C-terminal portion of the scissile bond. The invention allows for the transfer elements of desirable and previously optimized properties of known inhibitors into novel activity based probes.

Cathepsin inhibitors described in the prior art utilize a nitrile group. The imaging probes of the present invention make use of said known scaffolds and introduce two modifications, firstly the replacement of the nitrile group by a cleavable amide group and secondly by the positioning of interacting labelling pairs or property modulators on both sides of the amide group.

In vitro, the reaction of the protease with the substrate of the invention can generally be either performed in cell extracts or with purified or enriched forms of the protease. For in vivo application, the reporters are preferably emitters in the near infra red (NIR) region because that region is absent of interfering biofluorescence. Known cyanine NIR dyes matching these requirements are preferably incorporated in the substrates of the present invention.

The molecular architecture of compounds of the formula (I) consist of a central scaffold A bearing an amide functional group and two subunits L1R1 and L2R2 respectively. L2R2

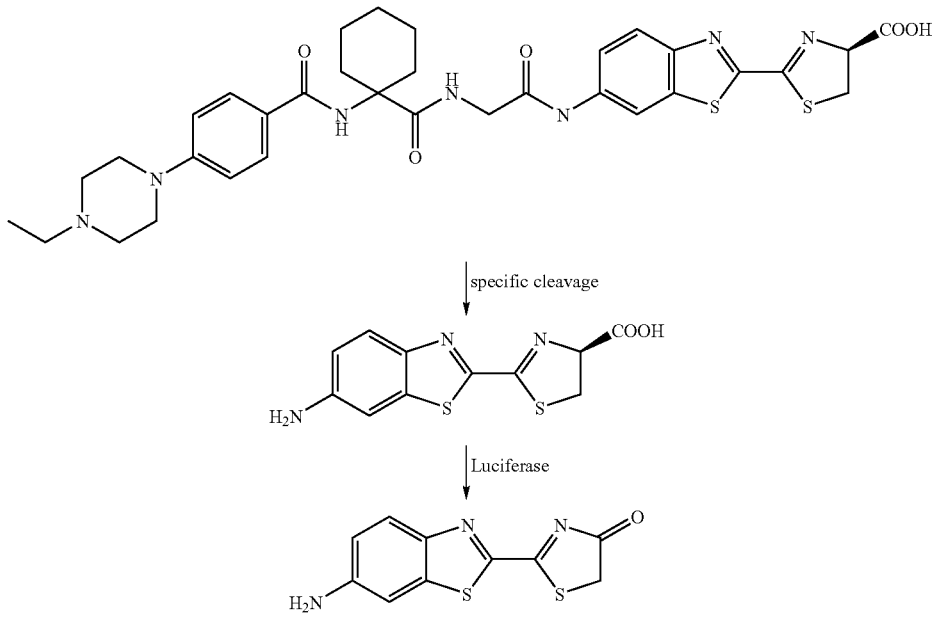

The invention further relates to a method for the design of a molecular probe for the observation of the catalytic activity of individual proteolytic enzymes or groups of proteolytic enzymes, such as e.g. a cysteine cathepsin or cysteine cathepsins, in in vitro assays, in cells or in multicellular organisms, characterized in transforming an inhibitor for an individual proteolytic enzyme or a group of proteolytic enzymes into a selective activity-based probe for these individual proteolytic enzyme or group of proteolytic enzymes, preferably cysteine cathepsin enzymes. To achieve this we replace the electrophilic groups of certain known cysteine cathepsin inhibitors with a scissile peptide bond. Preferred compounds are synis, as shown in formula (I), always connected to scaffold A via an amide group since the amide group can be cleaved by the cathepsin enzyme. Appropriate functional groups for the attachment of subunits L1R1 to scaffold A can be chosen by those skilled in the art, and examples are given below. The specific functional groups L' in the precursor compound can be placed on the scaffold A for the attachment of suitable L1R1 subunits to yield the group L within the compound of the formula (I) are limited only by the requirement of the synthesis strategy and the final use of such substrate as an activity based imaging reagent. Thus their selection will depend upon the specific reagents chosen to build the desired substrates. Examples of functional groups L' which can be provided on scaffold A to connect A with the subunit R1L1 include fluoro, chloro, bromo, cyano, nitro, amino, azido, alkylcarbonylamino, carboxy, carbamoyl, alkoxycarbonyl, aryloxycarbonyl, carbaldehyde, hydroxy, alkoxy, aryloxy, alkylcarbonyloxy, arylcarbonyloxy, a carbon-carbon double bond, a carbon-carbon triple bond, and the like. Most preferable examples include amino, azido, hydroxy, cyano, carboxy, carbamoyl, carbaldehyde, or a carbon-carbon double or a carbon-carbon triple bond. Thus, L is preferably a direct bond or a group selected from

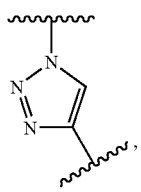 [SMILES: *c1cn(*)nn1]

—(NRx)-, —O—, —C=N—, —C(=O)—, —C(=O)—NH—, —NH—C(=O)—, —C(=O)H, —CRx=CRy-, —C≡C— and phenyl, wherein Rx and Ry are independently H or ($C_1$-$C_6$)alkyl.

In particular, the preferred synthesis of a compound of formula (I) makes use of orthogonally protected functional groups. Such a choice of protective groups allows for a separate deprotection so that each released functionality in turn can be further chemically manipulated towards the attachment of the corresponding subunits to scaffold A. Appropriate protecting groups for the envisioned functionalities can be chosen by those skilled in the art, and are e.g. summarized in T. W. Greene and P. G. M. Wuts in "Protective Groups in Organic Synthesis", John Wiley & Sons, New York 1991.

Compounds of the formula L'-A-CO—OH (scaffolds) can be prepared by standard methods known in the art, e.g. as described in international patent applications WO06076796, WO06076797, WO06063762, WO05049028, WO04089395, WO05040142, WO0055144, WO05074904 and WO0069855.

The present invention also relates to a method for the preparation of a compound of the formula (I) wherein n is 1 characterized in
(a) a compound of the formula (II)

L'-A-CO—OH  (II)

wherein A is as defined above in its generic and preferred meanings and L' is fluoro, chloro, bromo, cyano, nitro, amino, azido, alkylcarbonylamino, carboxy, carbamoyl, alkoxycarbonyl, aryloxycarbonyl, carbaldehyde, hydroxy, alkoxy, aryloxy, alkylcarbonyloxy, arylcarbonyloxy, a carbon-carbon double bond, a carbon-carbon triple bond, preferably amino, azido, hydroxy, cyano, carboxy, carbamoyl, carbaldehyde, or a carbon-carbon double or a carbon-carbon triple bond, more preferred amino,
is reacted under conditions known to a skilled person with a compound of the formula L1-R1-H wherein L1 is as defined above in its generic and preferred meanings to a compound of the formula (III)

L1-R1-L-A-CO—OH  (III)

(b) the compound (III) is reacted with a compound $H_2N$—R2-L2 to a compound of the formula (I).

Optionally, the synthesis of the compound of the formula (I) makes use of orthogonally protected functional groups. Such a choice of protective groups allows for a separate deprotection so that each released functionality in turn can be further manipulated chemically either to attach a label to it or for the introduction of further extension of the linker R1 and/or R2. Appropriate protecting groups for the envisioned functionalities can be chosen by those skilled in the art, and are e.g. summarized in T. W. Greene and P. G. M. Wuts in "Protective Groups in Organic Synthesis", John Wiley & Sons, New York 1991.

A further method for the preparation of the probe of the formula (I) comprises
(a1) the reaction of a compound of the formula (II) with a compound of the formula (IV)

$H_2N$-L2-PG2  (IV)

to a compound of the formula (V)

L'-A-CO—NH—R2-PG2  (V)

under conditions known to the skilled person,
(b) subsequently reacting the compound (V) with a compound (VI)

PG1-R1-L"  (VI)

to a compound

PG1-R1-L-A-CO—NH—R2-PG2  (VI)

under conditions known to the skilled person for the respective groups,
wherein
PG1 and PG2 are independent of each other protecting groups, preferably orthogonally protecting groups,
L" is the respective connecting group for L' to be selected by the person skilled in the art, or bond,
(c1) the group PG2 of the compound (VI) is cleaved and the resulting compound is reacted with a label L2, and subsequently the protecting group PG1 is cleaved and the resulting compound is reacted with a label L1 to a compound of the formula (I), or
(c2) the group PG1 of the compound (VI) is cleaved and the resulting compound is reacted with a label L1, and subsequently the protecting group PG2 is cleaved and the resulting compound is reacted with a label L2 to a compound of the formula (I).

In step (b), preferred combinations of L' and L" and reaction types (in brackets) are as follows:
When L' is fluoro, chloro, bromo, iodo, L" is amino (R—$NH_2$), hydroxy (R—OH), triple-bond (Sonogashira Reaction), a double bond (Heck reaction), an alkyl borane (Suzuki-reaction);
when L' is cyano, L" is amino (R—$NH_2$), hydroxy (R—OH), thiol (R—SH);
when L' is amino, L" is an activated carboxylic acid (NHS-ester, . . . ), an carbaldehyde, fluoro, chloro, bromo, iodo;
when L' is azido, L" is a triple bond, a phosphine moiety (Staudinger ligation);
when L' is carboxy, L" is amino, hydroxyl, hydrazide;
when L' is alkoxycarbonyl, L" is amino, hydroxyl, hydrazide;
when L' is aryloxycarbonyl, L" is amino, hydroxyl, hydrazide;
when L' is hydroxy, L" is fluoro, chloro, bromo, iodo, hydroxy (Mitsunobu-reaction), carboxy;

when L' is carbaldehyde, L" is amino, hydrazine;

when L' is carbon-carbon double bond, bromo, chloro, iodo (Heck reaction), an alkyl borane (Suzuki-reaction);

when L' is a carbon-carbon triple bond L" is bromo, chloro, iodo (Sonogashira Reaction), azido.

Preferably cysteine protease substrates functionalized with different label are synthesized on the solid support. Depending on the compatibility of the label for solid phase synthesis a combination of solid-support and solution-phase synthesis is used.

The preparation of a compound of the formula (I) wherein group A consists of a cathepsin S inhibitor, L1 is a 6-((4,4-difluoro-1,3-dimethyl-5-(4-methoxyphenyl)-4-bora-3a,4a-diaza-s-indacene-2-propionyl)amino)hexanoic acid, residue (tradename: BODIPY-TMR-X, Invitrogen) and L2 is the quencher QSY-7 is further described in Examples 5-8: The scaffold of Example 5 having a C-terminal lysine residue with Boc-protected amino group of the side chain is prepared on the solid-support using the chloro-trityl resin. The obtained C-terminal carboxylic acid is coupled to mono-Fmoc-protected butane-1,4-diamine, which is further modified in solution. After removal of the Boc-group of the lysine side chain by methods known in the art, e.g. by reaction with TFA, a fluorophore (preferably activated as its N-hydroxysuccinimidyl ester) was coupled to the peptide under standard conditions. The coupled intermediate compound may optionally be purified by e.g. preparative HPLC. After removal of the C-terminal Fmoc-group the quencher (preferably activated as its N-hydroxysuccinimidyl ester) was coupled to the peptide and the final product was purified by preparative HPLC.

For the synthesis of several cysteine cathepsin substrates with a peptidomimetic structure non-peptidic building blocks may be utilized for the solid-phase synthesis. Building block syntheses are further described in Examples 20-22,

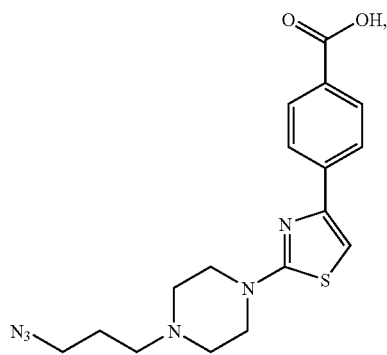
(II)

Examples 23-24,

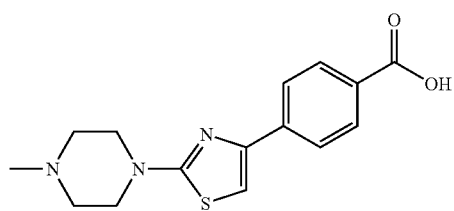
(III)

and Example 17,

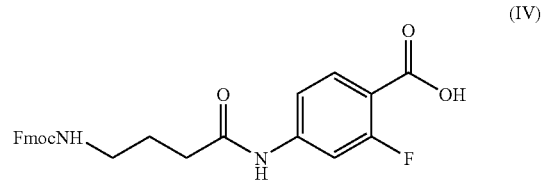
(IV)

respectively.

Building block (II) is preferably used in the synthesis of a compound of formula (I) wherein two different label are attached at the C and N-terminus of the probe.

Building block (III) is preferably used for the synthesis of cathepsin K probes.

Building block (IV) is preferably used for the synthesis of cathepsin B probes, e.g. the compounds of Examples 18 and 19.

The probes of the present inventions are preferably probes for cathepsin K, cathepsin S or cathepsin B.

The probes of the present invention are used in the context of molecular imaging in vitro, in cell-culture experiments, ex-vivo experiments or in a living organism (in vivo), including screening and whole animal imaging. Mostly preferred are imaging modalities such as optical imaging and magnetic resonance imaging (MRI).

The probes of the present invention are intended to be used for diagnostic imaging of protease activity. Most preferred are applications which provide methods of monitoring the effect of a drug or drug-like substance towards the targeted proteases. Administration of such a drug or drug like substance should have a measurable effect to the signal from the probe of the present invention.

A further most preferred aspect of the probes of the present invention is their use as imaging reagents in surgical guidance and to monitor the effect of medical treatment. Surgical guidance includes the detection of tumour margin and detection of progression of tumour metastasis.

Therefore, a further aspect of the present invention is method of imaging a living organism, comprising:
(a) administering to said organism a probe of the formula (I),
(b) exposing said organism to electromagnetic radiation which excites non-quenched fluorophore to produce a detectable signal, and
(c) detecting said signal and creating an image thereby.

Alternatively, the method of imaging a living organism comprises:
(a) administering to said organism a probe of the formula (I),
(b) exposing said organism to electromagnetic radiation which excites fluorophore to produce a detectable signal; and
(c) detecting said signal and creating an image thereby.

A "living organism" may be any live cell or whole organism comprising the cysteine protease to-be-detected, preferably the living organism is a mammal, e.g. a mouse or a rat.

The probes of the present invention are highly selective, whereby a risk of false positives can be avoided.

Abbreviations:
DMF=dimethylformamide
DMSO=dimethylsulfoxide
DCM=dichloromethane
equiv.=equivalents
sat.=saturated
THF=tetrahydrofuran
DIPEA=diisopropyl-ethyl amine
HOBt=1-hydroxybenzotriazol HBTU=O-benzotriazole-N,N,N',N'-tetramethyl-uronium-hexafluoro-phosphate
NHS=N-hydroxysuccinimidyl ester General Procedure for Solid Phase Peptide Synthesis:

The following probes were synthesized using standard solid phase peptide synthesis. The chloro-trityl-resin was used as solid support. For loading of the resin 2 equiv. of Fmoc-protected amino acid and 3 equiv. of DIPEA were solved in DCM and the reaction mixture was added to the resin (loading: 1.4 mmol/g). The reaction mixture was stirred at room temperature over night. The resin was washed with DCM and DMF. For Fmoc-deprotection the resin was treated two times for 15 minutes with 30% piperidine/DMF solution. For solid phase peptide synthesis a standard protocol was used: 4 equiv. of Fmoc-protected amino acid, 4 equiv. of HBTU, 4 equiv. of HOBt and 8 equiv. of DIPEA were solved in a mixture of DCM/DMF (1/1). The reaction mixture is stirred at room temperature for 20 minutes and then added to the resin. The reaction mixture was incubated for 2 hours. For cleavage from the solid phase, the resin was treated with 2% TFA in DCM. The solvent was coevaporated with toluene under reduced pressure and the final product was purified by preparative HPLC (Gradient: $H_2O$+0.05% TFA; 5 to 95% $CH_3CN$).

EXAMPLE 1

Cathepsin S Probe

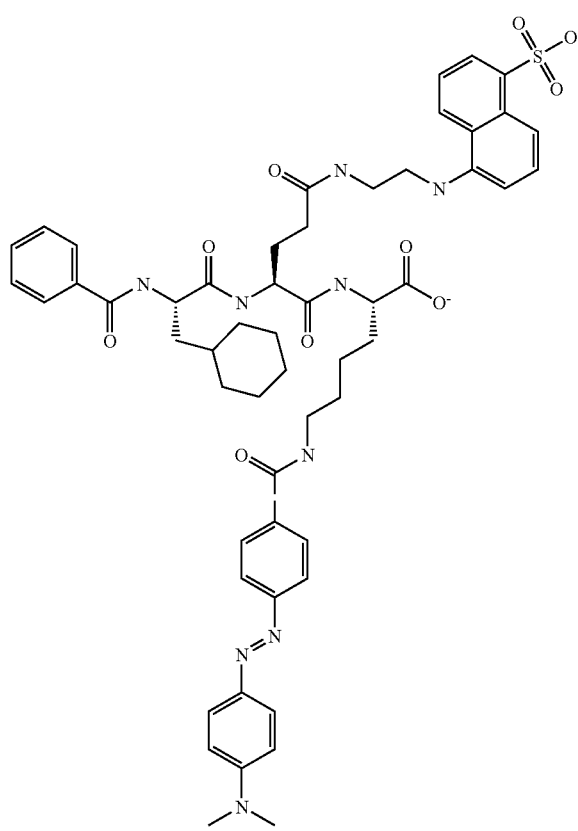 [SMILES: CN(C)c1ccc(/N=N/c2ccc(C(=O)NCCCC[C@H](NC(=O)[C@H](CCC(=O)NCCNc3cccc4c(S(=O)(=O)[O-])cccc34)NC(=O)[C@H](CC3CCCCC3)NC(=O)c3ccccc3)C(=O)[O-])cc2)cc1]

The compound was prepared on solid-support according to the general procedure and purified by HPLC ($H_2O$+0.05% TFA; 4-95% $CH_3CN$). Calculated: $[M+H]^+$=1042.26, found: $[M+H]^+$=1042.40. Yield: 82%.

The compound was prepared on solid-support according to the general procedure and purified by HPLC ($H_2O$+0.05% TFA; 4-95% $CH_3CN$). Calculated: $[M+H]^+$=1033.25, found: $[M+H]^+$=1033.40. Yield: 97%.

EXAMPLE 2

Cathepsin S Probe

EXAMPLE 3
Cathepsin S Probe
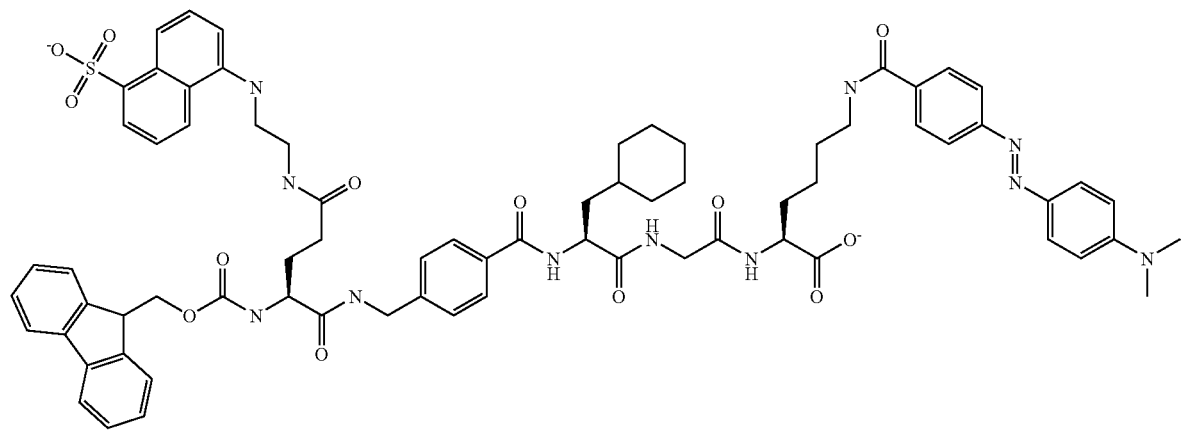
The compound was prepared on solid-support according to the general procedure and purified by HPLC(H$_2$O+0.05% TFA; 4-95% CH$_3$CN). Calculated: [M+H]$^+$=1341.59, found: [M+H]$^+$=1341.45. Yield: 91%.
EXAMPLE 4
Cathepsin S Probe
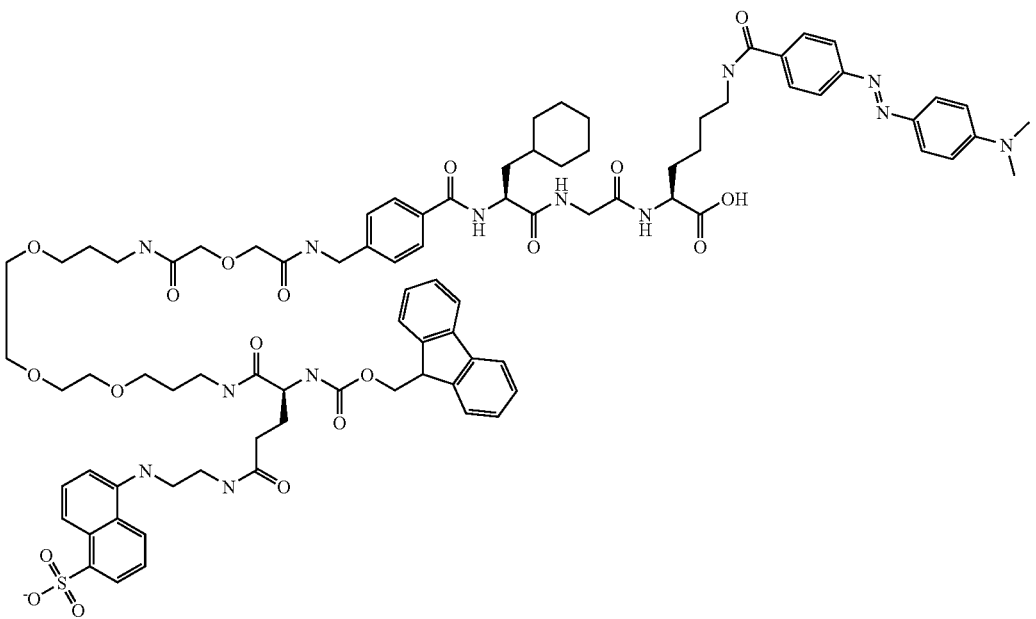

The compound was prepared on solid-support according to the general procedure and purified by HPLC (H$_2$O+0.05% TFA; 4-95% CH$_3$CN). Calculated: [M/2]$^+$=829.95, found: [M/2]$^+$=829.95. Yield: 62%.

EXAMPLE 5

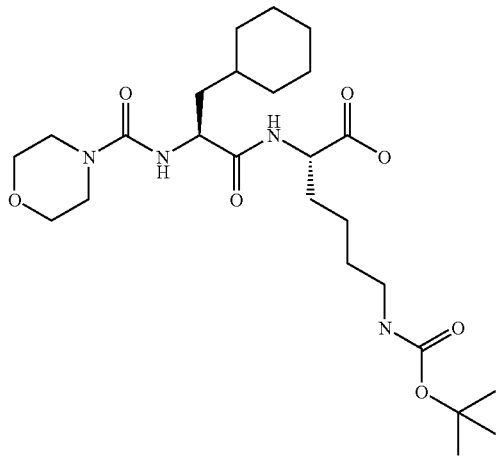 [SMILES: CC(C)(C)OC(=O)NCCCC[C@H](NC(=O)[C@H](CC1CCCCC1)NC(=O)N1CCOCC1)C(=O)O]

The compound was prepared on solid-support according to the general procedure and was further used without purification. Calculated: [M+H]$^+$=513.7, found: [M+H]$^+$=513.3.

EXAMPLE 6

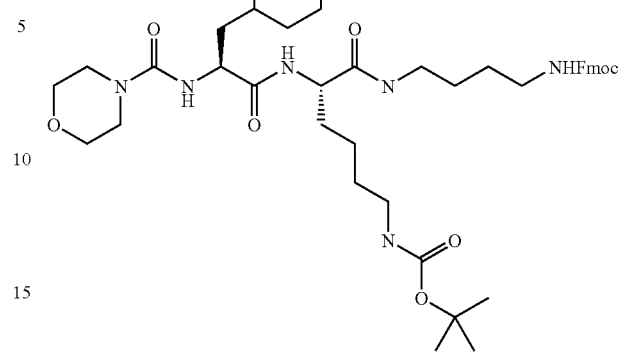

The compound of Example 5, 1.2 equiv. HOBt, 1.3 equiv. HBTU and 2 equiv. DIPEA was solved in DCM/DMF and stirred at room temperature for 20 minutes. 2 equiv. of mono-Fmoc-protected butane-1,4-diamine and 1.5 equiv. of DIPEA were added to the reaction mixture, which was then stirred over night. The solvent was removed and the remaining residue was purified on silica gel (gradient: DCM/1-5% MeOH). Calculated: [M+H]$^+$=805.0, found: [M+H]$^+$=806.5. Yield: 55%.

EXAMPLE 7

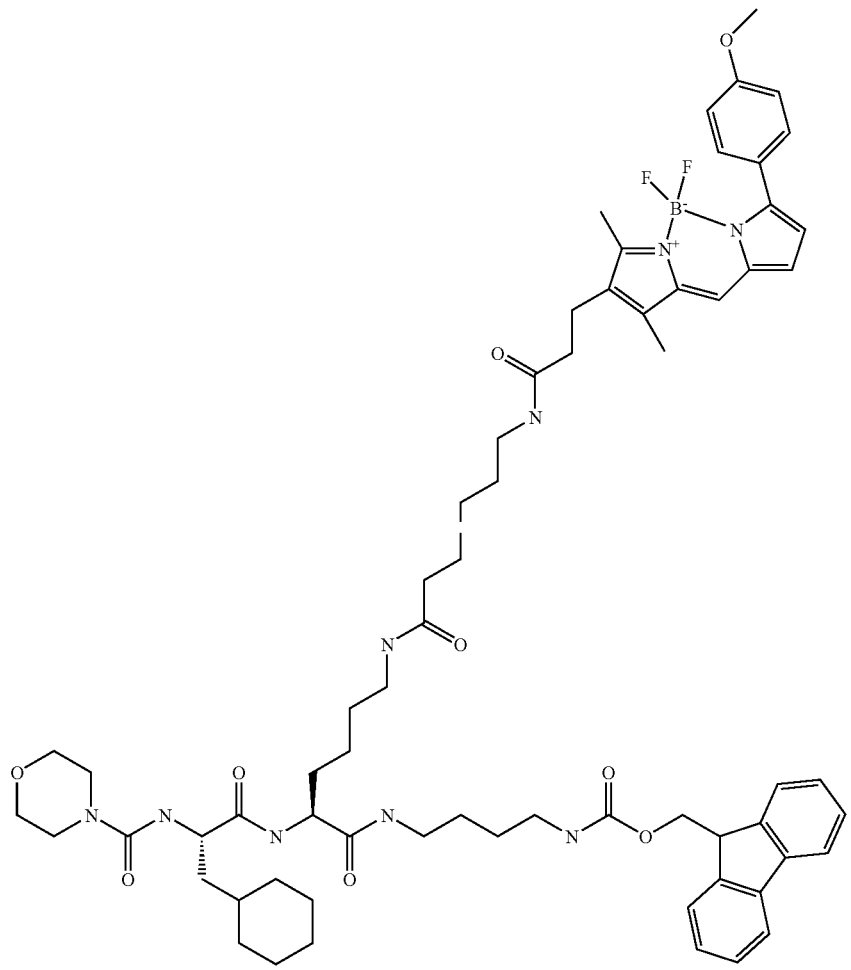 [SMILES: COc1ccc(-c2ccc3n2[B-](F)(F)[N+]2=C(C)C(CCC(=O)NCCCCCC(=O)NCCCC[C@H](NC(=O)[C@H](CC4CCCCC4)NC(=O)N4CCOCC4)C(=O)NCCCCNC(=O)OCC4c5ccccc5-c5ccccc54)=C(C)C2=C3)cc1]

For removal of the Boc-group the compound of Example 6 was solved in 50% TFA/CH$_2$Cl$_2$ and the reaction mixture was stirred for 10 minutes at room temperature. The solvent was coevaporated with toluene and the residue was solved in DMF. 1 equiv. of BodipyTMR-X-OSu and 6 equiv. of DIPEA were added to the reaction mixture. The reaction mixture was stirred at room temperature for 12 h. The solvent was removed and the final product was purified by preparative HPLC (Plab). Calculated: [M+Na]$^+$=1221.3, found: [M+Na]$^+$=1221.6.

EXAMPLE 8

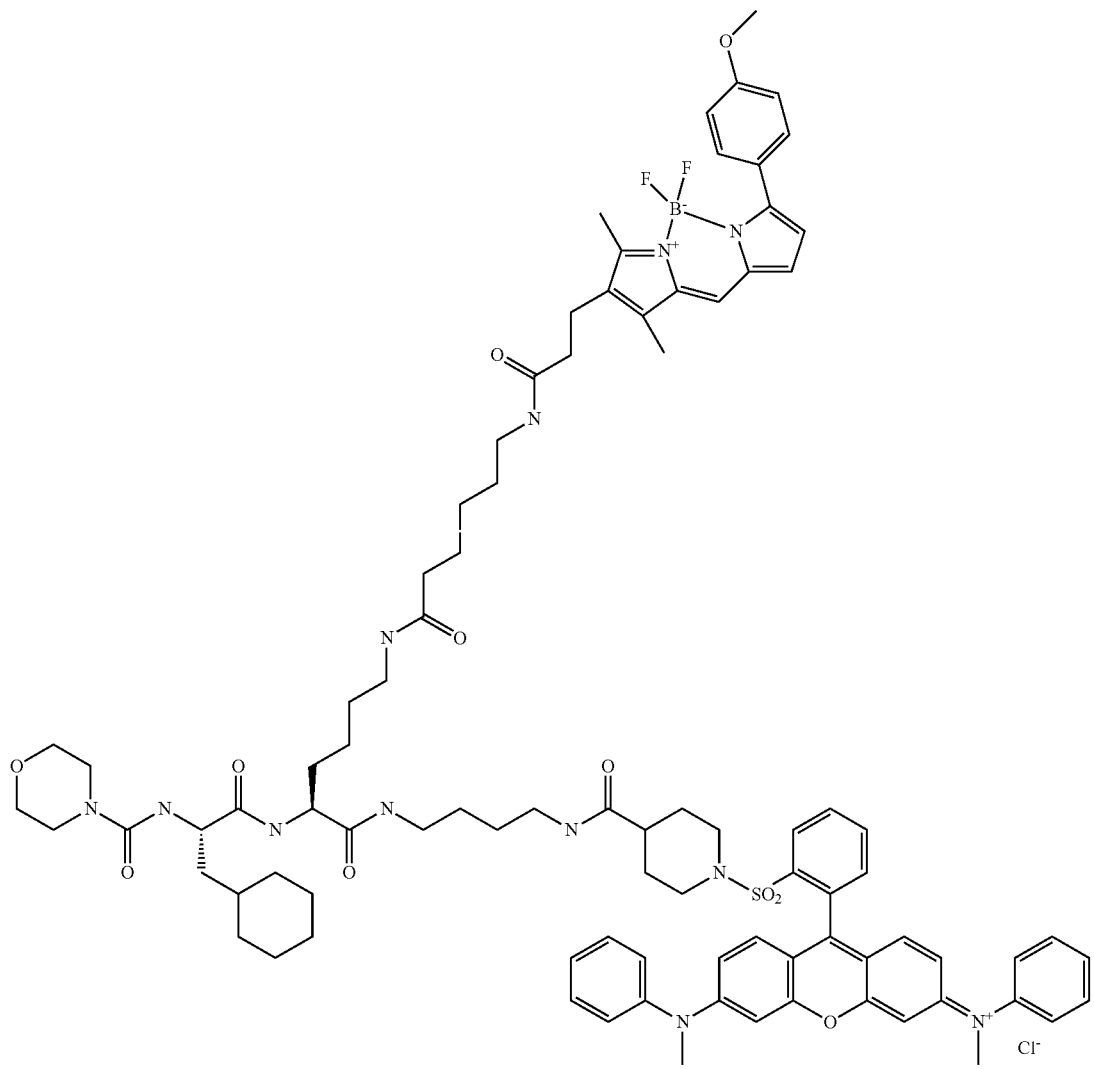

For removal of the Fmoc-group the compound of Example 7 was solved in Et$_2$NH/DMF (1/4) and the reaction mixture was stirred at room temperature for 30 minutes. The solvent was removed under reduced pressure and the residue redissolved in DMF. QSY 7OSu and 6 equiv. of DIPEA were added to the reaction mixture. The reaction mixture was stirred at room temperature for 12 h. The solvent was removed and the final product was purified by preparative HPLC (Gradient: H$_2$O+0.05% TFA; 4-95% CH$_3$CN). Calculated: [M/2]$^+$=808.4, found: [M/2]$^+$=808.5.

EXAMPLE 9

Cathepsin S Probe

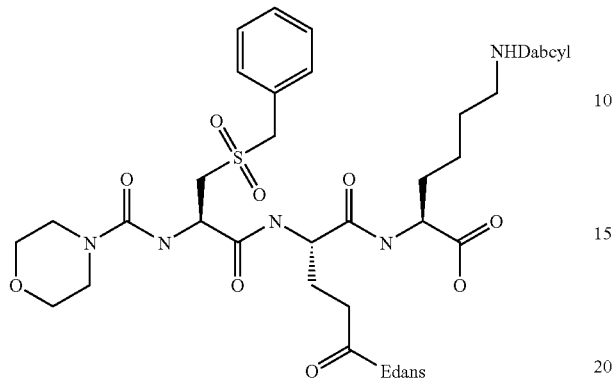

The compound was prepared on solid-support according to the general procedure and purified by HPLC (Gradient: $H_2O$+ 0.05% TFA; 4-95% $CH_3CN$). Calculated: $[M+H]^+$=1114.3, found: $[M+H]^+$=1114.4.

EXAMPLE 10

Cathepsin S Probe

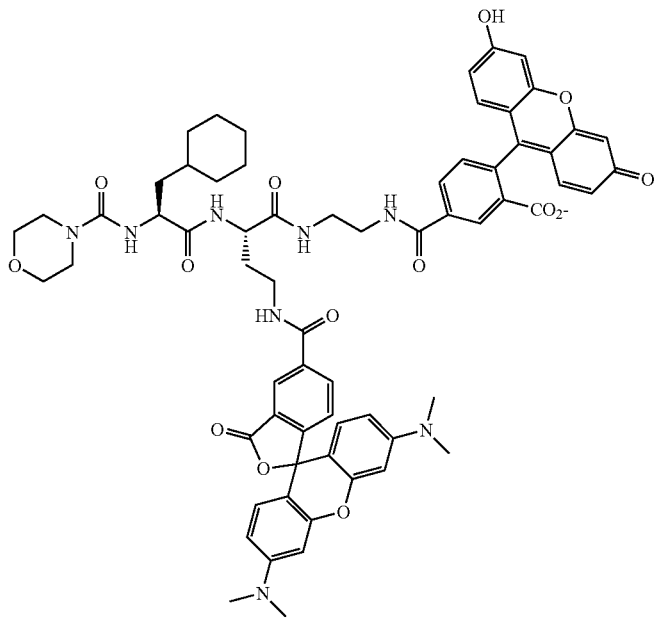

The compound was prepared on solid-support according to the general procedure for the solid phase peptide synthesis and further modified in the same way as described for the transformation of Example 5 to Example 8. The compound was purified by HPLC (Gradient: $H_2O$+0.05% TFA; 4-95% $CH_3CN$). Calculated: $[M+H]^+$=1198.3, found: $[M+H]^+$=1198.3.

EXAMPLE 11

Cathepsin S Probe

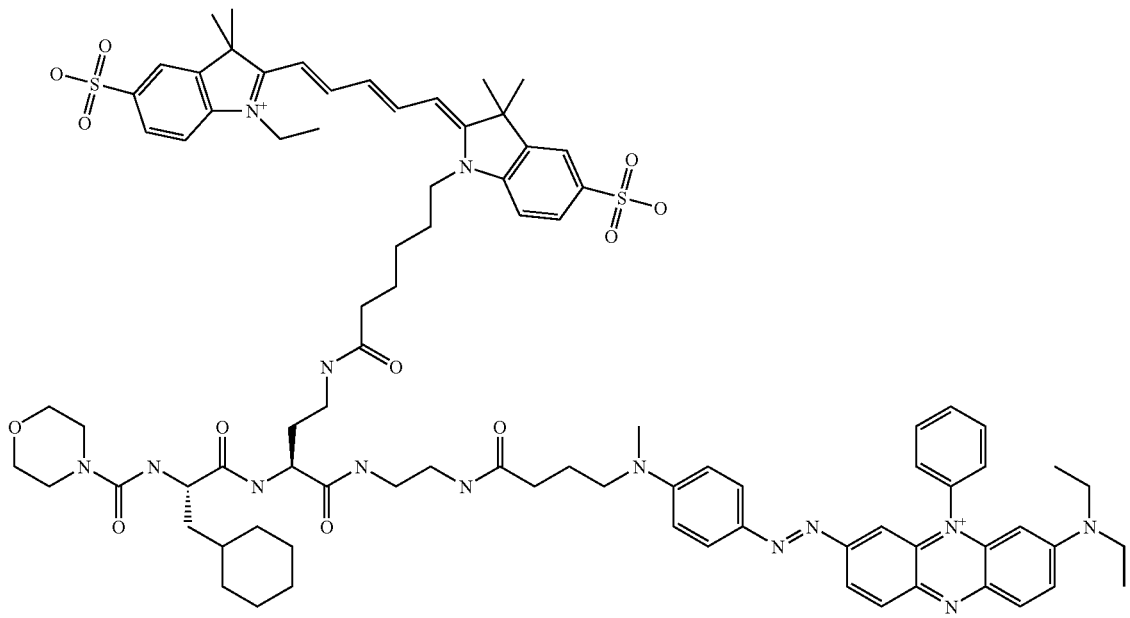 [SMILES: CCN(CC)c1ccc2nc3ccc(/N=N/c4ccc(N(C)CCCC(=O)NCCNC(=O)[C@H](CCNC(=O)CCCCCN5\C(=C/C=C/C=C/C6=[N+](CC)c7ccc(S(=O)(=O)O)cc7C6(C)C)C(C)(C)c6cc(S(=O)(=O)O)ccc65)NC(=O)[C@H](CC5CCCCC5)NC(=O)N5CCOCC5)cc4)cc3[n+](-c3ccccc3)c2c1]

The compound was prepared on solid-support according to the general procedure for the solid phase peptide synthesis and further modified in the same way as described for the transformation of Example 5 to Example 8. The compound was purified by HPLC (Gradient: $H_2O+0.05\%$ TFA; 4-95% $CH_3CN$). Calculated: $[M+Na]^+=1619.1$, found: $[M+Na]^+=1619.9$.

EXAMPLE 11a

Cathepsin S Probe

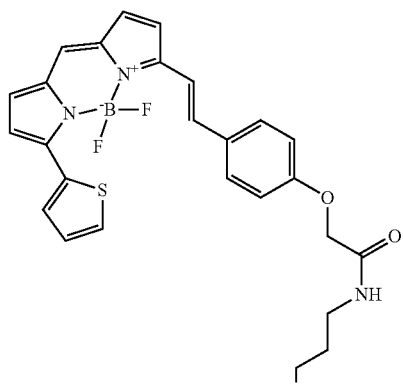

-continued

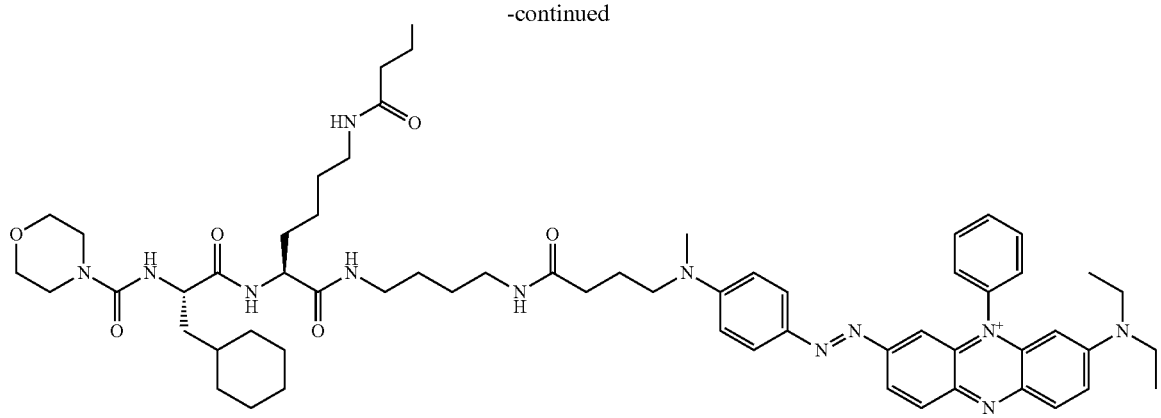

The compound was prepared on solid-support according to the general procedure for the solid phase peptide synthesis and further modified in the same way as described for the transformation of Example 5 to Example 8. The compound was purified by HPLC (Gradient: $H_2O+0.05\%$ TFA; 4-95% $CH_3CN$).

EXAMPLE 12

Cathepsin K Probe

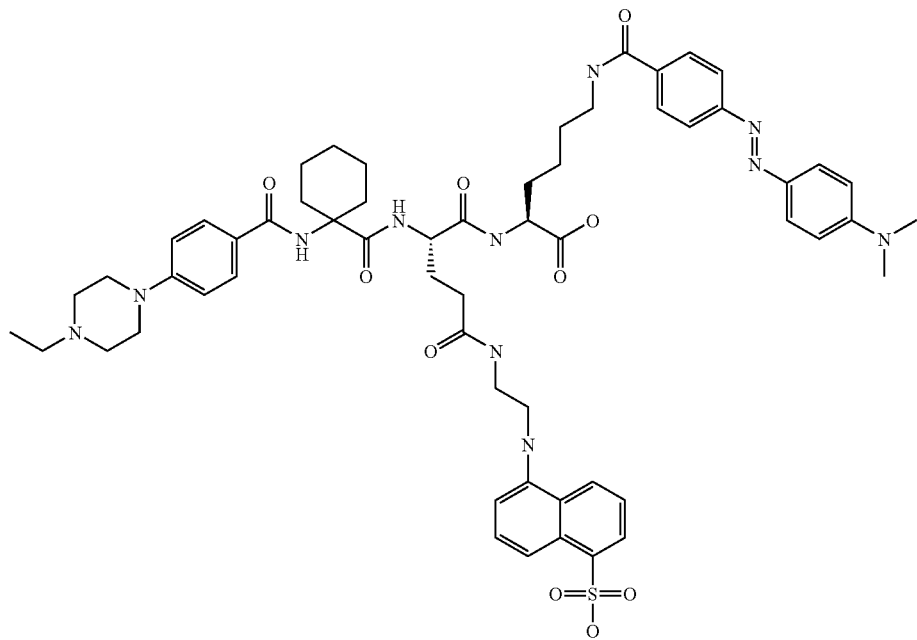 [SMILES: CCN1CCN(c2ccc(C(=O)NC3(C(=O)N[C@@H](CCC(=O)NCCNc4cccc5c(S(=O)(=O)O)cccc45)C(=O)N[C@@H](CCCCNC(=O)c4ccc(/N=N/c5ccc(N(C)C)cc5)cc4)C(=O)O)CCCCC3)cc2)CC1]

The compound was prepared on solid-support according to the general procedure and purified by HPLC ($H_2O+0.05\%$ TFA; 4-95% $CH_3CN$). Calculated: $[M+H]^+=1117.37$, found: $[M+H]^+=1117.50$. Yield: 45%.

EXAMPLE 13

Cathepsin K Probe

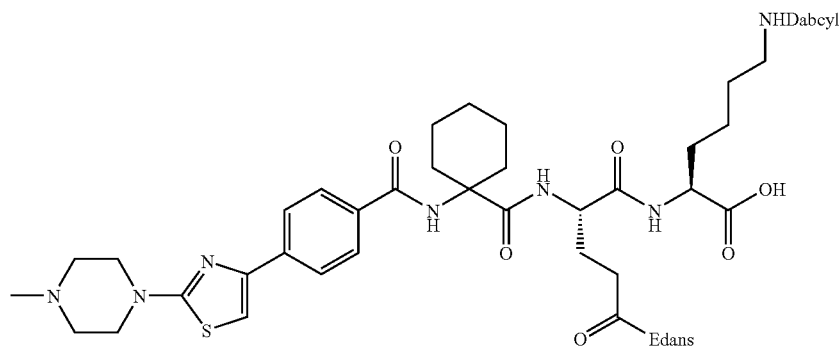

The compound was prepared on solid-support according to the general procedure and purified by HPLC (H$_2$O+0.05% TFA; 4-95% CH$_3$CN). Calculated: [M+H]$^+$=1186.4, found: [M+H]$^+$=1186.3. Yield: 90%.

EXAMPLE 14

Cathepsin K Probe

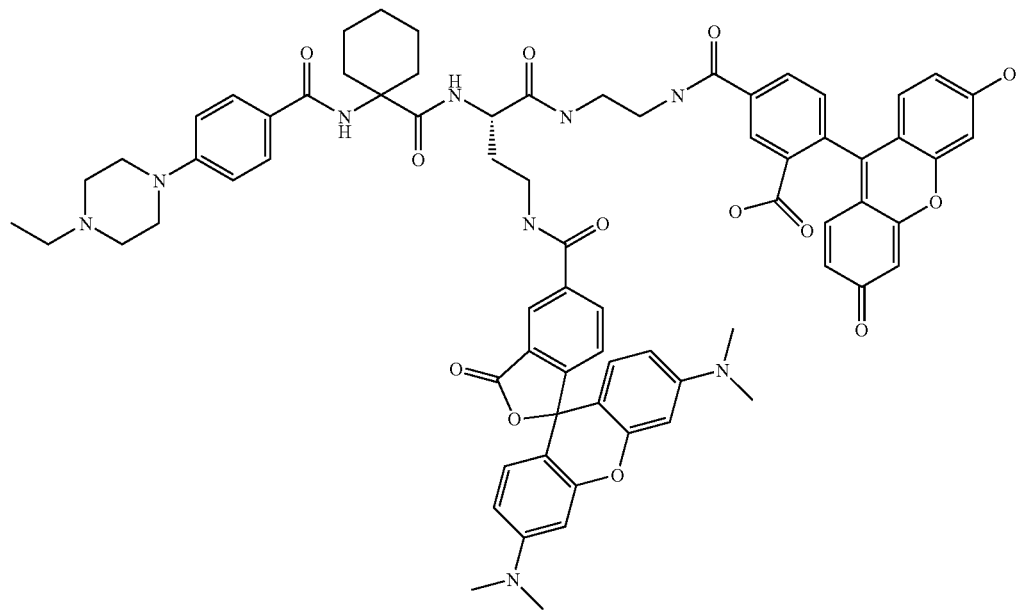 [SMILES: CCN1CCN(c2ccc(C(=O)NC3(C(=O)N[C@@H](CCNC(=O)c4ccc5c(c4)C(=O)OC54c5ccc(N(C)C)cc5Oc5cc(N(C)C)ccc54)C(=O)NCCNC(=O)c4ccc(-c5c6ccc(=O)cc-6oc6cc(O)ccc56)c(C(=O)O)c4)CCCCC3)cc2)CC1]

The compound was prepared on solid-support according to the general procedure and purified by HPLC (H$_2$O+0.05% TFA; 4-95% CH$_3$CN). Calculated: [M+H]$^+$=1273.4, found: [M+H]$^+$=1273.4.

EXAMPLE 15
Cathepsin K Probe
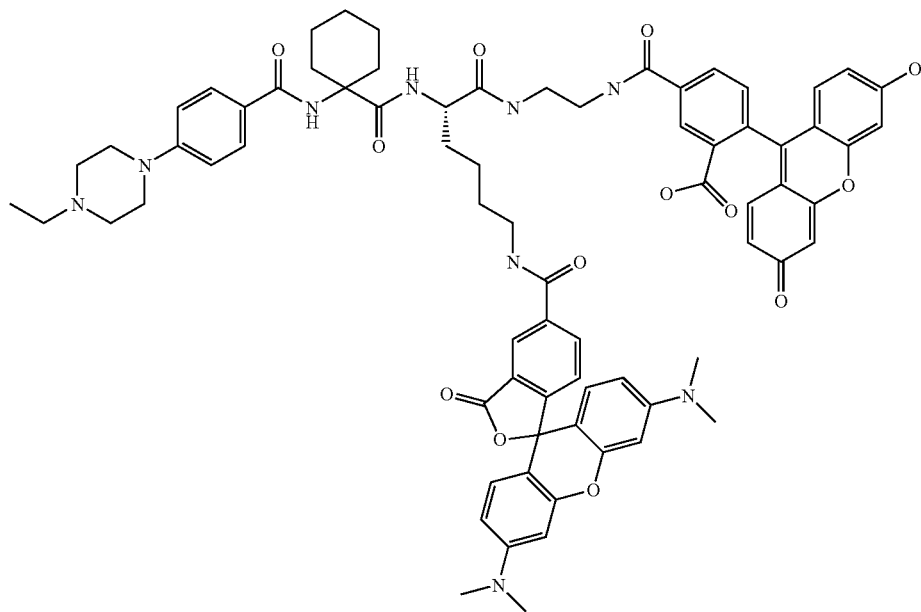 [SMILES: CCN1CCN(c2ccc(C(=O)NC3(C(=O)N[C@@H](CCCCNC(=O)c4ccc5c(c4)C(=O)OC54c5ccc(N(C)C)cc5Oc5cc(N(C)C)ccc54)C(=O)NCCNC(=O)c4ccc(-c5c6ccc(=O)cc-6oc6cc(O)ccc56)c(C(=O)O)c4)CCCCC3)cc2)CC1]
The compound was prepared on solid-support according to the general procedure for the solid phase peptide synthesis and further modified in the same way as described for the transformation of Example 5 to Example 8. The compound was purified by HPLC (H$_2$O+0.05% TFA; 4-95% CH$_3$CN). Calculated: [M+H]$^+$=1301.5, found: [M+H]$^+$=1301.3.
EXAMPLE 16
Cathepsin K Probe
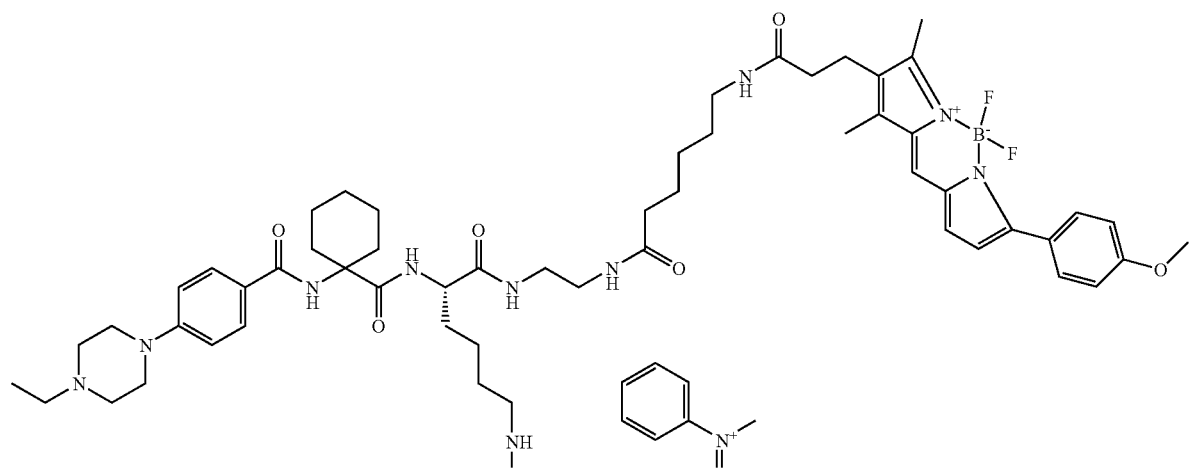

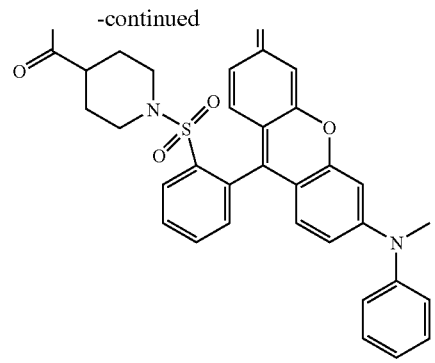
The compound was prepared on solid-support according to the general procedure for the solid phase peptide synthesis and further modified in the same way as described for the transformation of Example 5 to Example 8. The compound was purified by HPLC (H₂O+0.05% TFA; 4-95% CH₃CN). Calculated: [M]⁺=1663.9, found: [M]⁺=1663.7.
EXAMPLE 17
Cathepsin K Probe
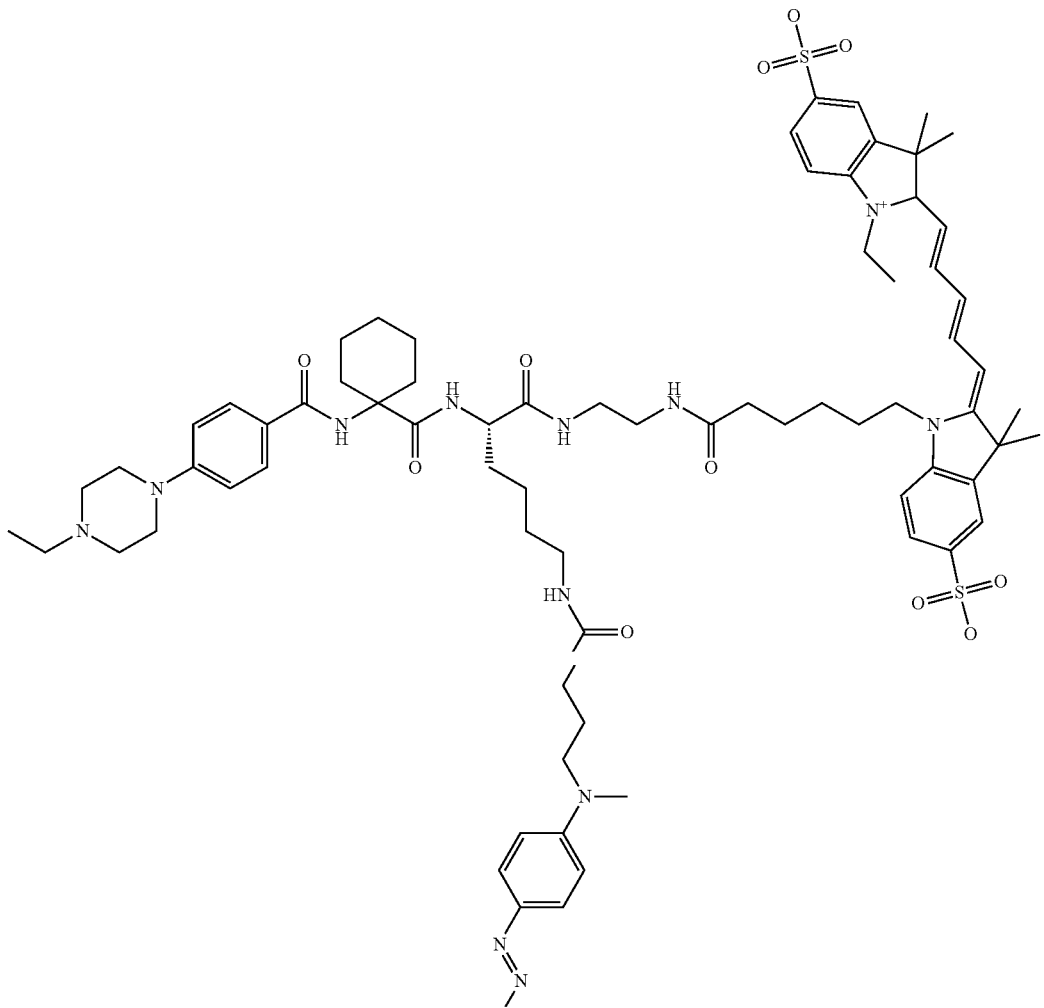

-continued
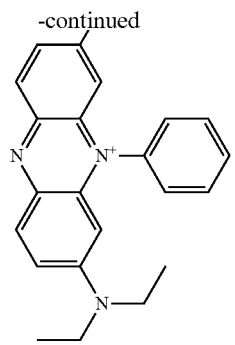
15
The compound was prepared on solid-support according to the general procedure for the solid phase peptide synthesis and further modified in the same way as described for the transformation of Example 5 to Example 8. The compound was purified by HPLC ($H_2O$+0.05% TFA; 4-95% $CH_3CN$).
EXAMPLE 18
Cathepsin K Probe
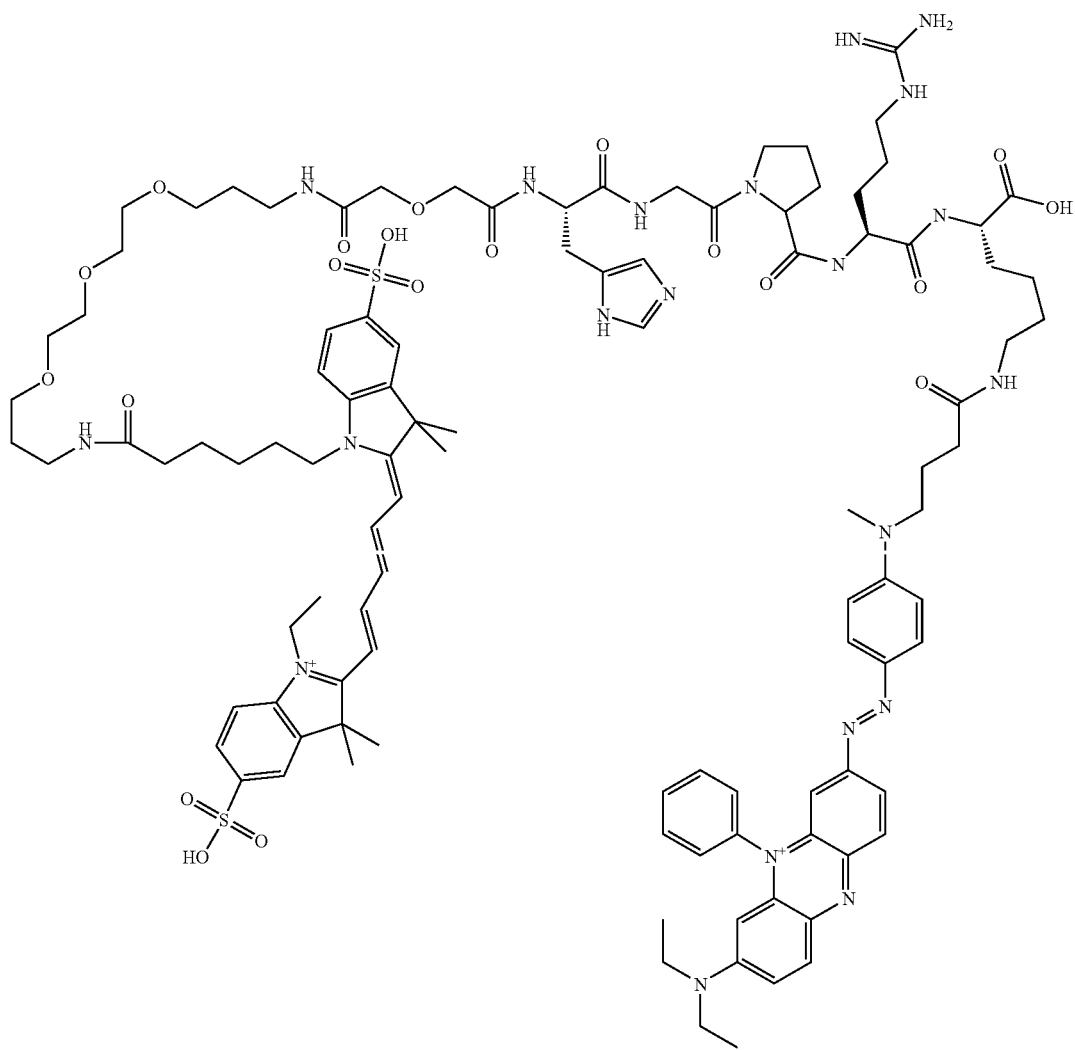 [SMILES: CCN(CC)c1ccc2nc3ccc(/N=N/c4ccc(N(C)CCCC(=O)NCCCC[C@H](NC(=O)[C@H](CCCNC(=N)N)NC(=O)C5CCCN5C(=O)CNC(=O)[C@H](Cc5cnc[nH]5)NC(=O)COCC(=O)NCCCOCCOCCOCCCNC(=O)CCCCCN5\C(=C/C=C/C=C/C6=[N+](CC)c7ccc(S(=O)(=O)O)cc7C6(C)C)C(C)(C)c6cc(S(=O)(=O)O)ccc65)C(=O)O)cc4)cc3[n+](-c3ccccc3)c2c1]

The compound was prepared on solid-support according to the general procedure for the solid phase peptide synthesis and further modified in the same way as described for the transformation of Example 5 to Example 8. The compound was purified by HPLC (H₂O+0.05% TFA; 4-95% CH₃CN).

EXAMPLE 19

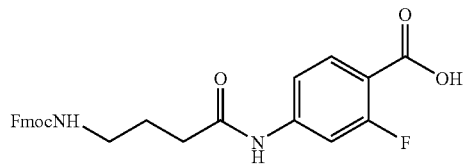

4-Fmoc-amino buturic acid, 1.1 equiv. of HOBt, 1.1 equiv. of HBTU and 2 equiv. of DIPEA were solved in DMF/DCM (1/1) and stirred for 20 minutes at room temperature. 4-Amino-2-fluoro benzoic acid and 2 equiv. of DIPEA were added to the reaction mixture and stirred at room temperature over night. The solvent was removed under reduced pressure and the remaining residue is chromatographed (gradient: DCM/1-3% MeOH). Calculated: $[M+H]^+$=463.5, found: $[M+H]^+$=463.1. Yield: 60%.

EXAMPLE 20

Cathepsin B Probe

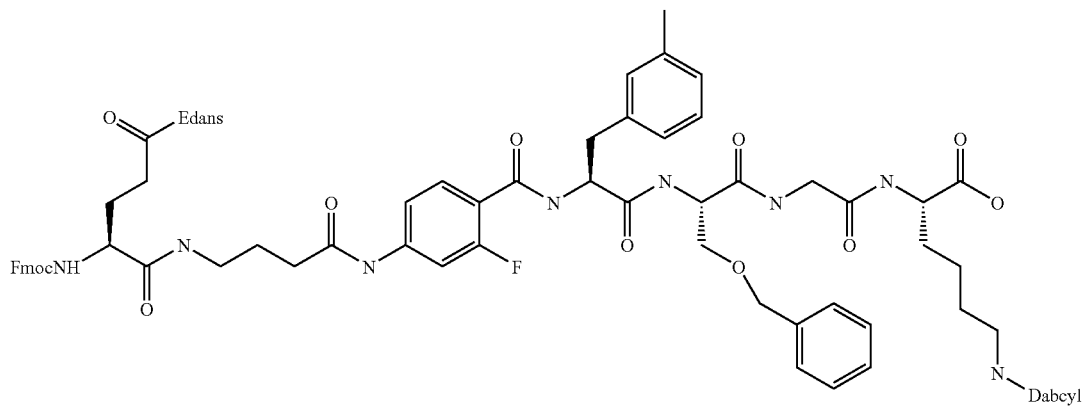

The compound was prepared on solid-support according to the general procedure and purified by HPLC (H₂O+0.05% TFA; 4-95% CH₃CN). Calculated: $[M+H]^+$=1615.8, found: $[M+H]^+$=1615.5. Yield: 42%.

EXAMPLE 21

Cathepsin B Probe

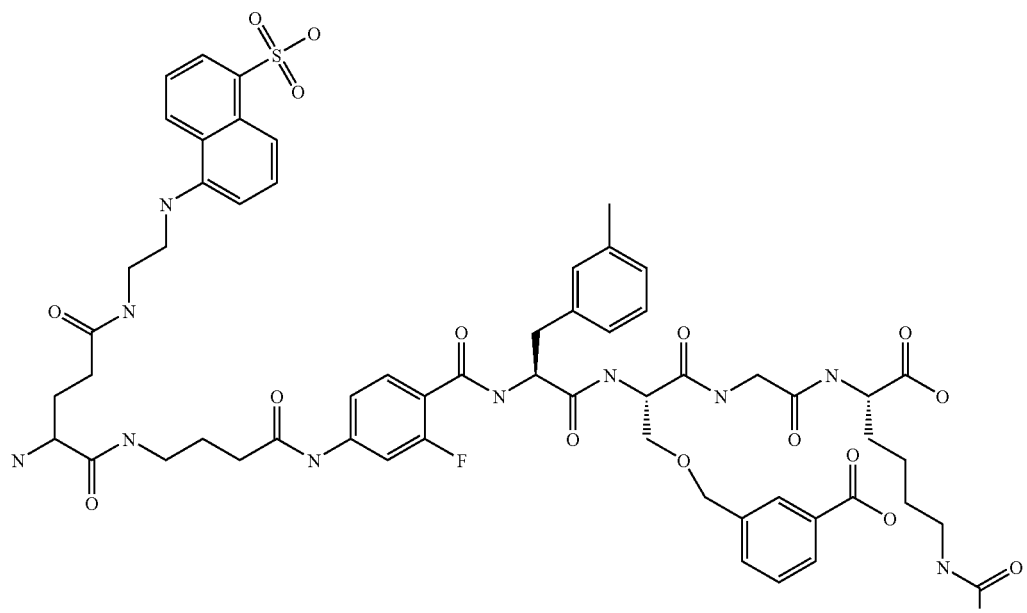

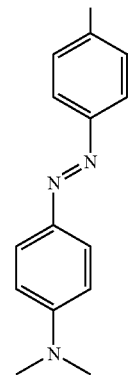

The compound was prepared on solid-support according to the general procedure and purified by HPLC (H₂O+0.05% TFA; 4-95% CH₃CN). Calculated: $[M/2]^+=718.3$, found: $[M/2]^+=718.8$. Yield: 10%

EXAMPLE 22

1-Boc-4-(3-chloropropyl)-piperazine

To a solution of 4.94 g tert-Butyl-1-piperazine-carboxylate and 12.66 g 1-Bromo-3-chloropropane in 15 ml DMF (dry) was added 4.08 g K₂CO₃ and the reaction heated to 50° C. for one minute and stirred at room temperature for additional 3 h. The reaction mixture is pored into 200 ml of water and extracted with DCM. The combined organic phases were washed with water and dried over MgSO₄ and evaporated in vacuo. The product was purified by flash column chromatography (n-heptane/ethylacetate 1:1, RF=0.3) Yield 3.9 g.

EXAMPLE 23

1-Boc-4-(3-azidopropyl)-piperazine

Tert-Butyl-4-(3-Chloropropyl)-1-piperazine carboxylate and sodium-azide were dissolved (suspended) in 8 ml DMSO dry and heated to 90° C. for 15 h. The reaction mixture was allowed to cool to room temperature and pored into 50 ml of water. The product was extracted with DCM and the combined organic phases dried over MgSO₄. The product was purified by flash column chromatography (n-heptane/ethylacetate 1:1, RF=0.34). Yield: 3.5 g.

EXAMPLE 24

(3-azidopropyl)-piperazine 3.5 g 1-Boc-4-(3-azidopropyl)-piperazine was dissolved in 30 ml MeOH/DCM (3/1) and 10 ml TFA were added. The reaction mixture was stirred at room temperature for 20 min and the product precipitated by the addition of 150 ml tert-Butyl-methyl ether. Yield 2.3 g.

EXAMPLE 25

Methyl-Piperazinyl Thiourea

Thiocarbonyldiimidazole and 1 equiv. of N-methyl-piperazine were solved in THF. The reaction mixture was stirred at room temperature for 1 h and at 55° C. for 1 h. Half of the solvent was removed and the same amount of 2.0 M NH₃/MeOH solution was added to the reaction mixture, which was then stirred at room temperature over night and finally at 55° C. for 2 h. The product was filtrated and washed with ether Yield: 57%.

EXAMPLE 26

Methyl-piperazinyl-thiazyl-benzoic acid

4-Methyl-piperazinyl thiourea and 4-(2-Bromoacetyl)benzoic acid were solved in THF. The reaction mixture was heated to reflux for 3 h. The product was filtrated and washed with ether.

EXAMPLE 27

Activity-Assays

For the in vitro assays 1 μg protease in 20 μl AHNP-Puffer (150 mM Acetat/HEPES, 300 mM NaCl; 0.001% Pluronic pH 6.5 and 50 μl cysteine (300 mM) was activated for 5 minutes at 37° C. The substrates were solved in DMSO and added to enzyme solution with a final concentration of 50 μM.

Fluorescence was measured with an Tecan SAFIRE II spectrometer (excitation wavelength: 336 nm; emission wavelength: 490 nm; excitation band: 10.0 nm; emission band: 10.0 nm; amplification (manual): 90).

TABLE 1

Results of in vitro assay for the compound of Example 2

|  | Cath S | Cath K | Cath X | Papain | Cath B | Cath L |
|---|---|---|---|---|---|---|
| Mw enzyme (Da) | 24000 | 27000 | 27000 | 23400 | 27500 | 29000 |
| $E_O$ (moles/L) | 2.3E−08 | 6.3E−08 | 2.8E−08 | 1.1E−08 | 5.2E−09 | 3.6E−09 |
| $K_M$ (M) | 3.2E−05 | 1.9E−04 | 8.7E−04 | 5.2E−04 | 1.2E−04 | 8.3E−03 |
| $V_{max}$ (nmoles/s) | 2.4 | 0.3 | 72.3 | 1.6 | 0.1 | 4.5 |

TABLE 1-continued

Results of in vitro assay for the compound of Example 2

| | Cath S | Cath K | Cath X | Papain | Cath B | Cath L |
|---|---|---|---|---|---|---|
| $K_{cat}(s^{-1})$ | 0.11 | 0.00 | 2.6 | 0.1 | 0.0 | 1.26 |
| $K_{cat}/K_M(M^{-1}s^{-1})$ | 3260 | 27 | 30 | 273 | 250 | 152 |

(measurement performed at pH 7.5)

TABLE 2

Results of in vitro assay for the compound of Example 10

| | Cath S | Cath K | Cath X | Papain | Cath B | Cath L |
|---|---|---|---|---|---|---|
| Mw enzyme (Da) | 24000 | 27000 | 40000 | 23400 | 27500 | 29000 |
| $E_O$ (moles/L) | 3.0E−08 | 3.8E−08 | 2.8E−08 | 2.4E−08 | 1.0E−08 | 3.2E−09 |
| $K_M$ (M) | — | 3.5E−05 | 4.7E−01 | 6.3E−06 | 8.8E−04 | 7.1E−03 |
| $V_{max}$ (nmoles/s) | — | 7.3 | 7997 | 0.04 | 2.6 | 9.7 |
| $K_{cat}(s^{-1})$ | — | 0.192 | 287.4 | 0.002 | 0.25 | 3.01 |

(measurement performed at pH 5.5)

The invention claimed is:

1. A molecular probe for cathepsin protease S of the formula (I):

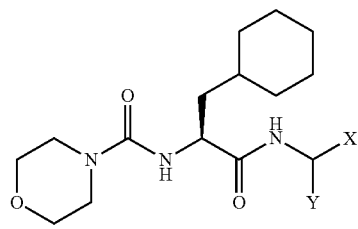

wherein
X is —CONH—R2-L2
Y is-L-R1-L1, and
R1 and R2 are, independently of each other, each a linker;
L is a bond or a group allowing for a facile conjugation of the group L1;
L1 and L2 are, independent of each other, at least one label optionally bound to a solid support.

2. The molecular probe according to claim 1, wherein L is a direct bond or a group selected from

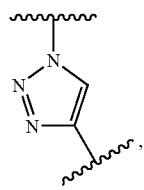 [SMILES: *c1cn(*)nn1]

—(NRx)-, —O—, —C═N—, —C(═O)—, —C(═O)—NH—, —NH—C(═O)—, —C(═O)H, —CRx═Cry—, —C≡C— and phenyl, wherein Rx and Ry are independently H or $(C_1$-$C_6)$alkyl.

3. The molecular probe according to claim 1, wherein R1 or R2 is a straight or branched chain alkylene group with 1 to 300 carbon atoms, wherein optionally;

(a) one or more carbon atoms are replaced by oxygen;
(b) one or more carbon atoms are replaced by nitrogen carrying a hydrogen atom, and the adjacent carbon atoms are substituted by oxo, representing an amide function —NH—CO—;
(c) one or more carbon atoms are replaced by an ester function —O—CO—;
(d) the bond between two adjacent carbon atoms is a double or a triple bond; and/or
(e) two adjacent carbon atoms are replaced by a disulfide linkage.

4. The molecular probe according to claim 3, wherein labels L1 and L2 are independently of each other a spectroscopic probe; a fluorophore; a quencher or a chromophore; a magnetic probe; a contrast reagent; a molecule which is one part of a specific binding pair which is capable of specifically binding to a partner; a molecule covalently attached to a solid support; a biomolecule; or a positively charged linear or branched polymer.

5. The molecular probe according to claim 4, wherein labels L1 and L2 are independently of each other bound to a positively charged linear or branched polymer.

6. The molecular probe according to claim 5, wherein one of labels L1 and L2 is a linear poly(arginine) of D- and/or L-arginine with 6-15 arginine residues.

7. The molecular probe according to claim 4, wherein L1 is one member and L2 is the other member of two interacting spectroscopic probes L1/L2.

8. The molecular probe according to claim 7, wherein L1/L2 is a FRET pair.

9. The molecular probe according to claim 8, wherein one of labels L1 and L2 is a fluorophore selected from Alexa 350, dimethylaminocoumarin, 5/6-carboxyfluorescein, Alexa 488, ATTO 488, DY-505, 5/6-carboxyfluorescein, Alexa 488, Alexa 532, Alexa 546, Alexa 555, ATTO 488, ATTO 532, tetramethylrhodamine, Cy 3, DY-505, DY-547, Alexa 635, Alexa 647, ATTO 600, ATTO 655, DY-632, Cy 5, DY-647 and Cy5.5, and the other of labels L1 and L2 is a quencher selected from Dabsyl, Dabcyl, BHQ 1, QSY 35, BHQ 2, QSY 9, ATTO 540Q, BHQ 3, ATTO 612Q, and QSY 21.

10. A method of using a probe according to claim 1 for imaging a living organism, said method comprising:
 (a) administering to said organism a probe of the formula (I);
 (b) exposing said organism to electromagnetic radiation which excites non-quenched fluorophore to produce a detectible signal; and
 (c) detecting said signal and creating an image thereby.

11. A method of using a probe according to claim 1 for imaging a living organism, said method comprising:
 a) administering to said organism a probe of the formula (I);
 (b) exposing said organism to electromagnetic radiation which excites fluorophore to produce a detectible signal; and
 (c) detecting said signal and creating an image thereby.

12. The molecular probe according to claim 3, wherein every third carbon atom of said straight or branched chain alkylene group is replaced by oxygen.

13. The molecular probe according to claim 12, wherein said straight or branched chain alkylene group comprises a poylethyleneoxy group with 1 to 100 ethyleneoxy units.

14. The molecular probe according to claim 4, wherein said solid support is a glass slide, a microtiter plate or a polymer.

15. The probe according to claim 1, selected from the group consisting of

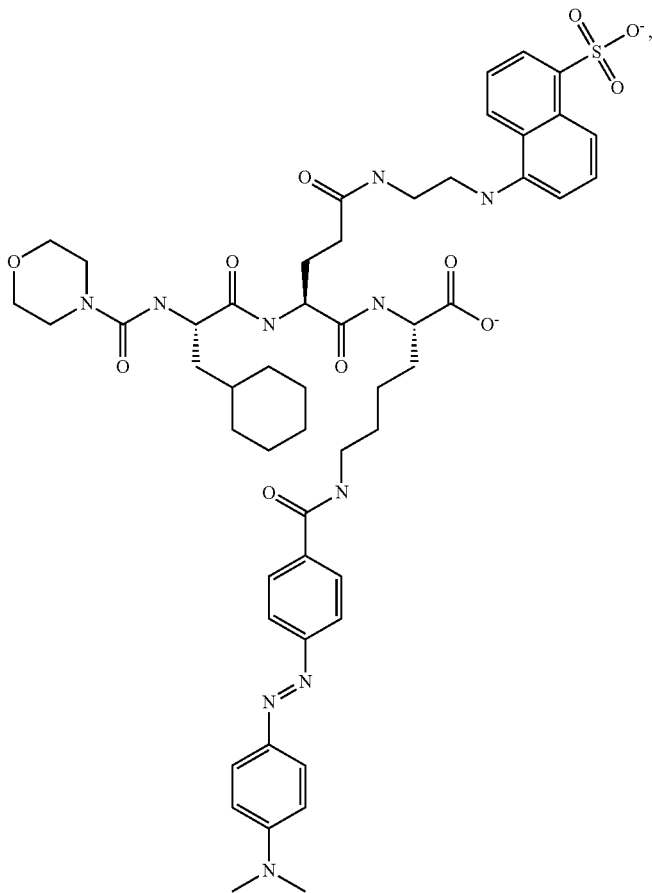

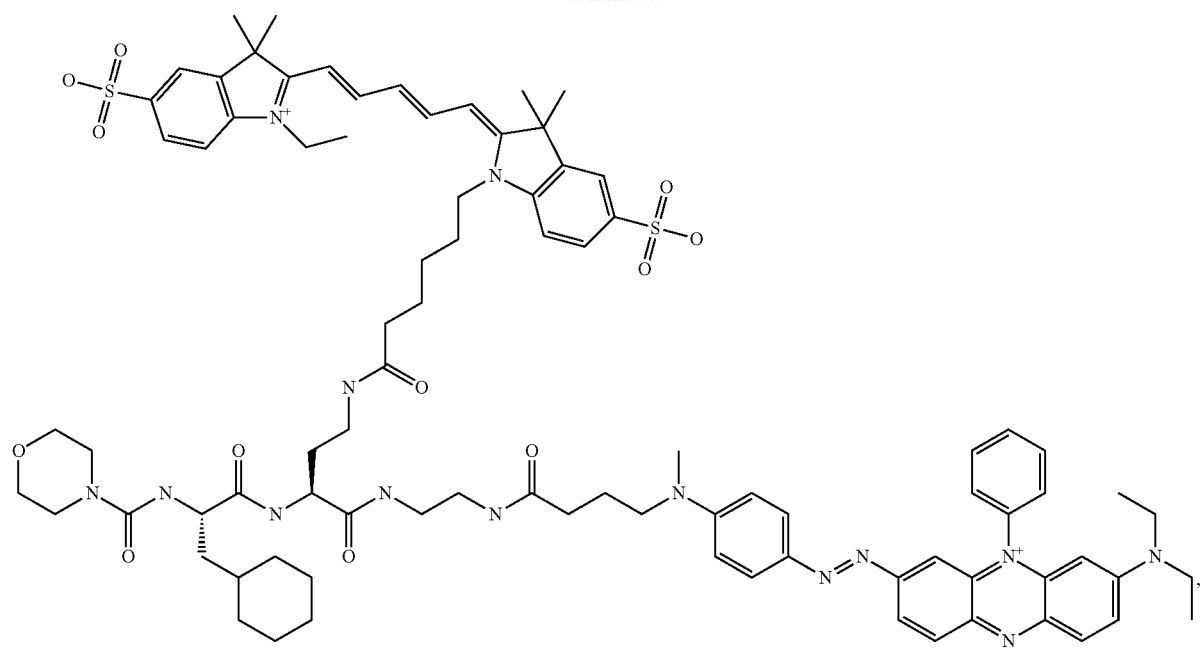
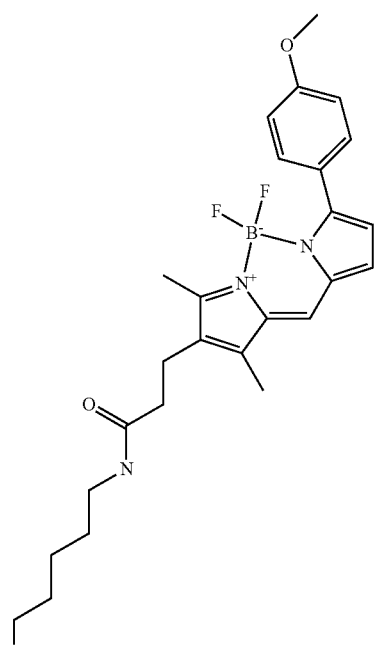

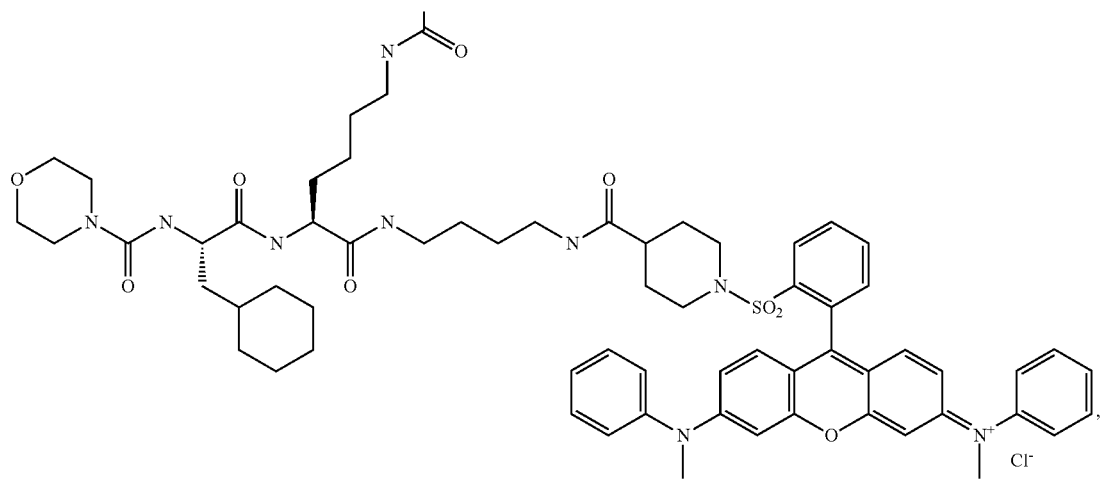
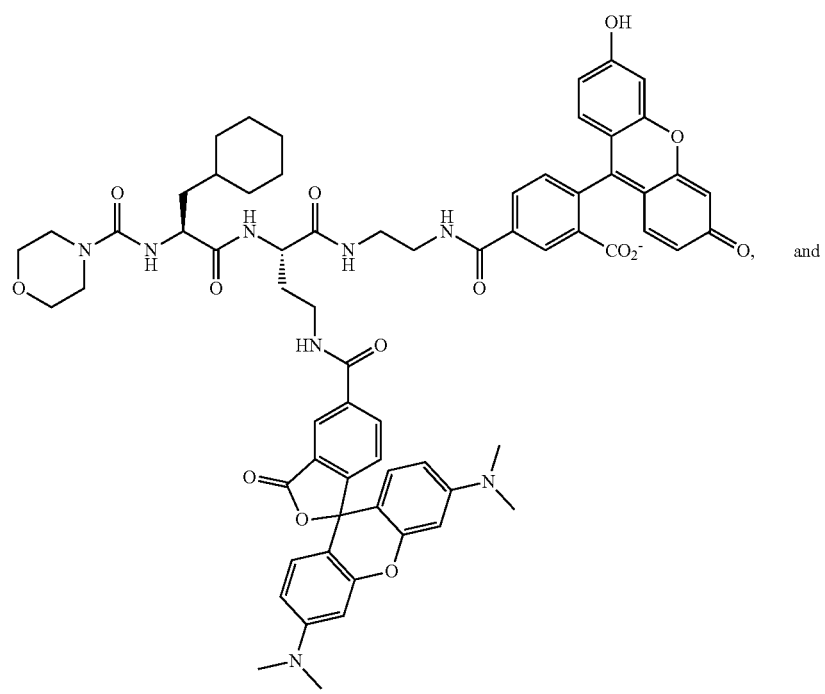
and

-continued
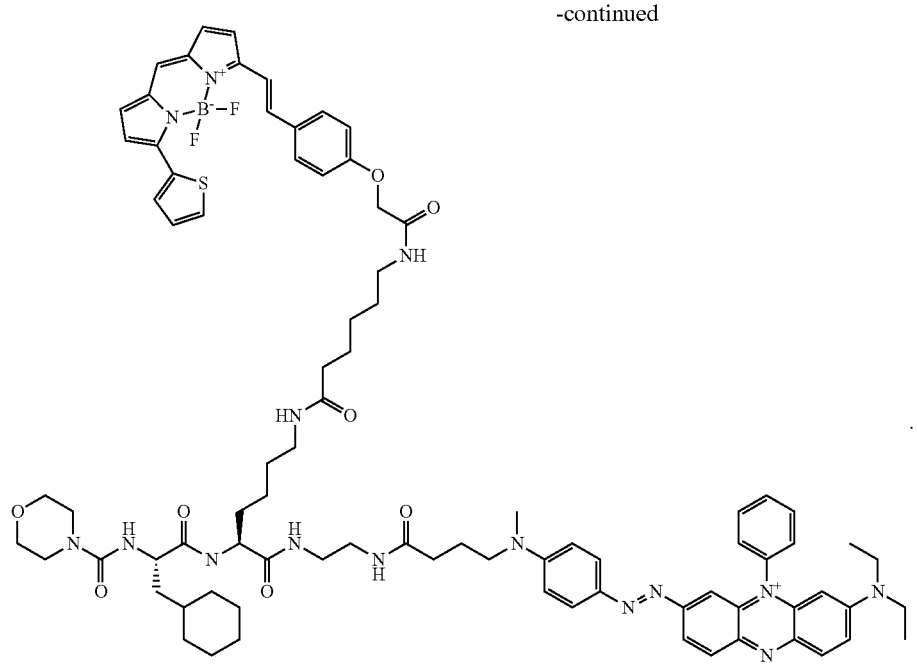
\* \* \* \* \*